(12) United States Patent
Davis et al.

(10) Patent No.: US 9,061,009 B2
(45) Date of Patent: Jun. 23, 2015

(54) MIXED LINEAGE KINASES AND METABOLIC DISORDERS

(75) Inventors: Roger J. Davis, Princeton, MA (US); Anja Jaeschke, Cincinnati, OH (US)

(73) Assignee: University of Massachusetts, Boston, MA (US)

( * ) Notice: Subject to any disclaimer, the term of this patent is extended or adjusted under 35 U.S.C. 154(b) by 612 days.

(21) Appl. No.: 12/663,436

(22) PCT Filed: Jun. 9, 2008

(86) PCT No.: PCT/US2008/066350
§ 371 (c)(1),
(2), (4) Date: Apr. 29, 2010

(87) PCT Pub. No.: WO2008/151323
PCT Pub. Date: Dec. 11, 2008

(65) Prior Publication Data
US 2010/0215665 A1  Aug. 26, 2010

Related U.S. Application Data

(60) Provisional application No. 60/933,799, filed on Jun. 8, 2007.

(51) Int. Cl.
*A61K 31/40* (2006.01)
*C12Q 1/68* (2006.01)

(52) U.S. Cl.
CPC ............ *A61K 31/40* (2013.01); *C12Q 1/6883* (2013.01); *C12Q 2600/158* (2013.01); *C12Q 2600/136* (2013.01)

(58) Field of Classification Search
USPC .......... 424/9.1, 9.2; 514/1, 2, 44; 435/6, 91.1, 435/91.31, 455, 6.11, 7.1, 375; 536/23.1, 536/24.5, 23.2, 23.53; 530/300, 350, 387.9
See application file for complete search history.

(56) References Cited

U.S. PATENT DOCUMENTS

| | | | |
|---|---|---|---|
| 5,736,381 A | 4/1998 | Davis et al. | |
| 6,043,083 A | 3/2000 | Davis et al. | |
| 6,136,596 A | 10/2000 | Davis et al. | |
| 6,174,676 B1 | 1/2001 | Davis et al. | |
| 6,410,693 B1 | 6/2002 | Davis et al. | |
| 6,455,525 B1 | 9/2002 | Singh et al. | |
| 6,541,605 B1 | 4/2003 | Davis et al. | |
| 6,610,523 B1 | 8/2003 | Davis et al. | |
| 6,630,500 B2 | 10/2003 | Gingrich et al. | |
| 6,811,992 B1 | 11/2004 | Liu | |
| 6,831,075 B2 | 12/2004 | Singh et al. | |
| 6,841,567 B1 | 1/2005 | Hudkins et al. | |
| 6,943,000 B2 | 9/2005 | Davis et al. | |
| 7,074,793 B2 | 7/2006 | Hudkins et al. | |
| 7,115,613 B2 | 10/2006 | Gingrich et al. | |
| 7,122,679 B2 | 10/2006 | Ator et al. | |
| 7,169,802 B2 | 1/2007 | Hudkins et al. | |
| 7,230,026 B2 | 6/2007 | Gingrich et al. | |
| 7,241,779 B2 | 7/2007 | Hudkins et al. | |
| 7,288,650 B2 | 10/2007 | Hudkins et al. | |
| 7,671,064 B2 | 3/2010 | Becknell et al. | |
| 7,838,294 B2 | 11/2010 | Davis et al. | |
| 7,897,572 B1 | 3/2011 | Davis et al. | |
| 2004/0185460 A1 | 9/2004 | Angeles et al. | |
| 2005/0209299 A1 | 9/2005 | Shapiro | |
| 2006/0128780 A1* | 6/2006 | Hudkins et al. | ............... 514/410 |
| 2006/0276497 A1 | 12/2006 | Chatterjee et al. | |
| 2006/0281111 A1 | 12/2006 | Muraca | |
| 2007/0077581 A1 | 4/2007 | Karin et al. | |
| 2010/0183633 A1 | 7/2010 | Davis et al. | |

FOREIGN PATENT DOCUMENTS

| | | |
|---|---|---|
| WO | WO 01/32653 | 5/2001 |
| WO | WO 01/85686 | 11/2001 |
| WO | WO 2007/027630 | 3/2007 |

OTHER PUBLICATIONS

Jaeschke et al., Proc. Nat'l. Acad. Sci., vol. 102, No. 19, pp. 6931-6935 (2005).*
Lund et al., J. Neurochem., vol. 92, pp. 1439-1451 (2005).*
Xu et al., Molec. & Cell. Biol., vol. 21, No. 14, pp. 4713-4724 (2001).*
Gallo et al., Nature Reviews: Molecular Cell Biology, vol. 3, pp. 663-672 (2002).*
Aguirre et al., J. Biol. Chem., vol. 277, No. 2, pp. 1531-1537 (2002).*
Xu et al., Molecular and Cellular Biology, vol. 21, No. 14, pp. 4713-4724 (2001).*
Lee et al., J. Biol. Chem., vol. 278, No. 5, pp. 2896-2902 (2003).*
Jaeschke et al., Proc. Nat'l., Acad. Sci., vol. 102, No. 19, pp. 6931-6935 (2005).*
Aguirre et al., "The c-Jun NH2-terminal kinase promotes insulin resistance during association with insulin receptor substrate-1 and phosphorylation of Ser307," J. Biol. Chem., 275:9047-54 (2000).
Aguirre et al., "Phosphorylation of Ser307 in insulin receptor substrate-1 blocks interactions with the insulin receptor and inhibits insulin action," J. Biol. Chem., 277:1531-37 (2002).
Arner, "Insulin resistance in type 2 diabetes: role of fatty acids," Diabetes Metab. Res. Rev., 18(Suppl. 2):S5-9 (2002).
Boden, "Effects of free fatty acids (FFA) on glucose metabolism: significance for insulin resistance and type 2 diabetes," Exp. Clin. Endocrinol. Diabetes, 111:121-124 (2003).
Boden, "Fatty acid-induced inflammation and insulin resistance in skeletal muscle and liver," Curr. Diab. Rep., 6:177-181 (2006).
Bogoyevitch et al., "Targeting the JNK MAPK cascade for inhibition: basic science and therapeutic potential," Biochim Biophys Acta., 1697:89-101 (2004).

(Continued)

*Primary Examiner* — Jane Zara
(74) *Attorney, Agent, or Firm* — Fish & Richardson P.C.

(57) ABSTRACT

Methods of treating metabolic stress disorders are disclosed that include administering to a subject a therapeutically effective amount of a composition that specifically inhibits the expression or activity of a mixed lineage kinase (MLK). Also disclosed are methods of identifying candidate compounds for treatment of metabolic stress disorders and methods of diagnosing metabolic stress disorders.

11 Claims, 17 Drawing Sheets

(56) References Cited

OTHER PUBLICATIONS

Brancho et al., "Mechanism of p38 MAP kinase activation in vivo," Genes Dev., 17:1969-78 (2003).
Brancho et al., "Role of MLK3 in the regulation of mitogen-activated protein kinase signaling cascades," Mol. Cell Biol., 25:3670-81 (2005).
Chin et al., "K252a induces cell cycle arrest and apoptosis by inhibiting Cdc2 and Cdc25c," Cancer Invest., 17:391-395 (1999).
Du et al., "Cdc42 induces activation loop phosphorylation and membrane targeting of mixed lineage kinase 3," J. Biol. Chem., 280:42984-93 (2005).
Gallo et al., "Mixed-lineage kinase control of JNK and p38 MAPK pathways," Nat. Rev. Mol. Cell. Biol., 3:663-672 (2002).
Gerber et al., "Protein 4.1B/differentially expressed in adenocarcinoma of the lung-1 functions as a growth suppressor in meningioma cells by activating Rac1-dependent c-Jun-NH2-kinase signaling," Cancer Res., 66:5295-5303 (2006).
Hirosumi et al., "A central role for JNK in obesity and insulin resistance," Nature, 420:333-336 (2002).
Hübner et al., "Oncogene addiction: role of signal attenuation," Dev Cell., 11:752-754 (2006).
Jaeschke and Davis, "Metabolic stress signaling mediated by mixed-lineage kinases," Mol. Cell, 27:498-508 (2007).
Jaeschke and Davis, "Chemical genetic analysis of signal transduction pathways," Expert Opin. Ther. Targets, 10:485-488 (2006).
Jaeschke et al., "An essential role of the JIP1 scaffold protein for JNK activation in adipose tissue," Genes Dev., 18:1976-80 (2004).
Jaeschke et al., "JNK2 is a positive regulator of the cJun transcription factor," Mol Cell., 23:899-911 (2006).
Jaeschke et al., "Disruption of the *Jnk2* (*Mapk9*) gene reduces destructive insulitis and diabetes in a mouse model of type I diabetes," Proc. Natl. Acad. Sci. USA, 102:6931-35 (2005).
Kahn et al., "Mechanisms linking obesity to insulin resistance and type 2 diabetes," Nature, 444:840-846 (2006).
Kim et al., "PKC-theta knockout mice are protected from fat-induced insulin resistance," J. Clin. Invest., 114:823-827 (2004).
Kovacs and Stumvoll, "Fatty acids and insulin resistance in muscle and liver," Best Pract. Res. Clin. Endocrinol. Metab., 19:625-635 (2005).
Lee et al., "c-Jun N-terminal kinase (JNK) mediates feedback inhibition of the insulin signaling cascade," J. Biol. Chem., 278:2896-2902 (2003).
Leitges et al., "Targeted disruption of the zetaPKC gene results in the impairment of the NF-kappaB pathway," Mol. Cell, 8:771-780 (2001).
Lund et al., "Inhibition of microglial inflammation by the MLK inhibitor CEP-1347," J. Neurochem., 92:1439-51 (2005).
Malhi et al., "Free fatty acids induce JNK-dependent hepatocyte lipoapoptosis," J. Biol. Chem., 281:12093-12101 (2006).
Maroney et al., "Motoneuron apoptosis is blocked by CEP-1347 (KT 7515), a novel inhibitor of the JNK signaling pathway," J. Neurosci., 18:104-111 (1998).
Murakata et al., "Mixed lineage kinase activity of indolocarbazole analogues," Bioorg. Med. Chem. Lett., 12:147-150 (2002).
Roux et al., "K252a and CEP1347 are neuroprotective compounds that inhibit mixed-lineage kinase-3 and induce activation of Akt and ERK," J. Biol. Chem., 277:49473-80 (2002).
Saporito et al., "Discovery of CEP-1347/KT-7515, an inhibitor of the JNK/SAPK pathway for the treatment of neurodegenerative diseases," Prog. Med. Chem., 40:23-62 (2002).
Schattenberg et al., "JNK1 but not JNK2 promotes the development of steatohepatitis in mice," Hepatology, 43:163-172 (2006).
Tournier et al., "MKK7 is an essential component of the JNK signal transduction pathway activated by proinflammatory cytokines," Genes Dev., 15:1419-26 (2001).
Vacratsis and Gallo, "Zipper-mediated oligomerization of the mixed lineage kinase SPRK/MLK-3 is not required for its activation by the GTPase cdc 42 but is necessary for its activation of the JNK pathway," J. Biol. Chem., 275:27893-27900 (2000).
Wang et al., "Mixed-lineage kinases: a target for the prevention of neurodegeneration," Annu. Rev. Pharmacol. Toxicol., 44:451-474 (2004).
Weston and Davis, "The JNK signal transduction pathway," Curr. Opin. Cell Biol., 19:142-149 (2007).
White, "Regulating insulin signaling and beta-cell function through IRS proteins," Can. J. Physiol. Pharmacol., 84:725-737 (2006).
Yasuda et al., "The JIP group of mitogen-activated protein kinase scaffold proteins," Mol. Cell. Biol., 19:7245-54 (1999).
International Search Report and Written Opinion issued in PCT/US2008/66350 on Oct. 20, 2008.
European Search Report; Application No. 08780783.0-2107; mailed Jun. 8, 2012; 11 pages.
Supplementary European Search Report; Application No. 08780783.0-2107; mailed Jun. 26, 2012; 1 page.
Waetzig and Herdegen, "Context-specific inhibition of JNKs: overcoming the dilemma of protection and damage," Trends in Pharmacological Sciences 26:455-461, 2005.

* cited by examiner

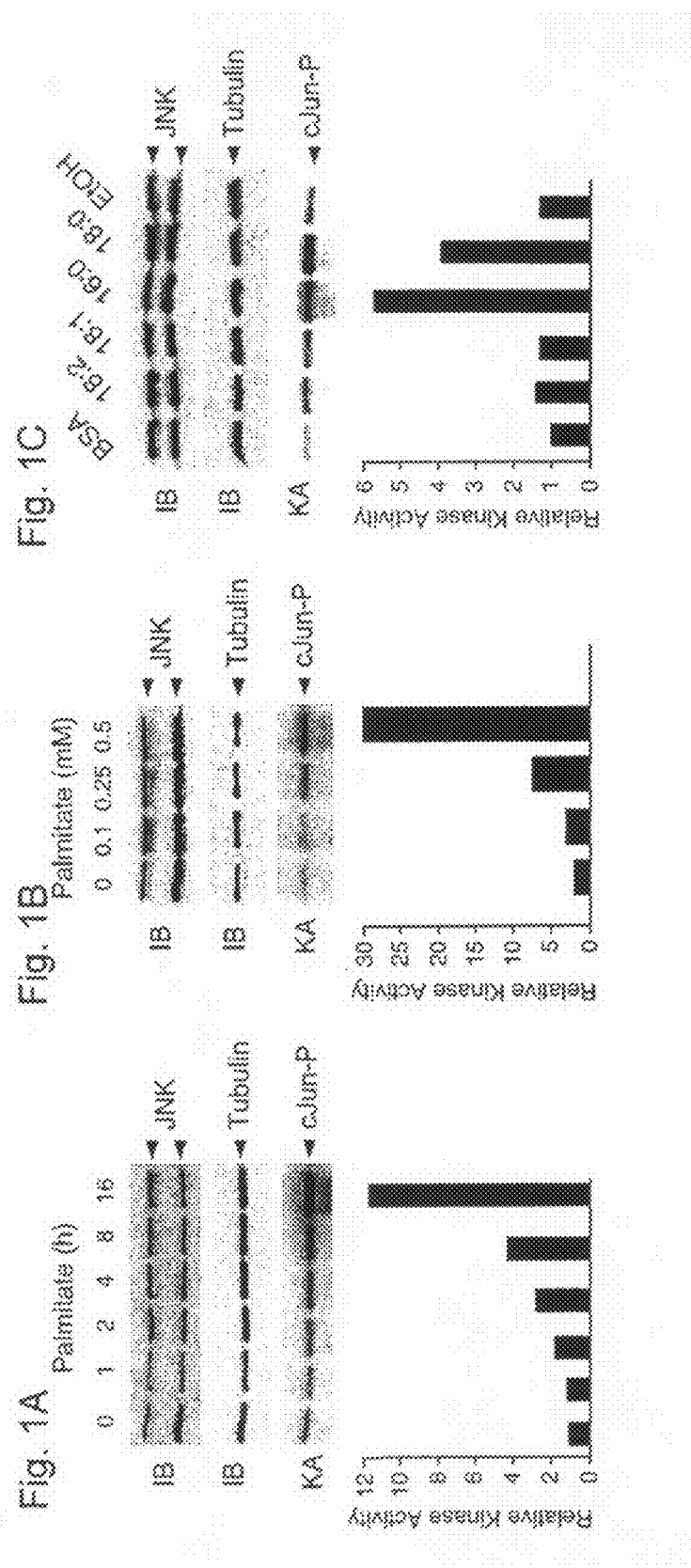

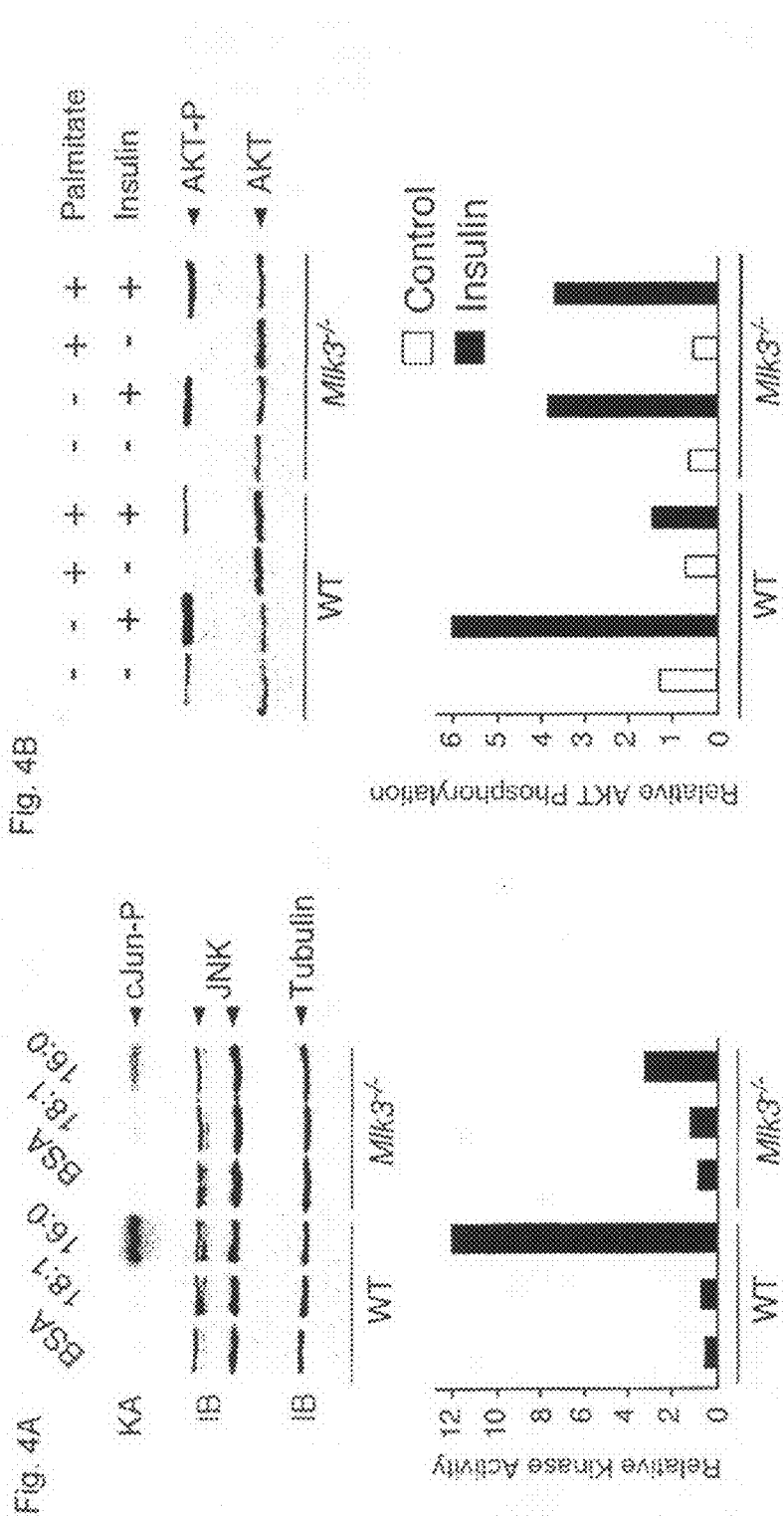

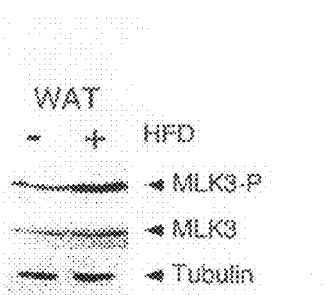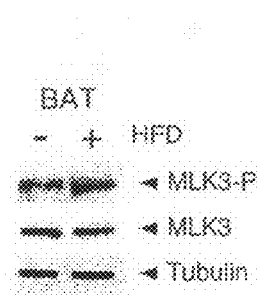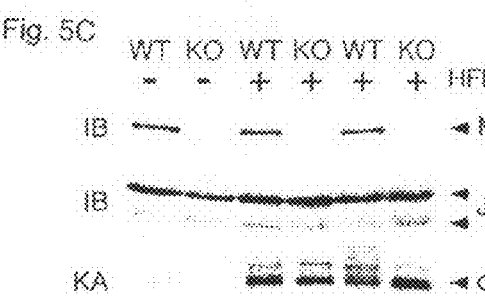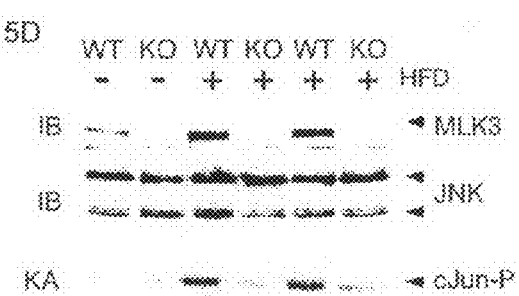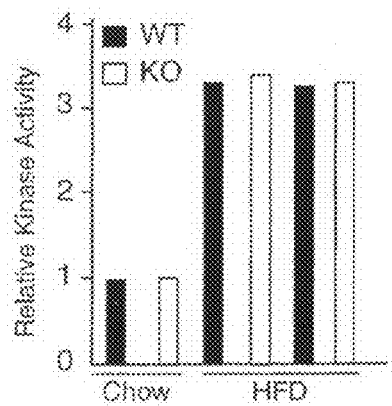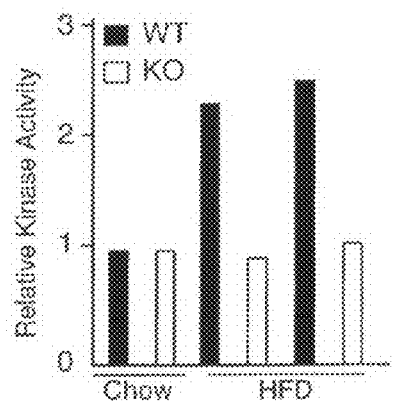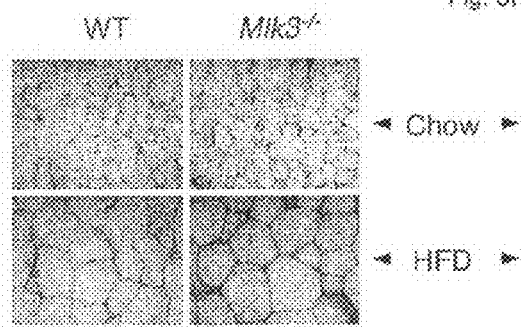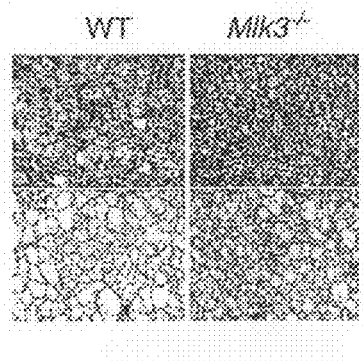

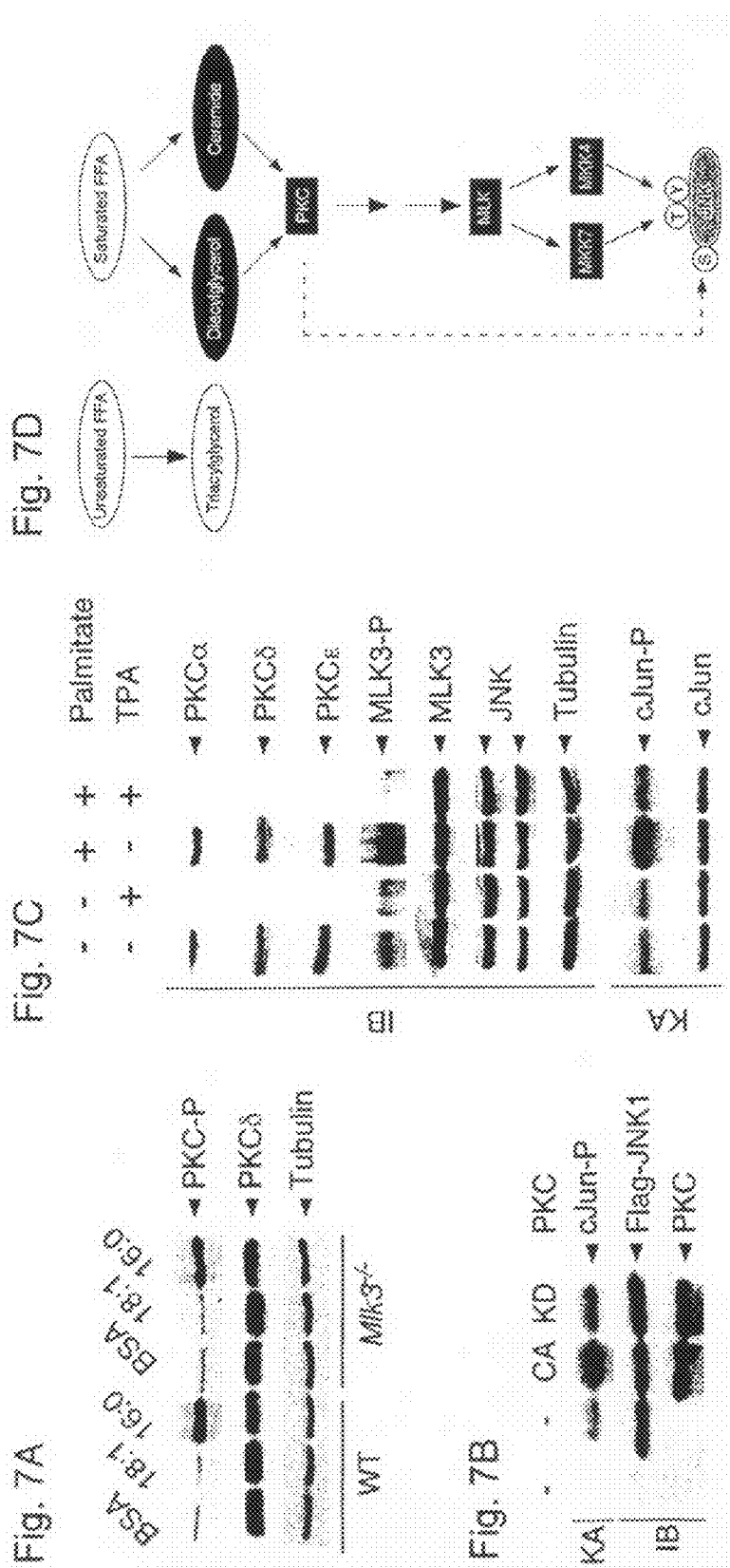

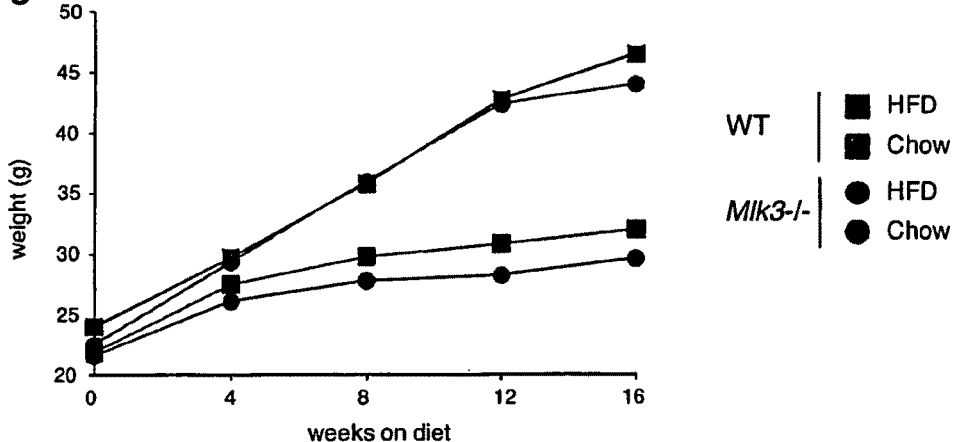
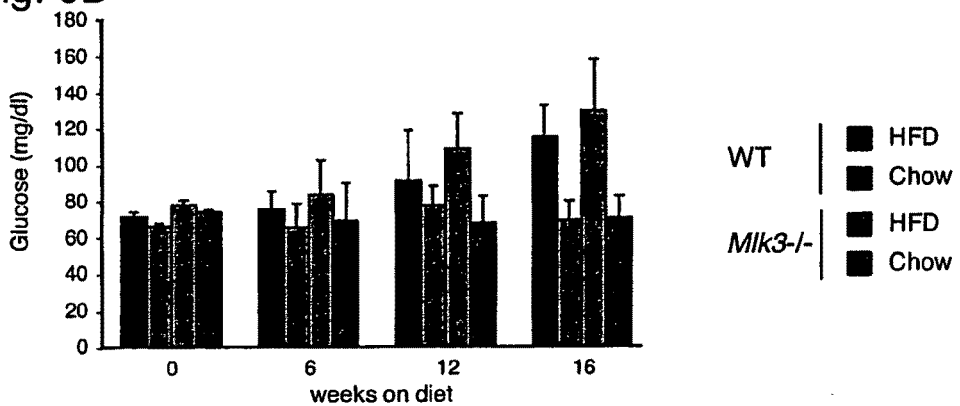
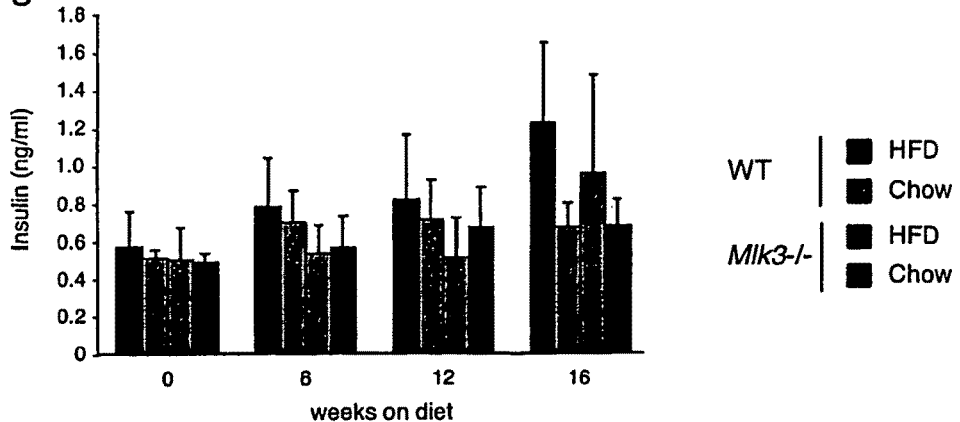

FIG. 10A

Human MLK1 coding sequence (SEQ ID NO:1; GenBank AY327900)

```
ATGGAGCCCTCCAGAGCGCTTCTCGGCTGCCTAGCGAGCGCCGCCGCTGCCGCCCCGCCGGGGGAGGATG
GAGCAGGGGCCGGGGCCGAGGAGGAGGAGGAGGAGGAGGAGGAGGCGGCGGCGGCGGTGGGCCCCGGGGA
GCTGGGCTGCGACGCGCCGCTGCCCTACTGGACGGCCGTGTTCGAGTACGAGGCGGCGGGCGAGGACGAG
CTGACCCTGCGGCTGGGCGACGTGGTGGAGGTGCTGTCCAAGGACTCGCAGGTGTCCGGCGACGAGGGCT
GGTGGACCGGGCAGCTGAACCAGCGGGTGGGCATCTTCCCCAGCAACTACGTGACCCCGCGCAGCGCCTT
CTCCAGCCGCTGCCAGCCCGGCGGCGAGGACCCCAGTTGCTACCCGCCCATTCAGTTGTTAGAAATTGAT
TTTGCGGAGCTCACCTTGGAAGAGATTATTGGCATCGGGGGCTTTGGGAAGGTCTATCGTGCTTTCTGGA
TAGGGGATGAGGTTGCTGTGAAAGCAGCTCGCCACGACCCTGATGAGGACATCAGCCAGACCATAGAGAA
TGTTCGCCAAGAGGCCAAGCTCTTCGCCATGCTGAAGCACCCCAACATCATTGCCCTAAGAGGGGTATGT
CTGAAGGAGCCCAACCTCTGCTTGGTCATGGAGTTTGCTCGTGGAGGACCTTTGAATAGAGTGTTATCTG
GGAAAAGGATTCCCCCAGACATCCTGGTGAATTGGGCTGTGCAGATTGCCAGAGGGATGAACTACTTACA
TGATGAGGCAATTGTTCCCATCATCCACCGCGACCTTAAGTCCAGCAACATATTGATCCTCCAGAAGGTG
GAGAATGGAGACCTGAGCAACAAGATTCTGAAGATCACTGATTTTGGCCTGGCTCGGGAATGGCACCGAA
CCACCAAGATGAGTGCGGCAGGGACGTATGCTTGGATGGCACCCGAAGTCATCCGGGCCTCCATGTTTTC
CAAAGGCAGTGATGTGTGGAGCTATGGGGTGCTACTTTGGGAGTTGCTGACTGGTGAGGTGCCCTTTCGA
GGCATTGATGGCTTAGCAGTCGCTTATGGAGTGGCCATGAACAAACTCGCCCTTCCTATTCCTTCTACGT
GCCCAGAACCTTTTGCCAAACTCATGGAAGACTGCTGGAATCCTGATCCCCACTCACGACCATCTTTCAC
GAATATCCTGGACCAGCTAACCACCATAGAGGAGTCTGGTTTCTTTGAAATGCCCAAGGACTCCTTCCAC
TGCCTGCAGGACAACTGGAAACACGAGATTCAGGAGACGTTTGACCAACTCAGGGCCAAAGAAAAGGAAC
TTCGCACCTGGGAGGAGGAGCTGACGCGGGCTGCACTGCAGCAGAAGAACCAGGAGGAACTGCTGCGGCG
TCGGGAGCAGGAGCTGGCCGAGCGGGAGATTGACATCCTGGAACGGGAGCTCAACATCATCATCCACCAG
CTGTGCCAGGAGAAGCCCCGGGTGAAGAAACGCAAGGGCAAGTTCAGGAAGAGCCGGCTGAAGCTCAAGG
ATGGCAACCGCATCAGCCTCCCTTCTGATTTCCAGCACAAGTTCACGGTGCAGGCCTCCCCTACCATGGA
TAAAAGGAAGAGTCTTATCAACAGCCGCTCCAGTCCTCCTGCAAGCCCCACCATCATTCCTCGCCTTCGA
GCCATCCAGTTGACACCAGGTGAAAGCAGCAAAACCTGGGGCAGGAGCTCAGTCGTCCCAAAGGAGGAAG
GGGAGGAGGAGGAGAAGAGGGCCCCAAAGAAGAAGGGACGGACGTGGGGGCCAGGGACGCTTGGTCAGAA
GGAGCTTGCCTCGGGAGATGAAGGATCCCCTCAGAGACGTGAGAAAGCTAATGGTTTAAGTACCCCATCA
GAATCTCCACATTTCCACTTGGGCCTCAAGTCCCTGGTAGATGGATATAAGCAGTGGTCGTCCAGTGCCC
CCAACCTGGTGAAGGGCCCAAGGAGTAGCCCGGCCCTGCCAGGGTTCACCAGCCTTATGGAGATGGAGGA
TGAGGACAGTGAAGGCCCAGGGAGTGGAGAGAGTCGCCTACAGCATTCACCCAGCCAGTCCTACCTCTGT
ATCCCATTCCCTCGTGGAGAGGATGGCGATGGCCCCTCCAGTGATGGAATCCATGAGGAGCCCACCCCAG
TCAACTCGGCCACGAGTACCCCTCAGCTGACGCCAACCAACAGCCTCAAGCGGGGCGGTGCCCACCACCG
CCGCTGCGAGGTGGCTCTGCTCGGCTGTGGGGCTGTTCTGGCAGCCACAGGCCTAGGGTTTGACTTGCTG
GAAGCTGGCAAGTGCCAGCTGCTTCCCCTGGAGGAGCCTGAGCCACCAGCCCGGGAGGAGAAGAAAAGAC
GGGAGGGTCTTTTTCAGAGGTCCAGCCGTCCTCGTCGGAGCACCAGCCCCCCATCCCGAAAGCTTTTCAA
GAAGGAGGAGCCCATGCTGTTGCTAGGAGACCCCTCTGCCTCCCTGACGCTGCTCTCCCTCTCCTCCATC
TCCGAGTGCAACTCCACACGCTCCCTGCTGCGCTCCGACAGCGATGAAATTGTCGTGTATGAGATGCCAG
TCAGCCCAGTCGAGGCCCCTCCCCTGAGTCCATGTACCCACAACCCCCTGGTCAATGTCCGAGTAGAGCG
CTTCAAACGAGATCCTAACCAATCTCTGACTCCCACCCATGTCACCCTCACCACCCCTCGCAGCCCAGC
AGTCACCGGCGGACTCCTTCTGATGGGGCCCTTAAGCCAGAGACTCTCCTAGCCAGCAGGAGCCCCTCCA
GCAATGGGTTGAGCCCCAGTCCTGGAGCAGGAATGTTGAAAACCCCAGTCCCAGCCGAGACCCAGGTGA
ATTCCCCCGTCTCCCTGACCCCAATGTGGTCTTCCCCCAACCCCAAGGCGCTGGAACACTCAGCAGGAC
TCTACCTTGGAGAGACCCAAGACTCTGGAGTTTCTGCCTCGGCCGCGTCCTTCTGCCAACCGGCAACGGC
TGGACCCTTGGTGGTTTGTGTCCCCAGCCATGCCCGCAGCACCTCCCCAGCCAACAGCTCCAGCACAGA
GACGCCCAGCAACCTGGACTCCTGCTTTGCTAGCAGTAGCAGCACTGTAGAGGAGCGGCCTGGACTTCCA
GCCCTGCTCCCGTTCCAGGCAGGGCCGCTGCCCCCGACTGAGCGGACGCTCCTGGACCTGGATGCAGAGG
GGCAGAGTCAGGACAGCACCGTGCCGCTGTGCAGAGCGGAACTGAACACACACAGGCCTGCCCCTTATGA
GATCCAGCAGGAGTTCTGGTCTTAG
```

FIG. 10B

Human MLK1 polypeptide sequence (SEQ ID NO:2; GenBank AAQ23054)

MEPSRALLGCLASAAAAAPPGEDGAGAGAEEEEEEEEEAAAAVGPGELGCDAPLPYWTAVFEYEAAGEDE
LTLRLGDVVEVLSKDSQVSGDEGWWTGQLNQRVGIFPSNYVTPRSAFSSRCQPGGEDPSCYPPIQLLEID
FAELTLEEIIGIGGFGKVYRAFWIGDEVAVKAARHDPDEDISQTIENVRQEAKLFAMLKHPNIIALRGVC
LKEPNLCLVMEFARGGPLNRVLSGKRIPPDILVNWAVQIARGMNYLHDEAIVPIIHRDLKSSNILILQKV
ENGDLSNKILKITDFGLAREWHRTTKMSAAGTYAWMAPEVIRASMFSKGSDVWSYGVLLWELLTGEVPFR
GIDGLAVAYGVAMNKLALPIPSTCPEPFAKLMEDCWNPDPHSRPSFTNILDQLTTIEESGFFEMPKDSFH
CLQDNWKHEIQETFDQLRAKEKELRTWEEELTRAALQQKNQEELLRRREQELAEREIDILERELNIIIHQ
LCQEKPRVKKRKGKFRKSRLKLKDGNRISLPSDFQHKFTVQASPTMDKRKSLINSRSSPPASPTIIPRLR
AIQLTPGESSKTWGRSSVVPKEEGEEEEKRAPKKKGRTWGPGTLGQKELASGDEGSPQRREKANGLSTPS
ESPHFHLGLKSLVDGYKQWSSSAPNLVKGPRSSPALPGFTSLMEMEDEDSEGPGSGESRLQHSPSQSYLC
IPFPRGEDGDGPSSDGIHEEPTPVNSATSTPQLTPTNSLKRGGAHHRRCEVALLGCGAVLAATGLGFDLL
EAGKCQLLPLEEPEPPAREEKKRREGLFQRSSRPRRSTSPPSRKLFKKEEPMLLLGDPSASLTLLSLSSI
SECNSTRSLLRSDSDEIVVYEMPVSPVEAPPLSPCTHNPLVNVRVERFKRDPNQSLTPTHVTLTTPSQPS
SHRRTPSDGALKPETLLASRSPSSNGLSPSPGAGMLKTPSPSRDPGEFPRLPDPNVVFPPTPRRWNTQQD
STLERPKTLEFLPRPRPSANRQRLDPWWFVSPSHARSTSPANSSSTETPSNLDSCFASSSSTVEERPGLP
ALLPFQAGPLPPTERTLLDLDAEGQSQDSTVPLCRAELNTHRPAPYEIQQEFWS

FIG. 10C

Human MLK2 coding sequence (SEQ ID NO:3; GenBank NM_002446)

```
ATGGAGGAGGAGGAGGGGCGGTGGCCAAGGAGTGGGGCACGACCCCCGCGGGGCCCGTCTGGACCGCGG
TGTTCGACTACGAGGCGGCGGGCGACGAGGAGCTGACCCTGCGGAGGGGCGATCGCGTCCAGGTGCTTTC
CCAAGACTGTGCGGTGTCCGGCGACGAGGGCTGGTGGACCGGGCAGCTCCCCAGCGGCCGCGTGGGCGTC
TTCCCCAGCAACTACGTGGCCCCCGGCGCCCCCGCTGCACCCGCGGGCCTCCAGCTGCCCCAGGAGATCC
CCTTCCACGAGCTGCAGCTAGAGGAGATCATCGGTGTGGGGGGCTTTGGCAAGGTCTATCGGGCCCTGTG
GCGTGGCGAGGAGGTGGCAGTCAAGGCCGCCCGGCTGGACCCTGAGAAGGACCCGGCAGTGACAGCGGAG
CAGGTGTGCCAGGAAGCCCGGCTCTTTGGAGCCCTGCAGCACCCCAACATAATTGCCCTTAGGGCGCCT
GCCTCAACCCCCCACACCTCTGCCTAGTGATGGAGTATGCCCGGGGTGGTGCACTGAGCAGGGTGCTGGC
AGGTCGCCGGGTGCCACCTCACGTGCTGGTCAACTGGGCTGTGCAGGTGGCCCGGGGCATGAACTACCTA
CACAATGATGCCCCTGTGCCCATCATCCACCGGGACCTCAAGTCCATCAACATCCTGATCCTGGAGGCCA
TCGAGAACCACAACCTCGCAGACACGGTGCTCAAGATCACGGACTTCGGCCTCGCCCGCGAGTGGCACAA
GACCACCAAGATGAGCGCTGCGGGGACCTACGCCTGGATGGCGCCGGAGGTTATCCGTCTCTCCCTCTTC
TCCAAAAGCAGTGATGTCTGGAGCTTCGGGGTGCTGCTGTGGGAGCTGCTGACGGGGGAGGTCCCCTACC
GTGAGATCGACGCCTTGGCCGTGGCGTATGGCGTGGCTATGAATAAGCTGACGCTGCCCATTCCCTCCAC
GTGCCCCGAGCCCTTTGCCCGCCTCCTGGAGGAATGCTGGGACCCAGACCCCCACGGGCGGCCAGATTTC
GGTAGCATCTTGAAGCGGCTTGAAGTCATCGAACAGTCAGCCCTGTTCCAGATGCCACTGGAGTCCTTCC
ACTCGCTGCAGGAAGACTGGAAGCTGGAGATTCAGCACATGTTTGATGACCTTCGGACCAAGGAGAAGGA
GCTTCGGAGCCGTGAGGAGGAGCTGCTGCGGGCGGCACAGGAGCAGCGCTTCCAGGAGGAGCAGCTGCGG
CGGCGGGAGCAGGAGCTGGCAGAACGTGAGATGGACATCGTGGAACGGGAGCTGCACCTGCTCATGTGCC
AGCTGAGCCAGGAGAAGCCCCGGGTCCGCAAGCGCAAGGGCAACTTCAAGCGCAGCCGCCTGCTCAAGCT
GCGGGAAGGCGGCAGCCACATCAGCCTGCCCTCTGGCTTTGAGCATAAGATCACAGTCCAGGCCTCTCCA
ACTCTGGATAAGCGGAAAGGATCCGATGGGGCCAGCCCCCTGCAAGCCCCAGCATCATCCCCCGGCTGA
GGGCCATTCGCCTGACTCCCGTGGACTGTGGTGGCAGCAGCAGTGGCAGCAGCAGTGGAGGAAGTGGGAC
ATGGAGCCGCGGTGGGCCCCCAAAGAAGGAAGAACTGGTCGGGGGCAAGAAGAAGGGACGAACGTGGGGG
CCCAGCTCCACCCTGCAGAAGGAGCGGGTGGGAGGAGAGGAGAGGCTGAAGGGGCTGGGGAAGGAAGCA
AACAGTGGTCATCAAGTGCCCCCAACCTGGGCAAGTCCCCCAAACACACACCCATCGCCCCTGGCTTCGC
CAGCCTCAATGAGATGGAGGAGTTCGCGGAGGCAGAGGATGGAGGCAGCAGCGTGCCCCCTTCCCCCTAC
TCGACCCCGTCCTACCTCTCAGTGCCACTGCCTGCCGAGCCCTCCCCGGGGGCGCGGGCGCCGTGGGAGC
CGACGCCGTCCGCGCCCCCCGCTCGGTGGGGACACGGCGCCCGGCGGCGCTGCGACCTGGCGCTGCTAGG
CTGCGCCACGCTGCTGGGGCTGTGGGCCTGGGCGCCGACGTGGCCGAGGCGCGCGCGGCCGACGGTGAG
GAGCAGCGGCGCTGGCTCGACGGGCCTCTTCTTTCCCCGCGCCGGCCGCTTCCCGCGGGGCCTCAGCCCAC
CCGCGCGTCCCCACGGCCGCCGCGAAGACGTGGCCCCGGCCTGGGCCTGGCGCCCTCGGCCACCCTCGT
GTCGCTGTCGTCCGTGTCCGACTGCAACTCCACGCGTTCACTGCTGCGCTCTGACAGTGACGAGGCCGCA
CCGGCCGCGCCCTCCCCACCACCCTCCCCGCCCGCGCCCACACCCACGCCCTCGCCCAGCACCAACCCCC
TGGTGGACCTGGAGCTGGAGAGCTTCAAGAAGGACCCCGCCAGTCGCTCACGCCCACCCACGTCACGGC
TGCATGCGCTGTGAGCCGCGGGCACCGGCGGACGCCATCGGATGGGCGCTGGGGCAGCGGGGGCCGCCC
GAGCCCGCGGGCCATGGCCCTGGCCCTCGTGACCTTCTGGACTTCCCCCGCCTGCCCGACCCCCAGGCCC
TGTTCCCAGCCCGCCGCCGGCCCCCTGAGTTCCCAGGCCGCCCCACCACCCTGACCTTTGCCCCGAGACC
TCGGCCGGCTGCCAGTCGCCCCGCTTGGACCCCTGGAAACTGGTCTCCTTCGGCCGGACACTCACCATC
TCGCCTCCCAGCAGGCCAGACACTCCGGAGAGCCCTGGGCCCCCAGCGTGCAGCCCACACTGCTGGACA
TGGACATGGAGGGGCAGAACCAAGACAGCACAGTGCCCCTGTGCGGGGCCCACGGCTCCCACTAA
```

FIG. 10D

Human MLK2 polypeptide sequence (SEQ ID NO:4; GenBank NP_002437)

MEEEEGAVAKEWGTTPAGPVWTAVFDYEAAGDEELTLRRGDRVQVLSQDCAVSGDEGWWTGQLPSGRVGV
FPSNYVAPGAPAAPAGLQLPQEIPFHELQLEEIIGVGGFGKVYRALWRGEEVAVKAARLDPEKDPAVTAE
QVCQEARLFGALQHPNIIALRGACLNPPHLCLVMEYARGGALSRVLAGRRVPPHVLVNWAVQVARGMNYL
HNDAPVPIIHRDLKSINILILEAIENHNLADTVLKITDFGLAREWHKTTKMSAAGTYAWMAPEVIRLSLF
SKSSDVWSFGVLLWELLTGEVPYREIDALAVAYGVAMNKLTLPIPSTCPEPFARLLEECWDPDPHGRPDF
GSILKRLEVIEQSALFQMPLESFHSLQEDWKLEIQHMFDDLRTKEKELRSREEELLRAAQEQRFQEEQLR
RREQELAEREMDIVERELHLLMCQLSQEKPRVRKRKGNFKRSRLLKLREGGSHISLPSGFEHKITVQASP
TLDKRKGSDGASPPASPSIIPRLRAIRLTPVDCGGSSGSSSGGSGTWSRGGPPKKEELVGGKKKGRTWG
PSSTLQKERVGGEERLKGLGEGSKQWSSSAPNLGKSPKHTPIAPGFASLNEMEEFAEAEDGGSSVPPSPY
STPSYLSVPLPAEPSPGARAPWEPTPSAPPARWGHGARRRCDLALLGCATLLGAVGLGADVAEARAADGE
EQRRWLDGLFFPRAGRFPRGLSPPARPHGRREDVGPGLGLAPSATLVSLSSVSDCNSTRSLLRSDSDEAA
PAAPSPPPSPPAPTPTPSPSTNPLVDLELESFKKDPRQSLTPTHVTAACAVSRGHRRTPSDGALGQRGPP
EPAGHGPGPRDLLDFPRLPDPQALFPARRRPPEFPGRPTTLTFAPRPRPAASRPRLDPWKLVSFGRTLTI
SPPSRPDTPESPGPPSVQPTLLDMDMEGQNQDSTVPLCGAHGSH

FIG. 10E

Human MLK3 coding sequence (SEQ ID NO:5; GenBank NM_002419)

```
ATGGAGCCCTTGAAGAGCCTCTTCCTCAAGAGCCCTCTAGGGTCATGGAATGGCAGTGGCAGCGGGGGTG
GTGGGGGCGGTGGAGGAGGCCGGCCTGAGGGGTCTCCAAAGGCAGCGGGTTATGCCAACCCGGTGTGGAC
AGCCCTGTTCGACTACGAGCCCAGTGGGCAGGATGAGCTGGCCCTGAGGAAGGGTGACCGTGTGGAGGTG
CTGTCCCGGGACGCAGCCATCTCAGGAGACGAGGGCTGGTGGGCGGGCCAGGTGGGTGGCCAGGTGGGCA
TCTTCCCGTCCAACTATGTGTCTCGGGGTGGCGGCCCGCCCCCCTGCGAGGTGGCCAGCTTCCAGGAGCT
GCGGCTGGAGGAGGTGATCGGCATTGGAGGCTTTGGCAAGGTGTACAGGGGCAGCTGGCGAGGTGAGCTG
GTGGCTGTGAAGGCAGCTCGCCAGGACCCCGATGAGGACATCAGTGTGACAGCCGAGAGCGTTCGCCAGG
AGGCCCGGCTCTTCGCCATGCTGGCACACCCCAACATCATTGCCCTCAAGGCTGTGTGCCTGGAGGAGCC
CAACCTGTGCCTGGTGATGGAGTATGCAGCCGGTGGGCCCCTCAGCCGAGCTCTGGCCGGGCGGCGCGTG
CCTCCCCATGTGCTGGTCAACTGGGCTGTGCAGATTGCCCGTGGGATGCACTACCTGCACTGCGAGGCCC
TGGTGCCCGTCATCCACCGTGATCTCAAGTCCAACAACATTTTGCTGCTGCAGCCCATTGAGAGTGACGA
CATGGAGCACAAGACCCTGAAGATCACCGACTTTGGCCTGGCCCGAGAGTGGCACAAAACCACACAAATG
AGTGCCGCGGGCACCTACGCCTGGATGGCTCCTGAGGTTATCAAGGCCTCCACCTTCTCTAAGGGCAGTG
ACGTCTGGAGTTTTGGGGTGCTGCTGTGGGAACTGCTGACCGGGGAGGTGCCATACCGTGGCATTGACTG
CCTTGCTGTGGCCTATGGCGTAGCTGTTAACAAGCTCACACTGCCCATCCCATCCACCTGCCCCGAGCCC
TTCGCACAGCTTATGGCCGACTGCTGGGCGCAGGACCCCCACCGCAGGCCCGACTTCGCCTCCATCCTGC
AGCAGTTGGAGGCGCTGGAGGCACAGGTCCTACGGGAAATGCCGCGGGACTCCTTCCATTCCATGCAGGA
AGGCTGGAAGCGCGAGATCCAGGGTCTCTTCGACGAGCTGCGAGCCAAGGAAAAGGAACTACTGAGCCGC
GAGGAGGAGCTGACGCGAGCGGCGCGCGAGCAGCGGTCACAGGCGGAGCAGCTGCGGCGGCGCGAGCACC
TGCTGGCCCAGTGGGAGCTAGAGGTGTTCGAGCGCGAGCTGACGCTGCTGCTGCAGCAGGTGGACCGCGA
GCGACCGCACGTGCGCCGCCGCCGCGGGACATTCAAGCGCAGCAAGCTCCGGGCGCGCGACGGCGGCGAG
CGTATCAGCATGCCACTCGACTTCAAGCACCGCATCACCGTGCAGGCCTCACCCGGCCTTGACCGGAGGA
GAAACGTCTTCGAGGTCGGGCCTGGGGATTCGCCCACCTTTCCCCGGTTCCGAGCCATCCAGTTGGAGCC
TGCAGAGCCAGGCCAGGCATGGGGCCGCCAGTCCCCCCGACGTCTGGAGGACTCAAGCAATGGAGAGCGG
CGAGCATGCTGGGCTTGGGGTCCCAGTTCCCCAAGCCTGGGGAAGCCCAGAATGGGAGGAGAAGGTCCC
GCATGGACGAAGCCACATGGTACCTGGATTCAGATGACTCATCCCCCTTAGGATCTCCTTCCACACCCCC
AGCACTCAATGGTAACCCCCGCGGCCTAGCCTGGAGCCCGAGGAGCCCAAGAGGCCTGTCCCCGCAGAG
CGCGGTAGCAGCTCTGGGACGCCCAAGCTGATCCAGCGGGCGCTGCTGCGGCACCGCCCTGCTCGCCT
CGCTGGGCCTTGGCCGCGACCTGCAGCCGCGCGGGAGGCCCAGGACGCGAGCGCGGGGAGTCCCCGACAAC
ACCCCCCACGCCAACGCCCGCGCCCTGCCCGACCGAGCCGCCCCCTTCCCCGCTCATCTGCTTCTCGCTC
AAGACGCCCGACTCCCCGCCCACTCCTGCACCCCTGTTGCTGGACCTGGGTATCCCTGTGGGCCAGCGGT
CAGCCAAGAGCCCCGACGTGAGGAGGAGCCCCGCGGAGGCACTGTCTCACCCCCACCGGGGACATCACG
CTCTGCTCCTGGCACCCCAGGCACCCCACGTTCACCACCCCTGGGCCTCATCAGCCGACCTCGGCCCTCG
CCCCTTCGCAGCCGCATTGATCCCTGGAGCTTTGTGTCAGCTGGGCCACGGCCTTCTCCCCTGCCATCAC
CACAGCCTGCACCCCGCCGAGCACCCTGGACCTTGTTCCCGGACTCAGACCCCTTCTGGGACTCCCCACC
TGCCAACCCCTTCCAGGGGGGCCCCAGGACTGCAGGGCACAGACCAAAGACATGGGTGCCCAGGCCCCG
TGGGTGCCGGAAGCGGGGCCTTGA
```

FIG. 10F

Human MLK3 polypeptide sequence (SEQ ID NO:6; GenBank NP_002410)

MEPLKSLFLKSPLGSWNGSGSGGGGGGGGGRPEGSPKAAGYANPVWTALFDYEPSGQDELALRKGDRVEV
LSRDAAISGDEGWWAGQVGGQVGIFPSNYVSRGGGPPPCEVASFQELRLEEVIGIGGFGKVYRGSWRGEL
VAVKAARQDPDEDISVTAESVRQEARLFAMLAHPNIIALKAVCLEEPNLCLVMEYAAGGPLSRALAGRRV
PPHVLVNWAVQIARGMHYLHCEALVPVIHRDLKSNNILLLQPIESDDMEHKTLKITDFGLAREWHKTTQM
SAAGTYAWMAPEVIKASTFSKGSDVWSFGVLLWELLTGEVPYRGIDCLAVAYGVAVNKLTLPIPSTCPEP
FAQLMADCWAQDPHRRPDFASILQQLEALEAQVLREMPRDSFHSMQEGWKREIQGLFDELRAKEKELLSR
EEELTRAAREQRSQAEQLRRREHLLAQWELEVFERELTLLLQQVDRERPHVRRRRGTFKRSKLRARDGGE
RISMPLDFKHRITVQASPGLDRRRNVFEVGPGDSPTFPRFRAIQLEPAEPGQAWGRQSPRRLEDSSNGER
RACWAWGPSSPKPGEAQNGRRRSRMDEATWYLDSDDSSPLGSPSTPPALNGNPPRPSLEPEEPKRPVPAE
RGSSSGTPKLIQRALLRGTALLASLGLGRDLQPPGGPGRERGESPTTPPTPTPAPCPTEPPPSPLICFSL
KTPDSPPTPAPLLLDLGIPVGQRSAKSPRREEEPRGGTVSPPPGTSRSAPGTPGTPRSPPLGLISRPRPS
PLRSRIDPWSFVSAGPRPSPLPSPQPAPRRAPWTLFPDSDPFWDSPPANPFQGGPQDCRAQTKDMGAQAP
WVPEAGP

FIG. 10G

Human MLK4 coding sequence (SEQ ID NO:7; GenBank NM_032435)

ATGGCTTTGCGGGGCGCCGCGGGAGCGACCGACACCCCGGTGTCCTCGGCCGGGGGAGCCCCCGGCGGCT
CAGCGTCCTCGTCGTCCACCTCCTCGGGCGGCTCGGCCTCGGCGGGCGCGGGGCTGTGGGCCGCGCTCTA
TGACTACGAGGCTCGCGGCGAGGACGAGCTGAGCCTGCGGCGCGGCCAGCTGGTGGAGGTGTTGTCGCAG
GACGCCGCCGTGTCGGGCGACGAGGGCTGGTGGGCAGGCCAGGTGCAGCGGCGCCTCGGCATCTTCCCCG
CCAACTACGTGGCTCCCTGCCGCCCGGCCGCCAGCCCCGCGCCGCCGCCCTCGCGGCCCAGCTCCCCGGT
ACACGTCGCCTTCGAGCGGCTGGAGCTGAAGGAGCTCATCGGCGCTGGGGGCTTCGGGCAGGTGTACCGC
GCCACCTGGCAGGGCCAGGAGGTGGCCGTGAAGGCGGCGCGCCAGGACCCGGAGCAGGACGCGGCGGCGG
CTGCCGAGAGCGTGCGGCGCGAGGCTCGGCTCTTCGCCATGCTGCGGCACCCCAACATCATCGAGCTGCG
CGGCGTGTGCCTGCAGCAGCCGCACCTCTGCCTGGTGCTGGAGTTCGCCCGCGGCGGAGCGCTCAACCGA
GCGCTGGCCGCTGCCAACGCCGCCCCGGACCCGCGCGCGCCCGGCCCCGCCGCGCGCCGCATCCCTC
CGCACGTGCTGGTCAACTGGGCCGTGCAGATAGCGCGGGCATGCTCTACCTGCATGAGGAGGCCTTCGT
GCCCATCCTGCACCGGGACCTCAAGTCCAGCAACATTTTGCTACTTGAAGAGATAGAACATGATGACATC
TGCAATAAAACTTTGAAGATTACAGATTTTGGGTTGGCGAGGGAATGGCACAGGACCACCAAAATGAGCA
CAGCAGGCACCTATGCCTGGATGGCCCCCGAAGTGATCAAGTCTTCCTTGTTTTCTAAGGGAAGCGACAT
CTGGAGCTGTGGAGTGCTGCTGTGGGAACTGCTCACCGGAGAAGTCCCCTATCGGGGCATTGATGGCCTC
GCCGTGGCTTATGGGGTAGCAGTCAATAAACTCACTTTGCCCATTCCATCCACCTGCCCTGAGCCGTTTG
CCAAGCTCATGAAAGAATGCTGGCAACAAGACCCTCATATTCGTCCATCGTTTGCCTTAATTCTCGAACA
GTTGACTGCTATTGAGGGGCAGTGATGACTGAGATGCCTCAAGAATCTTTTCATTCCATGCAAGATGAC
TGGAAACTAGAAATTCAACAAATGTTTGATGAGTTGAGAACAAAGGAAAAGGAGCTGCGATCCCGGGAAG
AGGAGCTGACTCGGGCGGCTCTGCAGCAGAAGTCTCAGGAGGAGCTGCTAAAGCGGCGTGAGCAGCAGCT
GGCAGAGCGCGAGATCGACGTGCTGGAGCGGGAACTTAACATTCTGATATTCCAGCTAAACCAGGAGAAG
CCCAAGGTAAAGAAGAGGAAGGGCAAGTTTAAGAGAAGTCGTTTAAAGCTCAAAGATGGACATCGAATCA
GTTTACCTTCAGATTTCCAGCACAAGATAACCGTGCAGGCCTCTCCCAACTTGGACAAACGGCGGAGCCT
GAACAGCAGCAGTTCCAGTCCCCCGAGCAGCCCCACAATGATGCCCCGACTCCGAGCCATACAGTTGACT
TCAGATGAAAGCAATAAAACTTGGGGAAGGAACACAGTCTTTCGACAAGAAGAATTTGAGGATGTAAAAA
GGAATTTTAAGAAAAAAGGTTGTACCTGGGGACCAAATTCCATTCAAATGAAAGATAGAACAGATTGCAA
AGAAAGGATAAGACCTCTCTCCGATGGCAACAGTCCTTGGTCAACTATCTTAATAAAAAATCAGAAAACC
ATGCCCTTGGCTTCATTGTTTGTGGACCAGCCAGGGTCCTGTGAAGAGCCAAAACTTTCCCCTGATGGAT
TAGAACACAGAAAACCAAAACAAATAAAATTGCCTAGTCAGGCCTACATTGATCTACCTCTTGGGAAAGA
TGCTCAGAGAGAGAATCCTGCAGAAGCTGGAAGCTGGGAGGAGGCAGCCTCTGCGAATGCTGCCACAGTC
ACCATTGAGATGGCTCCTACGAATAGTCTGAGTAGATCCCCCCAGAGAAAGAAAACGGAGTCAGCTCTGT
ATGGGTGCACCGTCCTTCTGGCATCGGTGGCTCTGGGACTGGACCTCAGAGAGCTTCATAAAGCACAGGC
TGCTGAAGAACCGTTGCCCAAGGAAGAGAAGAAGAAACGAGAGGGAATCTTCCAGCGGGCTTCCAAGTCC
CGCAGAAGCGCCAGTCCTCCCACAAGCCTGTCATCCACCTGTGGGGAGGCCAGCAGCCCACCCTCCCTGC
CACTGTCAAGTGCCCTGGGCATCCTCTCCACACCTTCTTTCTCCACAAAGTGCCTGCTGCAGATGGACAG
TGAAGATCCACTGGTGGACAGTGCACCTGTCACTTGTGACTCTGAGATGCTCACTCCGGATTTTTGTCCC
ACTGCCCCAGGAAGTGGTCGTGAGCCAGCCCTCATGCCAAGACTTGACACTGATTGTAGTGTATCAAGAA
ACTTGCCGTCTTCCTTCCTACAGCGGACATGTGGGAATGTACCTTACTGTGCTTCTTCAAAACATAGACC
ATCACATCACAGACGGACCATGTCTGATGGAAATCCGACCCCAACTGGTGCAACTATTATCTCAGCCACT
GGAGCCTCTGCACTGCCACTCTGCCCCTCACCTGCTCCTCACAGTCATCTGCCAAGGGAGGTCTCACCCA
AGAAGCACAGCACTGTCCACATCGTGCCTCAGCGTCGCCCTGCCTCCCTGAGAAGCCGCTCAGATCTGCC
TCAGGCTTACCCACAGACAGCAGTGTCTCAGCTGGCACAGACTGCCTGTGTAGTGGGTCGCCCAGGACCA
CATCCCACCCAATTCCTCGCTGCCAAGGAGAGAACTAAATCCCATGTGCCTTCATTACTGGATGTTGACG
TGGAAGGTCAGAGCAGGGACTACACTGTGCCACTGGGTAGAATGAGGAGCAAAACCAGCCGGCCATCTAT
ATATGAACTGGAGAAAGAATTCCTGTCTTAA

FIG. 10H

Human MLK4 polypeptide sequence (SEQ ID NO:8; GenBank NP_115811)

```
MALRGAAGATDTPVSSAGGAPGGSASSSSTSSGGSASAGAGLWAALYDYEARGEDELSLRRGQLVEVLSQ
DAAVSGDEGWWAGQVQRRLGIFPANYVAPCRPAASPAPPPSRPSSPVHVAFERLELKELIGAGGFGQVYR
ATWQGQEVAVKAARQDPEQDAAAAAESVRREARLFAMLRHPNIIELRGVCLQQPHLCLVLEFARGGALNR
ALAAANAAPDPRAPGPRRARRIPPHVLVNWAVQIARGMLYLHEEAFVPILHRDLKSSNILLLEEIEHDDI
CNKTLKITDFGLAREWHRTTKMSTAGTYAWMAPEVIKSSLFSKGSDIWSCGVLLWELLTGEVPYRGIDGL
AVAYGVAVNKLTLPIPSTCPEPFAKLMKECWQQDPHIRPSFALILEQLTAIEGAVMTEMPQESFHSMQDD
WKLEIQQMFDELRTKEKELRSREEELTRAALQQKSQEELLKRREQQLAEREIDVLERELNILIFQLNQEK
PKVKKRKGKFKRSRLKLKDGHRISLPSDFQHKITVQASPNLDKRRSLNSSSSSPPSSPTMMPRLRAIQLT
SDESNKTWGRNTVFRQEEFEDVKRNFKKKGCTWGPNSIQMKDRTDCKERIRPLSDGNSPWSTILIKNQKT
MPLASLFVDQPGSCEEPKLSPDGLEHRKPKQIKLPSQAYIDLPLGKDAQRENPAEAGSWEEAASANAATV
TIEMAPTNSLSRSPQRKKTESALYGCTVLLASVALGLDLRELHKAQAAEEPLPKEEKKKREGIFQRASKS
RRSASPPTSLSSTCGEASSPPSLPLSSALGILSTPSFSTKCLLQMDSEDPLVDSAPVTCDSEMLTPDFCP
TAPGSGREPALMPRLDTDCSVSRNLPSSFLQRTCGNVPYCASSKHRPSHHRRTMSDGNPTPTGATIISAT
GASALPLCPSPAPHSHLPREVSPKKHSTVHIVPQRRPASLRSRSDLPQAYPQTAVSQLAQTACVVGRPGP
HPTQFLAAKERTKSHVPSLLDVDVEGQSRDYTVPLGRMRSKTSRPSIYELEKEFLS
```

MIXED LINEAGE KINASES AND METABOLIC DISORDERS

CROSS-REFERENCE TO RELATED APPLICATIONS

This application is the U.S. national stage under 35 USC §371 of International Application Number PCT/US2008/066350, filed on Jun. 9, 2008, which claims the benefit under 35 USC §119(e) to U.S. Provisional Patent Application Ser. No. 60/933,799, filed on Jun. 8, 2007, the entire contents of which are hereby incorporated by reference.

TECHNICAL FIELD

This invention relates to the treatment of metabolic disorders using kinase inhibitors.

BACKGROUND

Obesity is a world-wide health problem that is associated with metabolic syndrome, including insulin resistance and the development of type 2 diabetes (Boden, 2003, Exp. Clin. Endocrinol. Diabetes, 111:121-124). Obesity is associated with increased blood levels of free fatty acids (FFA). This increase in FFA is considered to be a causative link between obesity and insulin resistance (Arner, 2002, Diabetes Metab. Res. Rev., 18 Suppl. 2:S5-9; Boden, 2006, Curr. Diab. Rep. 6:177-181; Kahn et al., 2006, Nature, 444:840-846; Kovacs and Stumvoll, 2005, Best Pract. Res. Clin. Endocrinol. Metab., 19:625-635). The mechanism that accounts for FFA-induced insulin resistance is incompletely understood. However, activation of the cJun $NH_2$-terminal kinase (JNK) stress signaling pathway appears to play a major role in the development of obesity-induced insulin resistance (Hirosumi et al., 2002, Nature, 420:333-336). One molecular mechanism that contributes to JNK-induced insulin resistance is the phosphorylation of the insulin receptor adapter protein IRS1 on the inhibitory site Ser-307 (Aguirre et al., 2000, J. Biol. Chem., 275:9047-9054; Aguirre et al., 2002, J. Biol. Chem. 277: 1531-1537; Lee et al., 2003, J. Biol. Chem. 278:2896-2902). FFA-stimulated JNK signaling is therefore an important physiological mechanism of insulin resistance.

SUMMARY

This invention is based, at least in part, on the surprising discovery that mixed lineage kinases (MLKs) mediate FFA-stimulated JNK activation.

Accordingly, this disclosure includes methods of inhibiting FFA-stimulated JNK activation in a cell. The methods include administering FFA to a cell (e.g., a mammalian cell or a human cell) that expresses both an MLK (e.g., MLK1, MLK2, MLK3, or MLK4) and a JNK, and further administering to the cell a composition that specifically inhibits the expression or activity of the MLK.

This disclosure also includes methods of treating one or more metabolic stress disorders in a subject. The methods include identifying a subject (e.g., a mammal or a human) having or at risk for a metabolic stress disorder (e.g., insulin resistance, metabolic syndrome, type 2 diabetes, or a fatty liver disease (e.g., steatosis or steatohepatitis)), and administering to the subject a therapeutically effective amount of a composition that specifically inhibits the expression or activity of one or more MLKs (e.g., one or more of MLK1, MLK2, MLK3, and MLK4). In some embodiments, the composition is a general inhibitor of MLK activity. In some embodiments, the composition includes one or more agents that each specifically inhibit the expression or activity of a MLK (e.g., MLK1, MLK2, MLK3, and MLK4).

The disclosure also includes compositions that specifically inhibits the expression or activity of one or more MLKs (e.g., one or more of MLK1, MLK2, MLK3, and MLK4) for use in medical treatment.

The disclosure also includes the use of a composition that specifically inhibits the expression or activity of one or more MLKs (e.g., one or more of MLK1, MLK2, MLK3, and MLK4) in the preparation of a medicament for the treatment or prevention of a metabolic stress disorder, e.g., insulin resistance, metabolic syndrome, type 2 diabetes, or a fatty liver disease (e.g., steatosis or steatohepatitis).

The disclosure also includes the use of a composition that specifically inhibits the expression or activity of one or more MLKs (e.g., one or more of MLK1, MLK2, MLK3, and MLK4) for the treatment or prevention of a metabolic stress disorder, e.g., insulin resistance, metabolic syndrome, type 2 diabetes, or a fatty liver disease (e.g., steatosis or steatohepatitis).

In some embodiments, the composition is a specific inhibitor of MLK activity. For example, the MLK activity inhibitor can be a small molecule, e.g., an indolocarbazole MLK inhibitor, e.g., CEP-1347, CEP-11004, or K252a. In another example, the MLK inhibitor is an antibody or antigen binding fragment thereof, e.g., the antibody or antigen binding fragment thereof is an intrabody. In some embodiments, administration of an antibody includes administering to the subject or one or more cells of the subject a nucleic acid that encodes the antibody.

In some embodiments, the composition is a specific inhibitor of MLK expression. For example, the MLK expression inhibitor can be an inhibitory nucleic acid (e.g., an antisense nucleic acid or a mediator of RNA inhibition (RNAi)).

This disclosure also includes methods of identifying candidate compounds for treatment of a metabolic stress disorder (e.g., insulin resistance, metabolic syndrome, type 2 diabetes, or a fatty liver disease (e.g., steatosis or steatohepatitis)). The methods include (i) contacting an MLK protein (e.g., MLK1, MLK2, MLK3, or MLK4), or a fragment thereof, with a test compound; and (ii) determining whether the test compound binds to the MLK or fragment thereof; wherein a test compound that binds to the MLK or fragment thereof is a candidate compound for treatment of a metabolic stress disorder.

In another aspect, a method of identifying a candidate compound for treatment of a metabolic stress disorder (e.g., insulin resistance, metabolic syndrome, type 2 diabetes, or a fatty liver disease (e.g., steatosis or steatohepatitis)) includes: (i) measuring the level of an activity of an MLK protein (e.g., MLK1, MLK2, MLK3, or MLK4), or a fragment thereof having said MLK activity, in the presence and absence of a test compound; and (ii) comparing a level of MLK activity in the presence of the compound with a level of MLK activity in the absence of the compound, wherein a decrease in MLK activity in the presence of the compound indicates that the compound is a candidate compound for treatment of a metabolic stress disorder.

In another aspect, a method of identifying a candidate compound for treatment of a metabolic stress disorder (e.g., insulin resistance, metabolic syndrome, type 2 diabetes, or a fatty liver disease (e.g., steatosis or steatohepatitis)) includes: providing a cell expressing an MLK (e.g., MLK1, MLK2, MLK3, or MLK4) nucleic acid or protein; contacting the cell with a test compound; and detecting an effect of the test compound on levels of expression of the MLK nucleic acid or protein. A test compound that decreases expression of the MLK nucleic acid or protein is a candidate compound for treatment of a metabolic stress disorder.

In yet a further aspect, the methods can include providing a cell expressing a reporter construct comprising a promoter region of a gene encoding an MLK linked to a reporter gene, such that expression of the reporter gene is indicative of expression driven by the promoter region; contacting the cell with a test compound; and detecting an effect of the test compound on levels of expression of the reporter gene. A test compound that decreases expression of the reporter gene is a candidate compound for treatment of a metabolic stress disorder.

In some embodiments, a candidate compound for treatment of a metabolic stress disorder is further evaluated by administering the test compound to an animal model of a metabolic stress disorder (e.g., a mouse fed a high fat diet, a mouse fed a methionine-choline-deficient diet, or an ob/ob mouse) and evaluating one or more metabolic parameters in the animal. The candidate compound can separately be evaluated by administering FFA and the test compound to a cell (e.g., a mammalian cell or a human cell) that expresses an MLK (e.g., MLK1, MLK2, MLK3, or MLK4) and evaluating the expression or activity of the MLK in the cell.

This disclosure also includes methods of diagnosing a metabolic stress disorder in a subject. The methods include identifying a subject suspected of being at risk for or having a metabolic stress disorder; and evaluating the expression or activity of one or more MLKs (e.g., MLK1, MLK2, MLK3, or MLK4) in a cell or tissue of the subject. In some embodiments, the cell or tissue is a metabolic cell (e.g., an adipose cell, a hepatic cell, a pancreatic cell (e.g., a pancreatic β cell), a muscle cell, or a brain cell) or a metabolic tissue (e.g., adipose tissue, liver tissue, pancreatic tissue (e.g., pancreatic islet tissue), muscle tissue, or brain tissue). In some embodiments, evaluating expression or activity of the one or more MLKs involves evaluating the phosphorylation state of the one or more MLKs in the cell or tissue or evaluating the phosphorylation state of a downstream effector of the one or more MLKs (e.g., MKK4, MKK7, JNK or IRS1) in the cell or tissue. In some embodiments, an increase or decrease in expression or activity of the MLK as compared to a control is an indication that the subject is at risk for or has a metabolic stress disorder.

The disclosure also includes compositions and kits for diagnosing a metabolic stress disorder in a subject. These compositions and kits include an agent suitable for evaluating the expression or activity of one or more MLKs (e.g., MLK1, MLK2, MLK3, or MLK4) in a cell or tissue of the subject. In some embodiments, the cell or tissue is a metabolic cell (e.g., an adipose cell, a hepatic cell, a pancreatic cell (e.g., a pancreatic β cell), a muscle cell, or a brain cell) or a metabolic tissue (e.g., adipose tissue, liver tissue, pancreatic tissue (e.g., pancreatic islet tissue), muscle tissue, or brain tissue). In some embodiments, evaluating expression or activity of the one or more MLKs involves evaluating the phosphorylation state of the one or more MLKs in the cell or tissue or evaluating the phosphorylation state of a downstream effector of the one or more MLKs (e.g., MKK4, MKK7, JNK or IRS1) in the cell or tissue. In some embodiments, an increase or decrease in expression or activity of the MLK as compared to a control is an indication that the subject is at risk for or has a metabolic stress disorder.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a set of three gels depicting expression of JNK and α-tubulin (Tubulin) and in vitro kinase activity (KA) on cJun (cJun-P) in MEF treated with 0.5 mM for the indicated times. The bar graph depicts relative kinase activity.

FIG. 1B is a set of three gels depicting expression of JNK and α-tubulin (Tubulin) and in vitro kinase activity (KA) on cJun (cJun-P) in MEF treated with the indicated concentrations of palmitate for 16 hours. The bar graph depicts relative kinase activity.

FIG. 1C is a set of three gels depicting expression of JNK and α-tubulin (Tubulin) and in vitro kinase activity (KA) on cJun (cJun-P) in MEF treated for 16 hours with 0.5 mM linoleate (18:2), oleate (18:1), palmitate (16:0), stearic acid (18:0), and an ethanol solvent control (EtOH). The bar graph depicts relative kinase activity.

FIG. 2A, WT and Mkk4$^{-/-}$ MEF. FIG. 2B, WT and Mkk7$^{-/-}$ MEF. FIG. 2C, WT and Mkk4$^{-/-}$ Mkk7$^{-/-}$ MEF.

FIG. 3B, JNK. FIG. 3C, p38. FIG. 3D, ERK1/2.

FIG. 4A is a set of three gels depicting in vitro kinase activity (KA) on cJun (cJun-P) and expression of JNK and α-tubulin (Tubulin) in WT and Mlk3$^{-/-}$ MEF treated with 0.5 mM oleic acid (18:1) or 0.5 mM palmitic acid (16:0) for 16 hours. The bar graph depicts relative kinase activity.

FIG. 4B is a set of two immunoblots depicting phosphorylation (AKT-P) and expression of AKT in WT and Mlk3$^{-/-}$ MEF. MEF were pretreated for 16 hours with BSA or 0.5 mM palmitate. After incubation with 100 nM insulin for 30 minutes, the cells were harvested and AKT expression and phosphorylation at Ser-473 were examined by immunoblot analysis. The bar graph depicts relative AKT phosphorylation.

FIGS. 5A and 5B are sets of three immunoblots depicting phosphorylation of the MLK3 T-loop (Thr277 and Ser281) (MLK3-P) and expression of MLK3 in adipose tissue of mice maintained for 16 weeks on a standard diet or on a high fat diet (HFD). Expression of α-tubulin is shown as a control. FIG. 5A, white epididymal adipose tissue (WAT). FIG. 5B, brown interscapular adipose tissue (BAT).

FIGS. 5C and 5D are sets of three gels depicting expression of MLK3 and JNK and in vitro kinase activity (KA) on cJun (cJun-P) in adipose tissue of wild-type (WT) and Mlk3$^{-/-}$ (KO) mice maintained for 16 weeks on a standard diet (−, Chow) and on a high fat diet (+, HFD). The bar graphs depict relative kinase activity. FIG. 5C, white adipose tissue. FIG. 5D, brown adipose tissue.

FIGS. 5E and 5F are representative histological sections of adipose tissue stained with hematoxylin and eosin from wild-type (WT) and Mlk3$^{-/-}$ mice fed a standard diet (Chow) or high fat diet (HFD) for 16 weeks. FIG. 5E, white adipose tissue. FIG. 5F, brown adipose tissue.

FIG. 7A is a set of three immunoblots depicting phosphorylation (PKC-P) and expression of PKCδ in WT and Mlk3$^{-/-}$ MEF treated for 16 hours with BSA or with 0.5 mM oleic acid (18:1) or 0.5 mM palmitic acid (16:0). Expression of α-tubulin is shown as a control.

FIG. 7B is a set of three gels depicting in vitro kinase activity (KA) on cJun (cJun-P) and expression of flag-tagged JNK1 (Flag-JNK1) and PKC in HEK293 cells in which flag-tagged JNK1 was co-expressed with constitutively active (CA) or kinase-inactive (KD) PKCε.

FIG. 7C is a set of nine gels depicting expression of PKCα, PKCδ, PKCε, MLK3, phospho-MLK3 (MLK3-P), JNK, and Tubulin and in vitro kinase activity (KA) on cJun (cJun-P) of PKGζ$^{-/-}$ MEF pretreated with 1 μM TPA for 24 hours and then treated with 0.5 mM palmitate for 16 hours.

FIG. 7D is a schematic illustration of a JNK signaling pathway that is activated by saturated FFA and is mediated by PKC, MLK, and MKK4/7. S, T, and Y indicate sites of serine, threonine, and tyrosine phosphorylation, respectively, on JNK.

FIGS. 8A-8C depict metabolic parameters of wild-type and Mlk3$^{-/-}$ male mice maintained on a standard (Chow) or a high fat diet (HFD) at 0, 6, 12, and 16 weeks. FIG. 8A is a line graph depicting changes in body weight. FIG. 8B is a bar graph depicting changes in fasting blood glucose concentration. FIG. 8C is a bar graph depicting fasting plasma insulin concentration. Results are presented as mean±SEM, n=10 per group.

FIGS. 10A-10H are the coding and polypeptide sequences for human MLK1 (FIGS. 10A-10B; SEQ ID NOs: 1 and 2), MLK2 (FIGS. 10C-10D; SEQ ID NOs: 3 and 4), MLK3 (FIGS. 10E-10F; SEQ ID NOs: 5 and 6), and MLK4 (FIGS. 10G-10H; SEQ ID NOs: 7 and 8).

DETAILED DESCRIPTION

Figure 2A:
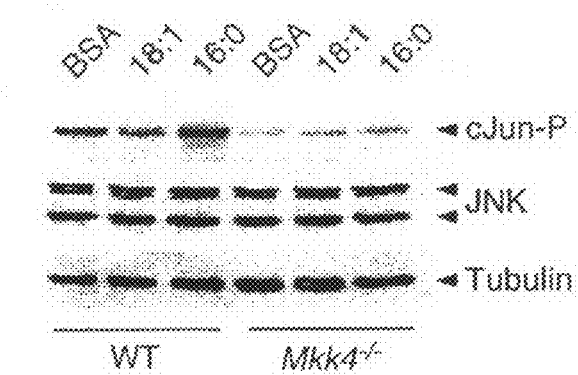
FIGS. 2A-2C are sets of three gels depicting in vitro kinase activity (KA) on cJun (cJun-P) and expression of JNK and α-tubulin (Tubulin) in wild type (WT) or the indicated mutant MEFs treated with 0.5 mM oleic acid (18:1) or 0.5 mM palmitic acid (16:0) for 16 hours.

The results of the present study demonstrate, inter alia, an essential role of MLK3 in the JNK signal transduction pathway that is activated by FFA. This signaling pathway is implicated in FFA-induced insulin resistance that is caused, in part, by JNK-mediated inhibitory phosphorylation of IRS1 on Ser-307 (Weston and Davis, 2007, Curr. Opin. Cell Biol., 19:142-149). This FFA signaling pathway is also implicated in steatosis and the progression to steatohepatitis that is mediated, in part, by JNK-dependent apoptosis (Malhi et al., 2006, J. Biol. Chem., 281:12093-12101; Schattenberg et al., 2006, Hepatology, 43:163-172). The present observations indicate that drugs that target MLK enzymes (like CEP-1347) that can be useful for therapy of neurodegenerative disease (Saporito et al., 2002, Prog. Med. Chem., 40:23-62) can also be useful for the treatment of FFA-induced metabolic stress disorders (e.g., insulin resistance and steatohepatitis).

It is demonstrated herein that the ubiquitously expressed MLK isoform MLK3 is essential for JNK activation caused by FFA and obesity in MEF, brown fat, and liver (FIGS. 3-5, 9). However, MLK3 is not essential in some other tissues, including white fat (FIG. 5). Other MLK isoforms that are not expressed ubiquitously (e.g., MLK1, MLK2, and MLK4) can function redundantly with MLK3 in specific tissues. For example, MLK1 is expressed in epithelial cells and MLK2 is expressed in muscle (Gallo and Johnson, 2002, Nat. Rev. Mol. Cell. Biol., 3:663-672). These members of the MLK family can therefore contribute to the metabolic phenotype.

As used herein, the term "MLK" or "MLK protein" refers to proteins, e.g., eukaryotic proteins, e.g., mammalian proteins, including MLK1, MLK2, MLK3 and MLK4 that are characterized by an NH$_2$-terminal-terminal SH3 domain, a kinase domain, a leucine zipper domain, and a Cdc42/Rac1 binding (CRIB) motif, functional domains, fragments (e.g., functional fragments), e.g., fragments of at least 8 amino acids (e.g., at least 8, 15, 20, 50, 100, 200, 300, 400, 500, 600, 700, or 800 amino acids) and variants thereof, as well as fusion proteins that include any of the above proteins or fragments and a heterologous sequence, e.g., an enzyme, fluorescent protein, or purification tag. Exemplary MLK proteins include those depicted in FIGS. 10A-10H. Variants of MLK proteins will share at least 60% (e.g., at least 80%, 85%, 90%, 95%, 98%, or 99%) sequence identity to a known MLK protein and, e.g., feature kinase activity.

The determination of percent identity between two amino acid sequences is accomplished using the BLAST 2.0 program, which is available to the public at ncbi.nlm.nih.gov/BLAST. Sequence comparison is performed using an ungapped alignment and using the default parameters (BLOSUM 62 matrix, gap existence cost of 11, per residue gap cost of 1, and a lambda ratio of 0.85). The mathematical algorithm used in BLAST programs is described in Altschul et al., 1997, Nucleic Acids Research, 25:3389-3402.

Exemplary nucleotide and polypeptide sequences of human MLKs are presented in FIGS. 10A-10H.

Small Molecule Inhibitors

A specific inhibitor of an MLK can be, e.g., a small molecule. Exemplary small molecules include those of the indolocarbazole class, e.g., CEP-1347 (Maroney et al., 1998, J. Neurosci., 18:104-11; Lund et al., 2005, J. Neurochem. 92:1439-51), CEP-11004 (Murakata et al., 2002, Bioorg. Med. Chem. Lett., 12:147-50), and K252a (Catalog No. 420298, Calbiochem, San Diego, Calif.; Roux et al., 2002, J.

Biol. Chem., 277:49473-80; Gerber et al., 2006, Cancer Res., 66, 5295-5303). Exemplary small molecule inhibitors, including those of the indolocarbazole class, are described in U.S. Pat. No. 6,455,525; U.S. Pat. No. 6,630,500; U.S. Pat. No. 6,811,992; U.S. Pat. No. 6,831,075; U.S. Pat. No. 6,841,567; U.S. Pat. No. 7,074,793; U.S. Pat. No. 7,115,613; U.S. Pat. No. 7,122,679; U.S. Pat. No. 7,169,802; US 2005/0137245; US 2005/0209299; US 2006/0128780; US 2006/0135590; US 2006/0247294; and US 20060276497.

Antibodies

Immunoglobulins can be produced that bind specifically to an MLK (e.g., MLK1, MLK2, MLK3, or MLK4). For example, an immunoglobulin can bind to an MLK and inhibit a signaling activity of the MLK (e.g., a kinase activity, ability to be phosphorylated, or an interaction with an upstream or downstream component of the signaling pathway). In some embodiments, the immunoglobulin is human, humanized, deimmunized, or otherwise non-antigenic in the subject.

In some embodiments, an immunoglobulin can be produced that can distinguish between a phosphorylated MLK and a nonphosphorylated MLK, e.g., an antibody that binds preferentially to one form relative to the other. For example, an antibody that binds preferentially to the phosphorylated form can be an antibody that binds to a phosphorylated T-loop of the MLK (e.g., Phospho-MLK3 (Thr277/Ser281) Antibody #2811 (Cell Signaling Technology, Danvers, Mass.)).

An immunoglobulin can be, for example, an antibody or an antigen-binding fragment thereof. As used herein, the term "immunoglobulin" refers to a protein consisting of one or more polypeptides that include one or more immunoglobulin variable domain sequences. A typical immunoglobulin includes at least a heavy chain immunoglobulin variable domain and a light chain immunoglobulin variable domain. An immunoglobulin protein can be encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 kDa or 214 amino acids) are encoded by a variable region gene at the NH2-terminus (about 110 amino acids) and a kappa or lambda constant region gene at the COOH-terminus. Full-length immunoglobulin "heavy chains" (about 50 kDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion" or "fragment"), as used herein, refers to one or more fragments of a full-length antibody that retain the ability to specifically bind to the antigen. Examples of antigen-binding fragments include: (i) a Fab fragment, a monovalent fragment consisting of the VL, VH, CL and CHI domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science, 242:423-426; and Huston et al. (1988) Proc. Natl. Acad. Sci. USA, 85:5879-5883). Such single chain antibodies are also encompassed within the term "antigen-binding fragment" of an antibody. These antibody fragments are obtained using conventional techniques, and the fragments are screened for utility in the same manner as are intact antibodies.

The new antibodies can be polyclonal, monoclonal, recombinant, e.g., chimeric or humanized, fully human, non-human, e.g., murine, or single chain antibodies. Methods of making such antibodies are known. In some cases, the antibodies have effector function and can fix complement. The antibodies can also be coupled to toxins, reporter groups, or imaging agents.

In one embodiment, the antibody against MLK or another protein is a fully human antibody (e.g., an antibody made in a mouse which has been genetically engineered to produce an antibody from a human immunoglobulin sequence), or a non-human antibody, e.g., a rodent (e.g., a mouse or rat), goat, or primate (e.g., monkey). Typically, the non-human antibody is a rodent (e.g., a mouse or rat) antibody. Methods of producing rodent antibodies are known in the art. Non-human antibodies can be modified, e.g., humanized or deimmunized. Human monoclonal antibodies can be generated using transgenic mice carrying the human immunoglobulin genes rather than the mouse system (see, e.g., WO 91/00906 and WO 92/03918). Other methods for generating immunoglobulin ligands include phage display (e.g., as described in U.S. Pat. No. 5,223,409 and WO 92/20791).

Intrabodies, i.e., intracellularly-made antibodies, can be produced using methods known in the art, such as those disclosed and reviewed in Chen et al., Hum. Gene Ther., 5:595 601 (1994); Marasco, Gene Ther., 4:11 15 (1997); Rondon and Marasco, Annu Rev. Microbiol., 51:257 283 (1997); Proba et al., J. Mol. Biol., 275:245 253 (1998); Cohen et al., Oncogene, 17:2445 2456 (1998); Ohage and Steipe, J. Mol. Biol., 291:1119 1128 (1999); Ohage et al., J. Mol. Biol., 291:1129 1134 (1999); Wirtz and Steipe, Protein Sci., 8:2245 2250 (1999); Zhu et al., J. Immunol. Methods, 231:207 222 (1999); der Maur et al., J. Biol. Chem., 277:45075-85 (2002); Secco et al., J. Immunol. Methods, 285:99-109 (2004); Shaki-Loewenstein et al., J. Immunol. Methods, 303:19-39 (2005); Paz et al., Mol. Cancer. Ther., 4:1801-9 (2005); and references cited therein.

Nucleic Acids

Nucleic acid molecules (e.g., DNA or RNA molecules) can be used to inhibit expression or activity of an MLK (e.g., MLK1, MLK2, MLK3, or MLK4).

An inhibitor of MLK can be a nucleic acid, e.g., a siRNA, anti-sense RNA, or a ribozyme, which can decrease the expression of MLK. In some aspects, a cell or subject can be treated with a compound that modulates the expression of a gene, e.g., a nucleic acid that decreases expression of MLK. Such approaches include oligonucleotide-based therapies such as RNA interference, antisense, ribozymes, and triple helices.

Gene expression can be modified by gene silencing using double-strand RNA (Sharp (1999) Genes and Development 13: 139-141). RNAi methods, including double-stranded RNA interference (dsRNAi) or small interfering RNA (siRNA), have been extensively documented in a number of organisms, including mammalian cells and the nematode C. elegans (Fire et al, Nature, 391, 806-811, 1998). In mammalian cells, RNAi can be triggered by 21-nucleotide (nt) duplexes of small interfering RNA (siRNA) (Chiu et al., Mol. Cell. 10:549-561 (2002); Elbashir et al., Nature 411:494-498 (2001)), or by micro-RNAs (miRNA), functional small-hairpin RNA (shRNA), or other dsRNAs which are expressed in vivo using DNA templates with RNA polymerase III promoters (Zeng et al., Mol. Cell 9:1327-1333 (2002); Paddison et al., Genes Dev. 16:948-958 (2002); Lee et al., Nature Biotechnol. 20:500-505 (2002); Paul et al., Nature Biotechnol. 20:505-508 (2002); Tuschl, T., Nature Biotechnol. 20:440-448 (2002); Yu et al., Proc. Natl. Acad. Sci. USA 99(9):6047-6052 (2002); McManus et al., RNA 8:842-850 (2002); Sui et al., Proc. Natl. Acad. Sci. USA 99(6):5515-5520 (2002)).

dsRNA can be delivered to cells or to an organism to antagonize an MLK or another protein described herein. For example, a dsRNA that is complementary to an MLK nucleic acid can silence protein expression of the MLK. The dsRNA can include a region that is complementary to a coding region of a MLK nucleic acid, e.g., a coding region or a non-coding region, e.g., a 5' or 3' untranslated region. dsRNA can be produced, e.g., by transcribing a cassette (in vitro or in vivo) in both directions, for example, by including a T7 promoter on either side of the cassette. The insert in the cassette is selected so that it includes a sequence complementary to the MLK nucleic acid. The sequence need not be full length, for example, an exon, or between 19-50 nucleotides or 50-200 nucleotides. The sequence can be from the 5' half of the transcript, e.g., within 1000, 600, 400, or 300 nucleotides of the ATG. See also, the HISCRIBE™ RNAi Transcription Kit (New England Biolabs, Ma.) and Fire, A. (1999) Trends Genet., 15:358-363. dsRNA can be digested into smaller fragments. See, e.g., US Patent Applications 2002-0086356 and 2003-0084471.

In one embodiment, an siRNA is used. siRNAs are small double stranded RNAs (dsRNAs) that optionally include overhangs. For example, the duplex region is about 18 to 25 nucleotides in length, e.g., about 19, 20, 21, 22, 23, or 24 nucleotides in length. Typically, the siRNA sequences are exactly complementary to the target mRNA. Exemplary siRNAs that inhibit expression of human and mouse MLKs (e.g., sc-35945, sc-39110, sc-35946 and sc-39111) are commercially available from Santa Cruz Biotechnology, Inc. (Santa Cruz, Calif.).

"Ribozymes" are enzymatic RNA molecules which cleave at specific sites in RNA. Ribozymes that can specifically cleave nucleic acids that encode or that are required for the expression of MLK may be designed according to well-known methods.

A nucleic acid that inhibits MLK expression or activity can be a nucleic acid that encodes an antibody (e.g., an intrabody) that binds specifically to the MLK, e.g., binds specifically to a phosphorylated form of the MLK.

A nucleic acid for inhibiting MLK expression, activity, or function can be inserted into a variety of DNA constructs and vectors for the purposes of gene therapy. Vectors include plasmids, cosmids, artificial chromosomes, viral elements, and RNA vectors (e.g., based on RNA virus genomes). The vector can be competent to replicate in a host cell or to integrate into a host DNA. Viral vectors include, e.g., replication defective retroviruses, adenoviruses and adeno-associated viruses.

Examples of vectors include replication defective retroviral vectors, adenoviral vectors and adeno-associated viral vectors. Adenoviral vectors suitable for use by the methods disclosed herein include (Ad.RSV.lacZ), which includes the Rous sarcoma virus promoter and the lacZ reporter gene as well as (Ad.CMV.lacZ), which includes the cytomegalovirus promoter and the lacZ reporter gene. Methods for the preparation and use of viral vectors are described in WO 96/13597, WO 96/33281, WO 97/15679, and Trapnell et al., Curr. Opin. Biotechnol., 5:617-625, 1994, the contents of which are incorporated herein by reference.

A gene therapy vector is a vector designed for administration to a subject, e.g., a mammal, such that a cell of the subject is able to express a therapeutic gene contained in the vector. The therapeutic gene may encode a protein (e.g., an anti-MLK intrabody). The therapeutic gene can also be used to provide a non-coding transcript, e.g., an antisense RNA, a ribozyme, or a dsRNA, that targets an RNA of an MLK.

The gene therapy vector can contain regulatory elements, e.g., a 5' regulatory element, an enhancer, a promoter, a 5' untranslated region, a signal sequence, a 3' untranslated region, a polyadenylation site, and a 3' regulatory region. For example, the 5' regulatory element, enhancer or promoter can regulate transcription of the DNA encoding the therapeutic polypeptide or other transcript. The regulation can be tissue specific. For example, the regulation can restrict transcription of the desired gene to, e.g., hepatocytes, pancreatic beta cells or adipocytes, e.g., white adipose cells. Alternatively, regulatory elements can be included that respond to an exogenous drug, e.g., a steroid, tetracycline, or the like. Thus, the level and timing of expression of the therapeutic nucleic acid can be controlled.

Gene therapy vectors can be prepared for delivery as naked nucleic acid, as a component of a virus, or of an inactivated virus, or as the contents of a liposome or other delivery vehicle. See, e.g., US 2003-0143266 and 2002-0150626. In one embodiment, the nucleic acid is formulated in a lipid-protein-sugar matrix to form microparticles., e.g., having a diameter between 50 nm to 10 micrometers. The particles may be prepared using any known lipid (e.g., dipalmitoylphosphatidylcholine, DPPC), protein (e.g., albumin), or sugar (e.g., lactose).

The gene therapy vectors can be delivered using a viral system. Exemplary viral vectors include vectors from retroviruses, e.g., Moloney retrovirus, adenoviruses, adeno-associated viruses, and lentiviruses, e.g., Herpes simplex viruses (HSV). See, e.g., US 2003/0147854, 2002/0090716, 2003/0039636, 2002/0068362, and 2003/0104626. The gene delivery agent, e.g., a viral vector, can be produced from recombinant cells which produce the gene delivery system.

A gene therapy vector can be administered to a subject, for example, by intravenous injection, by local administration (see U.S. Pat. No. 5,328,470) or by stereotactic injection (see, e.g., Chen et al. (1994) Proc. Natl. Acad. Sci. USA, 91:3054-57). The gene therapy agent can be further formulated, for example, to delay or prolong the release of the agent by means of a slow release matrix. One method of providing a therapeutic agent, is by inserting a gene therapy vector into cells harvested from a subject. The cells are infected, for example, with a retroviral gene therapy vector, and grown in culture. The subject is then replenished with the infected culture cells. The subject is monitored for recovery and for production of the therapeutic polypeptide or nucleic acid.

Modifications to nucleic acid molecules may be introduced as a means of increasing intracellular stability and half-life. Exemplary modifications include the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

Enzymatic Assays

Enzymatic assays can be used to assess the kinase activity of an MLK (e.g., MLK1, MLK2, MLK3, or MLK4) in the presence or absence of a test compound. Methods of assaying kinase activity or known in the art. Typically, the assay is performed using a reaction mixture that includes an MLK (e.g., purified, partially purified, or a lysate of a cell that expresses the MLK), an MLK substrate (e.g., MKK4/SEK1

(e.g., a K54R mutant), MKK7, or myelin basic protein), and a labeled ATP (e.g., [γ-$^{32}$P]ATP). An exemplary assay for MLK kinase activity that can be performed on multiple samples simultaneously is the Millipore Multiscreen TCA "in-plate" format (Pitt and Lee, 1996, J. Biomol. Screening, 1:47-51). Briefly, each assay mixture contains 20 mM Hepes, pH 7.0, 1 mM EGTA, 10 mM MgCl$_2$, 1 mM DTT, 25 mM β-glycerophosphate, 60 µM ATP, 0.25 µCi [γ-$^{32}$P]ATP, 0.1% BSA, 500 µg/ml myelin basic protein, 2% DMSO, 1 µM of test compound, and 1 µg/ml of purified GST-tagged MLK protein. Samples are incubated for 15 minutes at 37° C. The reaction is stopped by adding ice cold 50% TCA, and the proteins are allowed to precipitate for 30 minutes at 4° C. The plates are then washed with ice cold 25% TCA. Scintillation fluid is added, and the plates are allowed to equilibrate for 1-2 hours prior to counting using a scintillation counter.

Another exemplary assay involves detection of phosphorylation of an MLK substrate (e.g., MKK4) by MLK using an antibody that binds specifically to the phosphorylated form of the substrate (see, e.g., Du et al., 2005, J. Biol. Chem. 280: 42984-42993; Vacratsis and Gallo, 2000, J. Biol. Chem., 275: 27893-27900). These exemplary assays detect MLK activity in cell lysates or immunoprecipitates by detecting phosphorylation of a recombinant GST-MKK4 or recombinant, catalytically inactive GST-MKK7 (K165A) with ATP (e.g., [γ-$^{32}$P]ATP) as a phosphate donor. The lysates or immunoprecipitates are incubated with ATP and substrate in buffer (50 mM Tris-HCl, pH 7.5, 100 mM NaCl, 1 mM MnCl$_2$, 10 mM MgCl$_2$, 0.1 mM Na$_3$VO$_4$) for 20-30 minutes at room temperature. Phosphorylation of substrate is detected using an antibody that binds specifically to the phosphorylated form of the substrate and/or by measuring incorporation of $^{32}$P. These assays can also be performed with purified or partially purified MLK.

Interaction Assays

In some embodiments, interaction with (e.g., binding to) an MLK (e.g., MLK1, MLK2, MLK3, or MLK4) can be assayed, e.g., in vitro or in a cell. The reaction mixture can include, e.g., a phosphate donor, a substrate or other binding partner or potentially interacting fragment thereof. Exemplary binding partners include MKK4 and MKK7, or interacting fragments thereof. Preferably the binding partner is a direct binding partner.

In other embodiments, the reaction mixture can include an MLK binding partner, and compounds can be screened, e.g., in an in vitro assay, to evaluate the ability of a test compound to modulate interaction between an MLK and an MLK binding partner. This type of assay can be accomplished, for example, by coupling one of the components with a radioisotope or enzymatic label such that binding of the labeled component to the other can be determined by detecting the labeled compound in a complex. A component can be labeled with e.g., $^{125}$I, $^{35}$S, $^{33}$P, $^{32}$P, $^{14}$C, or $^{3}$H either directly or indirectly, and the radioisotope detected by direct counting of radioemmission or by scintillation counting. Alternatively, a component can be enzymatically labeled with, for example, horseradish peroxidase, alkaline phosphatase, or luciferase, and the enzymatic label detected by determination of conversion of an appropriate substrate to product. Competition assays can also be used to evaluate a physical interaction between a test compound and a target.

Cell-free assays involve preparing a reaction mixture of the target protein (e.g., an MLK) and the test compound under conditions and for a time sufficient to allow the two components to interact and bind, thus forming a complex that can be removed and/or detected.

The interaction between two molecules can also be detected, e.g., using a fluorescence assay in which at least one molecule is fluorescently labeled. One example of such an assay includes fluorescence energy transfer (FET or FRET for fluorescence resonance energy transfer) (see, for example, U.S. Pat. No. 5,631,169; U.S. Pat. No. 4,868,103). A fluorophore label on the first, "donor" molecule is selected such that its emitted fluorescent energy will be absorbed by a fluorescent label on a second, "acceptor" molecule, which in turn is able to fluoresce due to the absorbed energy. Alternately, the "donor" protein molecule may simply utilize the natural fluorescent energy of tryptophan residues. Labels are chosen that emit different wavelengths of light, such that the "acceptor" molecule label may be differentiated from that of the "donor." Since the efficiency of energy transfer between the labels is related to the distance separating the molecules, the spatial relationship between the molecules can be assessed. In a situation in which binding occurs between the molecules, the fluorescent emission of the "acceptor" molecule label in the assay should be maximal. A FET binding event can be conveniently measured through standard fluorometric detection means well known in the art (e.g., using a fluorimeter).

Another example of a fluorescence assay is fluorescence polarization (FP). For FP, only one component needs to be labeled. A binding interaction is detected by a change in molecular size of the labeled component. The size change alters the tumbling rate of the component in solution and is detected as a change in FP. See, e.g., Nasir et al. (1999) Comb. Chem. HTS, 2:177-190; Jameson et al. (1995) Methods Enzymol., 246:283; Seethala et al. (1998) Anal. Biochem., 255:257. Fluorescence polarization can be monitored in multiwell plates, e.g., using the POLARION™ reader (Tecan, Maennedorf, Switzerland). See, e.g., Parker et al. (2000) J. Biomolecular Screening, 5:77-88; and Shoeman, et al. (1999) Biochem., 38:16802-16809.

In another embodiment, evaluating binding of an MLK protein to a compound can include a real-time monitoring of the binding interaction, e.g., using Biomolecular Interaction Analysis (BIA) (see, e.g., Sjolander and Urbaniczky (1991) Anal. Chem., 63:2338-2345 and Szabo et al. (1995) Curr. Opin. Struct. Biol., 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, an MLK protein is anchored onto a solid phase. The MLK/test compound complexes anchored on the solid phase can be detected at the end of the reaction, e.g., the binding reaction. For example, an MLK protein can be anchored onto a solid surface, and the test compound (which is not anchored) can be labeled, either directly or indirectly, with detectable labels discussed herein.

It may be desirable to immobilize either an MLK protein or an MLK binding partner to facilitate separation of complexed from uncomplexed forms of one or both of the proteins, as well as to accommodate automation of the assay. Binding of a test compound to MLK, or interaction of MLK with a second component in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/mammalian homolog of a fusion proteins or glutathione-S-transferase/target fusion proteins can be adsorbed onto glutathione SEPHAROSE® beads (Sigma Chemical, St. Louis, Mo.) or glutathione derivatized microtiter plates, which are then combined with the test compound or the test compound and either the non-adsorbed target protein or MLK, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of MLK binding or activity determined using standard techniques.

Other techniques for immobilizing either MLK or a target molecule on matrices include using conjugation of biotin and streptavidin. Biotinylated MLK or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface, e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with an MLK or target molecules, but which do not interfere with binding of the MLK to its target molecule. Such antibodies can be derivatized to the wells of the plate, and unbound target or MLK trapped in the wells by antibody conjugation. Methods for detecting such complexes, in addition to those described above for the GST-immobilized complexes, include immunodetection of complexes using antibodies reactive with MLK or the target molecule, as well as enzyme-linked assays which rely on detecting an enzymatic activity associated with MLK or the target molecule.

Alternatively, cell free assays can be conducted in a liquid phase. In such an assay, the reaction products are separated from unreacted components, by any of a number of standard techniques, including but not limited to: differential centrifugation (see, for example, Rivas and Minton (1993) Trends Biochem. Sci., 18:284-7); chromatography (gel filtration chromatography, ion-exchange chromatography); electrophoresis (see, e.g., Ausubel et al., eds., *Current Protocols in Molecular Biology* 1999, J. Wiley: New York.); and immunoprecipitation (see, for example, Ausubel et al., supra). Such resins and chromatographic techniques are known to one skilled in the art (see, e.g., Heegaard (1998) J. Mol. Recognit., 11:141-8; Hage and Tweed (1997) J. Chromatogr. B. Biomed. Sci. Appl., 699:499-525). Further, fluorescence energy transfer may also be conveniently utilized, as described herein, to detect binding without further purification of the complex from solution.

To identify compounds that modulate (e.g., interfere with) the interaction between the target product and its binding partner(s), for example, a reaction mixture containing the target product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target and its cellular or extracellular binding partner. Control reaction mixtures are incubated without the test compound or with a placebo. The formation of any complexes between the target product and the cellular or extracellular binding partner is then detected. The formation of a complex in the control reaction, but not in the reaction mixture containing the test compound, indicates that the compound interferes with the interaction of the target product and the interactive binding partner. Additionally, complex formation within reaction mixtures containing the test compound and normal target product can also be compared to complex formation within reaction mixtures containing the test compound and mutant target product. This comparison can be important in those cases wherein it is desirable to identify compounds that disrupt interactions of mutant but not normal target products.

These assays can be conducted in a heterogeneous or homogeneous format. Heterogeneous assays involve anchoring either the target product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target product or the partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment, a homogeneous assay can be used. For example, a preformed complex of the target product and the interactive cellular or extracellular binding partner product is prepared in that either the target products or their binding partners are labeled, but the signal generated by the label is quenched due to complex formation (see, e.g., U.S. Pat. No. 4,109,496, which utilizes this approach for immunoassays). The addition of a test substance that competes with and displaces one of the species from the preformed complex will result in the generation of a signal above background. In this way, test substances that disrupt target product-binding partner interaction can be identified.

Cell-Based Assays

Cell-based assays can be used to evaluate compounds for their ability to interact with an MLK protein, e.g., bind or modulate the enzymatic activity of an MLK protein. Useful assays include assays in which an MLK-associated parameter is evaluated. Other parameters that can be evaluated include parameters that assess insulin production or secretion.

In addition, it is possible to evaluate the phosphorylation state of an MLK (e.g., MLK1, MLK2, MLK3, or MLK4) or an MLK substrate in an MLK-expressing cell. For example, one can evaluate the phosphorylation of an MLK, an MLK substrate (e.g., MKK4 or MKK7) or a downstream effector of MLK (e.g., MKK4, MKK7, JNK or IRS1). Optionally, the MLK, substrate or downstream effector can be immunoprecipitated from an extract made from the MLK expressing cell (e.g., contacted or not contacted with a test compound). The precipitated proteins can then be evaluated. In another variation, the MLK, MLK substrate, or downstream effector is detected using a reagent that discriminates between the phosphorylated an nonphosphorylated forms. For example, the reagent is an antibody that specifically recognizes a phosphorylated MLK.

Another exemplary cell based assay can include contacting a cell expressing an MLK protein (e.g., MLK1, MLK2, MLK3, or MLK4) with a test compound and determining the ability of the test compound to inhibit an activity of the MLK protein, and/or determine the ability of the test compound to inhibit expression of the MLK, e.g., by detecting MLK nucleic acids (e.g., mRNA or cDNA) or proteins in the cell. Determining the ability of the test compound to modulate MLK activity can be accomplished, for example, by determining the ability of a MLK protein or nucleic acid to bind to or interact with a substrate (e.g., as described above), to bind or interact with the test molecule, and by determining the ability of the test molecule to modulate a parameter, e.g., MLK phosphorylation, MLK substrate (e.g., MKK4 or MKK7) phosphorylation, or phosphorylation of a downstream effector of MLK (e.g., MKK4, MKK7, JNK or IRS1).

Cell-based systems can be used to identify compounds that decrease expression and/or activity and/or effect of an MLK. Such cells can be recombinant or non-recombinant, such as cell lines that express the MLK gene. In some embodiments, the cells can be recombinant or non-recombinant cells which express an MLK substrate or binding partner. Exemplary systems include mammalian or yeast cells that express MLK, e.g., from a recombinant nucleic acid. In utilizing such systems, cells are exposed to compounds suspected of increasing expression and/or activity of MLK. After exposure, the cells are assayed, for example, for MLK expression or activity.

Alternatively, the cells may also be assayed for the activation or inhibition of the phosphorylation function of MLK. In one embodiment, the levels of phosphorylation of an MLK kinase substrate, e.g., MKK4 or MKK7, or downstream effector, e.g., MKK4, MKK7, JNK or IRS1, are evaluated.

A cell-based assay can be performed using a single cell, or a collection of at least two or more cells. The cell can be a yeast cell (e.g., *Saccharomyces cerevisiae*) or a mammalian cell, including but not limited to somatic or embryonic cells (e.g., hepatocytes, adipocytes, or pancreatic beta cells), HepG2 cells, MIN6 cells, INS-1 cells, Chinese hamster ovary cells, HeLa cells, human 293 cells, and monkey COS-7 cells. The collection of cells can form a tissue. A "tissue" refers to a collection of similar cell types (such as adipose, hepatic, pancreatic islet, epithelium, connective, muscle, and nerve tissue).

In another embodiment, modulators of MLK gene expression are identified. For example, a cell or cell free mixture is contacted with a candidate compound and the expression of MLK mRNA or protein evaluated relative to the level of expression of MLK mRNA or protein in the absence of the candidate compound. When expression of the MLK mRNA or protein is greater in the presence of the candidate compound than in its absence, the candidate compound is identified as a stimulator of MLK mRNA or protein expression. Alternatively, when expression of MLK mRNA or protein is less (statistically significantly less) in the presence of the candidate compound than in its absence, the candidate compound is identified as an inhibitor of the MLK mRNA or protein expression. The level of MLK mRNA or protein expression can be determined by methods for detecting MLK mRNA or protein, e.g., using probes or antibodies, e.g., labeled probes or antibodies.

In addition to cell-based and in vitro assay systems, non-human organisms, e.g., transgenic non-human organisms or a model organism, can also be used. A transgenic organism is one in which a heterologous DNA sequence is chromosomally integrated into the germ cells of the animal. A transgenic organism will also have the transgene integrated into the chromosomes of its somatic cells. Organisms of any species, including, but not limited to: yeast, worms, flies, fish, reptiles, birds, mammals (e.g., mice, rats, rabbits, guinea pigs, pigs, micro-pigs, and goats), and non-human primates (e.g., baboons, monkeys, chimpanzees) may be used in the methods described herein.

A transgenic cell or animal used in the methods disclosed herein can include a transgene that encodes, e.g., MLK. The transgene can encode a protein that is normally exogenous to the transgenic cell or animal, including a human protein, e.g., human MLK. The transgene can be linked to a heterologous or a native promoter. A transgenic animal can also be produced with reduced expression or activity of MLK, e.g., an MLK deletion or mutant. Methods of making transgenic cells and animals are known in the art.

Accordingly, in another embodiment, this disclosure features a method of identifying a compound as a candidate of treatment of a metabolic stress disorder, e.g., insulin resistance, metabolic syndrome, type 2 diabetes, or a fatty liver disease (steatosis or steatohepatitis). The method includes: providing a compound which interacts with, e.g., binds to, MLK; and evaluating the effect of the test compound on a subject, e.g., an animal model, e.g., an animal model for a metabolic disorder, e.g., type 2 diabetes. Exemplary animal models are described below. The interaction between a test compound and MLK can be evaluated by any of the methods described herein, e.g., using cell-based assays or cell-free in vitro assays.

Test Compounds

A "compound" or "test compound" can be any chemical compound, for example, a macromolecule (e.g., a polypeptide, a protein complex, or a nucleic acid) or a small molecule (e.g., an amino acid, a nucleotide, an organic or inorganic compound). The test compound can have a formula weight of less than about 10,000 grams per mole (e.g., less than 5,000, 1,000, or 500 grams per mole). The test compound can be naturally occurring (e.g., an herb or a natural product), synthetic, or both. Examples of macromolecules are proteins, protein complexes, and glycoproteins, nucleic acids, e.g., DNA, RNA (e.g., double stranded RNA or RNAi), and PNA (peptide nucleic acid). Examples of small molecules are peptides, peptidomimetics (e.g., peptoids), amino acids, amino acid analogs, polynucleotides, polynucleotide analogs, nucleotides, nucleotide analogs, nucleosides, glycosidic compounds, organic or inorganic compounds e.g., heteroorganic or organometallic compounds. One exemplary type of protein compound is an antibody or a modified scaffold domain protein. A test compound can be the only substance assayed by the method described herein. Alternatively, a collection of test compounds can be assayed either consecutively or concurrently by the methods described herein.

In some embodiments, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175; Furka, Int. J. Pept. Prot. Res., 37:487-493 (1991); and Houghton et al., Nature, 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci., 90:6909-6913 (1993)), vinylogous polypeptides (Hagihara et al., J Amer. Chem. Soc., 114:6568 (1992)), nonpeptidal peptidomimetics with glucose scaffolding (Hirschmann et al., J Amer. Chem. Soc., 114:9217-9218 (1992)), analogous organic syntheses of small compound libraries (Chen et al., J. Amer. Chem. Soc., 116:2661 (1994)), oligocarbamates (Cho et al., Science, 261:1303 (1993)), and/or peptidyl phosphonates (Campbell et al., J Org. Chem., 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525, 735 and 5,519,134; morpholino compounds, U.S. Pat. No. 5,506,337; benzodiazepines, U.S. Pat. No. 5,288,514, indolocarbazole compounds, U.S. Pat. Nos. 6,013,646, 6,541,468; and the like). Additional examples of methods for the synthesis of molecular libraries can be found in the art, for example in: DeWitt et al. (1993) Proc. Natl. Acad. Sci. USA, 90:6909; Erb et al. (1994) Proc. Natl. Acad. Sci. USA, 91:11422; Zuckermann et al. (1994). J. Med. Chem., 37:2678; Cho et al. (1993) Science, 261:1303; Carrell et al. (1994) Angew. Chem. Int. Ed. Engl., 33:2059; Carell et al. (1994) Angew. Chem. Int. Ed. Engl., 33:2061; and Gallop et al. (1994) J Med. Chem., 37:1233.

Some exemplary libraries can be used to generate variants from a particular lead compound. One method includes generating a combinatorial library in which one or more functional groups of the lead compound are varied, e.g., by derivatization. Thus, the combinatorial library can include a class of compounds which have a common structural feature (e.g., framework).

Devices for the preparation of combinatorial libraries are commercially available (see, e.g., 357 MPS, 390 MPS, Advanced Chem Tech, Louisville Ky.; SYMPHONY™, Rainin, Woburn, Mass.; 433A Applied Biosystems, Foster City, Calif.; 9050 Plus, Millipore, Bedford, Mass.). In addition, numerous combinatorial libraries are themselves commercially available (see, e.g., ComGenex, Princeton, N.J.; Asinex, Moscow, RU, Tripos, Inc., St. Louis, Mo.; ChemStar, Ltd, Moscow, RU; 3D Pharmaceuticals, Exton, Pa.; Martek Biosciences, Columbia, Md.; etc.).

Test compounds can also be obtained from: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) J Med. Chem., 37:2678-85); spatially addressable parallel solid phase or solution phase libraries; synthetic library methods requiring deconvolution; the "one-bead one-compound" library method; and synthetic library methods using affinity chromatography selection. The biological libraries include libraries of nucleic acids and libraries of proteins. Some nucleic acid libraries encode a diverse set of proteins (e.g., natural and artificial proteins; others provide, for example, functional RNA and DNA molecules such as nucleic acid aptamers or ribozymes. A peptoid library can be made to include structures similar to a peptide library. (See also Lam (1997) Anticancer Drug Des., 12:145). A library of proteins may be produced by an expression library or a display library (e.g., a phage display library).

Libraries of compounds may be presented in solution (e.g., Houghten (1992) Biotechniques, 13:412-421), or on beads (Lam (1991) Nature, 354:82-84), chips (Fodor (1993) Nature, 364:555-556), bacteria (Ladner, U.S. Pat. No. 5,223,409), spores (Ladner U.S. Pat. No. 5,223,409), plasmids (Cull et al. (1992) Proc. Natl. Acad. Sci. USA, 89:1865-1869) or on phage (Scott and Smith (1990) Science, 249:386-390; Devlin (1990) Science, 249:404-406; Cwirla et al. (1990) Proc. Natl. Acad. Sci., 87:6378-6382; Felici (1991) J. Mol. Biol., 222: 301-310).

Metabolic Stress Disorders

An agent that inhibits (e.g., decreases or reduces) MLK expression or activity can be used to treat or prevent a metabolic stress disorder, e.g., insulin resistance, metabolic syndrome, type 2 diabetes, or a fatty liver disease (steatosis or steatohepatitis). In some embodiments, the metabolic stress disorder is induced or aggravated by FFA. The agent can be administered to a subject in an amount effective to treat, prevent, or ameliorate at least one symptom of the metabolic stress disorder. While not wishing to be bound by theory, it is believed that inhibitors of MLK expression or activity can act to treat or prevent metabolic disorders by blocking the FFA-stimulated activation of JNK (see FIG. 7D). In some embodiments, the methods include selecting a subject on the basis that they have, or are at risk for, a metabolic stress disorder.

The results disclosed herein demonstrate an essential role of MLKs in the JNK signal transduction pathway that is activated by FFA. This signaling pathway is implicated in FFA-induced insulin resistance that is caused, in part, by JNK-mediated inhibitory phosphorylation of IRS1 on Ser-307 (Weston and Davis, 2007, Curr. Opin. Cell Biol., 19:142-149). This FFA signaling pathway is also implicated in steatosis and the progression to steatohepatitis that is mediated, in part, by JNK-dependent apoptosis (Malhi et al., 2006, J. Biol. Chem., 281:12093-12101; Schattenberg et al., 2006, Hepatology, 43:163-172). These results indicate that drugs that target MLK enzymes (e.g., CEP-1347, CEP-11004, and K252a) that have therapeutic benefits for neurodegenerative disease (Saporito et al., 2002, Prog. Med. Chem., 40:23-62; Wang et al., 2004, Annu Rev. Pharmacol. Toxicol., 44:451-474) can also be useful for the treatment of FFA-induced metabolic stress disorders, e.g., insulin resistance and steatohepatitis.

Insulin resistance is characterized by a reduced response of insulin-sensitive tissues to normal amounts of insulin. In response, the pancreas secretes increased amounts of insulin to compensate. Individuals with insulin resistance commonly have high levels of blood glucose and circulating insulin.

Metabolic syndrome (e.g., Syndrome X) is a syndrome characterized by a group of metabolic risk factors in one person. These factors include two or more of (particularly three, four, five or more, or all of): central obesity (excessive fat tissue in and around the abdomen), atherogenic dyslipidemia (blood fat disorders, mainly high triglycerides and low HDL cholesterol, that foster plaque buildups in artery walls); insulin resistance or glucose intolerance (the body cannot properly use insulin or blood sugar); prothrombotic state (e.g., high fibrinogen or plasminogen activator inhibitor-1 (PAI-1) in the blood); raised blood pressure (i.e., hypertension) (e.g., 130/85 mmHg or higher); and proinflammatory state (e.g., elevated high-sensitivity C-reactive protein in the blood). The underlying causes of this syndrome include overweight/obesity, physical inactivity and genetic factors. People with metabolic syndrome are at increased risk of coronary heart disease, other diseases related to plaque buildups in artery walls (e.g., stroke and peripheral vascular disease), and type 2 diabetes. Metabolic syndrome is closely associated with insulin resistance.

Type 2 diabetes mellitus is a metabolic disease of impaired glucose homeostasis characterized by hyperglycemia, or high blood sugar, as a result of defective insulin action which manifests as insulin resistance, defective insulin secretion, or both. A patient with Type 2 diabetes mellitus has abnormal carbohydrate, lipid, and protein metabolism associated with insulin resistance and/or impaired insulin secretion. The disease leads to pancreatic beta cell destruction and eventually absolute insulin deficiency. Without insulin, high glucose levels remain in the blood. The long term effects of high blood glucose include blindness, renal failure, and poor blood circulation to these areas, which can lead to foot and ankle amputations. Early detection can be important in preventing patients from reaching this severity. The majority of patients with diabetes have the non-insulin dependent form of diabetes, currently referred to as Type 2 diabetes mellitus. This disclosure also includes methods of treating disorders related to or resulting from diabetes, for example end organ damage, diabetic gastroparesis, diabetic neuropathy, or cardiac dysrythmia.

Fatty liver disease includes fat in the liver (steatosis) and fatty liver with inflammation and liver damage (steatohepatitis). Fatty liver disease is often associated with alcoholism or viral hepatitis, but can be found in patients without such presentations (e.g., non-alcoholic steatohepatitis (NASH)). Symptoms often include elevations in liver tests included in routine blood test panels, such as alanine aminotransferase (ALT) or aspartate aminotransferase (AST). Liver fat can also be observed in x rays or imaging studies of the liver. Steatohepatitis (e.g., NASH) can be diagnosed and distinguished from steatosis by liver biopsy. Steatohepatitis is diagnosed when microscopic examination of the tissue shows fat along with inflammation and damage to liver cells. Scar tissue may also be present in steatohepatitic liver.

A variety of criteria, including genetic, biochemical, physiological, and cognitive criteria, can be used to evaluate a metabolic stress disorder, e.g., insulin resistance, metabolic syndrome, type 2 diabetes, or a fatty liver disease (steatosis or steatohepatitis), in a subject. Symptoms and diagnosis of a metabolic stress disorder are known to medical practitioners. Information about these indications and other indications known to be associated with a metabolic stress disorder can be used as a parameter associated with the disorder. Metabolites that are associated with a metabolic stress disorder can be detected by a variety of means, including enzyme-coupled assays, using labeled precursors, and nuclear magnetic resonance (NMR). For example, NMR can be used to determine the relative concentrations of phosphate-based compounds in a sample, e.g., creatine levels. Other metabolic parameters such as fasting glucose levels, glucose tolerance, insulin levels, redox state, ion concentration (e.g., $Ca^{2+}$) (e.g., using ion-sensitive dyes), and membrane potential (e.g., using patch-clamp technology) can also be assayed.

Animal Models

Animal models of metabolic stress disorders can be used to evaluate candidate compounds for therapeutic effects. Exemplary animal models are reviewed in Russel and Proctor, 2006, Cardiovasc. Pathol., 15:318-330; Sharma and McNeill, 2006, Curr. Vasc. Pharmacol., 4:293-304; Wagner et al., 2006, ILAR J., 47:259-271; Bellinger et al., 2006, ILAR J., 47:243-258; Matveyenko and Butler, 2006; ILAR J., 47:225-233; Cefalu, 2006, ILAR J., 47:186-198; Shafrir et al., 2006, ILAR J., 47:212-224; Kaplan and Wagner, 2006, ILAR J., 47:181-185; LeRoith and Gavrilova, 2006, Int. J. Biochem. Cell Biol., 38:904-912; Chen and Wang, 2005, Diabetes Obes. Metab., 7:307-317; Plum et al., 2005, Physiology, 20:152-161; Rees and Alcolado, 2005, Diabet. Med., 22:359-70; Postic et al., 2004, Ann. Endocrinol., 65:51-59; Kahn, 2003, Exp. Diabesity Res., 4:169-182; Nandi et al., 2004, Physiol. Rev., 84:623-647; Hoenig, 2006, Curr. Opin. Nutr. Metab. Care, 9:584-588; Bergman et al., 2006, Obesity, 14:16S-19S; Armitage et al., 2005, J. Physiol., 565:3-8; Barnard and Aronson, 2005, Recent Results Cancer Res., 166:47-61, Armitage et al., 2004, J. Physiol., 561:355-377; and Tofovic and Jackson, 2003, Methods Mol. Med., 86:29-46.

Exemplary models of metabolic stress disorders include dietary models, e.g., models in which animals (e.g., mice) are fed a high fat diet, which induces obesity and insulin resistance (see, e.g., Jaeschke et al., 2004, Genes Dev., 18:1976-80), or a diet deficient in methionine and choline, which induces fat deposit in the liver with progression to steatohepatitis (see, e.g., Schattenberg et al., 2006, Hepatology., 43:163-72).

Exemplary molecular models of Type II diabetes include: a transgenic mouse having defective Nkx-2.2 or Nkx-6.1; (U.S. Pat. No. 6,127,598); Zucker Diabetic Fatty fa/fa (ZDF) rat (U.S. Pat. No. 6,569,832); diabetic (db/db) mouse (Chen et al., 1996, Cell, 84:491-495); obese (ob/ob) mouse (Pelleymounter et al., 1995, Science, 269:540-543); Rhesus monkeys, which spontaneously develop obesity and subsequently frequently progress to overt type 2 diabetes (Hotta et al., Diabetes, 50:1126-33 (2001); and a transgenic mouse with a dominant-negative IGF-1 receptor (KR-IGF-1R) having Type 2 diabetes-like insulin resistance.

Additional exemplary models of fatty liver disease include: Anstee and Goldin, 2006, Int. J. Exp. Pathol., 87:1-16; Portincasa et al., 2005, Clin. Biochem., 38:203-217; Yki-Järvinen and Westerbacka, 2005, Curr. Mol. Med., 5:287-295; Nanji, 2004, Clin. Liver Dis., 8:559-574; den Boer et al., 2004, Arterioscler. Thromb. Vasc. Biol., 24:644-649; and Koteish and Mae Diehl, 2002, Best Pract. Res. Clin. Gastroenterol., 16:679-690.

Therapeutic and Diagnostic Uses

An evaluation of MLK (e.g., MLK1, MLK2, MLK3, MLK4) activity or expression in a cell or tissue of a subject can include qualitative or quantitative information. An example of quantitative information is a numerical value of one or more dimensions, e.g., a concentration of a protein or a tomographic map. Qualitative information can include an assessment, e.g., a physician's comments or a binary ("yes"/"no") and so forth. A parameter can include information that indicates that the subject is not diagnosed with a metabolic stress disorder, e.g., diabetes, or other disorder described herein or does not have a particular indication of a metabolic disorder, e.g., diabetes, or other disorder described herein.

Techniques to detect expression or activity of an MLK in a sample from a subject include cellular, immunological, and other biological methods known in the art. For general guidance, see, e.g., techniques described in Sambrook & Russell, *Molecular Cloning: A Laboratory Manual*, 3rd Edition, Cold Spring Harbor Laboratory, N.Y. (2001), Ausubel et al., Current Protocols in Molecular Biology (Greene Publishing Associates and Wiley Interscience, N.Y. (1989), (Harlow, E. and Lane, D. (1988) *Antibodies: A Laboratory Manual*, Cold Spring Harbor Laboratory Press, Cold Spring Harbor, N.Y.), and updated editions thereof.

For example, antibodies, other immunoglobulins, and other specific binding ligands can be used to detect an MLK, e.g., a phosphorylated MLK. For example, one or more specific antibodies can be used to probe a sample. Various formats are possible, e.g., ELISAs, fluorescence-based assays, Western blots, and protein arrays. Methods of producing polypeptide arrays are described in the art, e.g., in De Wildt et al. (2000). Nature Biotech. 18, 989-994; Lueking et al. (1999). Anal. Biochem. 270, 103-111; Ge, H. (2000). Nucleic Acids Res. 28, e3, I-VII; MacBeath, G., and Schreiber, S. L. (2000). Science 289, 1760-1763; and WO 99/51773A1. A polypeptide array can be produced to detect one or more MLKs (e.g., phosphorylated MLKs) in conjunction with one or more other proteins involved in metabolism (e.g., leptin or leptin receptor).

MLK proteins and protein activity can also be analyzed using mass spectroscopy, chromatography, electrophoresis, enzyme interaction or using probes that detect post-translational modification (e.g., a phosphorylation of MLK or an MLK substrate or downstream effector).

Nucleic acid expression can be detected in cells from a subject, e.g., removed by surgery, extraction, post-mortem or other sampling (e.g., blood, CSF). Expression of one or more MLKs can be evaluated, e.g., by hybridization based techniques, e.g., Northern analysis, RT-PCR, SAGE, and nucleic acid arrays. Nucleic acid arrays are useful for profiling multiple mRNA species in a sample. A nucleic acid array can be generated by various methods, e.g., by photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145). A nucleic acid array can detect one or more MLKs (e.g., phosphorylated MLKs) in conjunction with one or more other proteins involved in metabolism (e.g., leptin or leptin receptor).

Metabolites that are associated with a metabolic disorder, e.g., diabetes, or other disorder described herein can be detected by a variety of means, including enzyme-coupled assays, using labeled precursors, and nuclear magnetic resonance (NMR). For example, NMR can be used to determine the relative concentrations of phosphate-based compounds in a sample, e.g., creatine levels. Other metabolic parameters such as redox state, ion concentration (e.g., $Ca^2$)(e.g., using ion-sensitive dyes), and membrane potential can also be detected (e.g., using patch-clamp technology).

The detection of MLK expression or activity can be used to detect cells that have been activated by FFA. Detection of such cells can be useful in early diagnosis of metabolic stress disorders, e.g., insulin resistance. Additionally, antibodies to an MLK, e.g., a phosphorylated MLK, can be used to target therapeutic molecules (e.g., inhibitors of MLK activity or expression) to cells that have been activated by FFA.

An evaluation of MLK expression or activity in a cell or tissue of a subject can be compared to a control or reference value. Control or reference values can be determined by one of ordinary skill in the art and can include, e.g., a value (e.g., a mean or median value) obtained from one or more individuals diagnosed as having a metabolic stress disorder; a value (e.g., a mean or median value) obtained from one or more individuals diagnosed as not having a metabolic stress disorder; a value (e.g., a mean or median value) obtained from one or more individuals diagnosed as being at risk for a metabolic stress disorder; a value (e.g., a mean or median value) obtained from a random sample or population of individuals; or a threshold value (e.g., above which the subject is determined to have a probability (e.g., about 50%, 60%, 70%, 80%, 90%, 95%, 98%, 99% or greater) of being at risk for or having a metabolic stress disorder. Threshold values can be determined by analysis of values of MLK expression or activity of individuals diagnosed as not having, having, or being at risk for one or more metabolic stress disorders.

The methods described herein in which an antibody to an MLK is employed can be performed, for example, by utilizing pre-packaged kits comprising at least one such specific antibody described herein, which may be conveniently used, for example, in clinical settings, to diagnose subjects exhibiting symptoms of metabolic stress disorders.

In some aspects, a compound (e.g., an antibody or antigen-binding fragment thereof) that binds to an MLK can be used in the production of a composition, e.g., a therapeutic or diagnostic composition, by conjugating a therapeutic or diagnostic moiety such as a drug, toxin, chelator, a boron compound and a detectable label, to the MLK binding compound. Methods for making such compositions are known in the art, see, e.g., McCarron et al., Mol Interv., 5:368-80 (2005), and U.S. Pat. Pub. No. 2006/0088539. The compositions can be used to target drug molecules to cells that contain an MLK, e.g., a phosphorylated MLK. In some embodiments, these compositions can be used to treat metabolic stress disorders. For example, the therapeutic moiety can be an inhibitor of MLK expression or activity, e.g., an inhibitor of MLK expression or activity described herein.

Techniques for conjugating a therapeutic or diagnostic moiety to an antibody are well known (see, e.g., Amon et al., 1985, "Monoclonal Antibodies For Immunotargeting Of Drugs In Cancer Therapy", in *Monoclonal Antibodies And Cancer Therapy*, Reisfeld et al., Eds., Alan R. Liss, Inc. pp. 243-256; Hellstrom et al., 1987, "Antibodies For Drug Delivery", in *Controlled Drug Delivery*, 2nd ed., Robinson et al., Eds., Marcel Dekker, Inc., pp. 623-653; Thorpe, 1985, "Antibody Carriers Of Cytotoxic Agents In Cancer Therapy: A Review", in *Monoclonal Antibodies '84: Biological And Clinical Applications*, Pinchera et al., Eds., pp. 475-506; "Analysis, Results, And Future Prospective Of The Therapeutic Use Of Radiolabeled Antibody In Cancer Therapy", in *Monoclonal Antibodies For Cancer Detection And Therapy*, Baldwin et al., Eds., Academic Press, pp. 303-316, 1985; and Thorpe et al., 1982, Immunol. Rev., 62:119-158). Alternatively, an antibody can be conjugated to a second antibody to form an antibody heteroconjugate as described by Segal in U.S. Pat. No. 4,676,980.

Pharmaceutical Formulations

Standard principles of medicinal chemistry can be used to produce derivatives of an inhibitor of MLK expression or activity. Derivatives can be screened for improved pharmacological properties, for example, efficacy, pharmaco-kinetics, stability, solubility, and clearance. The moieties responsible for a compound's activity in the assays described above can be delineated by examination of structure-activity relationships (SAR) as is commonly practiced in the art. A person of ordinary skill in pharmaceutical chemistry can modify moieties on a candidate compound or agent and measure the effects of the modification on the efficacy of the compound or agent to thereby produce derivatives with increased potency. For an example, see Nagarajan et al., J. Antibiot., 41:1430-8 (1988). Furthermore, if the biochemical target of the compound (or agent) is known or determined, the structure of the target and the compound can inform the design and optimization of derivatives. Molecular modeling software is commercially available (e.g., from Molecular Simulations, Inc.) for this purpose.

The compounds and agents, nucleic acids, polypeptides, and antibodies (all of which can be referred to herein as "active compounds"), can be incorporated into pharmaceutical compositions. Such compositions typically include the active compound and a pharmaceutically acceptable carrier or excipient. A "pharmaceutically acceptable carrier" can include solvents, dispersion media, coatings, antibacterial and antifungal agents, isotonic and absorption delaying agents, and the like, compatible with pharmaceutical administration. Supplementary active compounds can also be incorporated into the compositions.

There are a number of methods by which the new compositions for use in the new methods can be delivered to subjects, in general, and to specific cells or tissue in those subjects, in particular. In one example, plasmids encoding antibodies specific to midbody scar components (e.g., intrabodies) can be injected into a tissue. The plasmids would then enter cells in that tissue and express a specific antibody, which, in turn, would bind to the targeted midbody scar protein. Delivery specificity of such plasmids can be enhanced by associating them with organ- or tissue-specific affinity, so that they preferentially enter specified cell types.

Compounds and their physiologically acceptable salts and solvates may be formulated for administration by inhalation or insufflation (either through the mouth or the nose) or oral, buccal, parenteral or rectal administration.

The compounds will generally be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, for example, sterile pyrogen-free water, before use. Where the compositions are intended for use in a specific treatment area, the compositions can be administered by one or more local injections into the tumor site to diminish as much as possible any side effects relating to the compound's activities outside of the treatment area.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

The therapeutic compositions of the invention can also contain a carrier or excipient, many of which are known to skilled artisans. Methods for making such formulations are well known and can be found in, for example, *Remington: The Science and Practice of Pharmacy*, University of the Sciences in Philadelphia (USIP), 2005.

The compositions can also be formulated for intracellular delivery of the active compounds, using methods known in the art. For example, the compositions can include liposomes or other carriers that deliver the active compound across the plasma membrane. Vesicles that are covered with membrane-permeant peptides, such as Tat or Antennapedia, can also be used. A number of other methods for enhancing intracellular delivery are familiar to those of skill in the art.

It is recognized that the pharmaceutical compositions and methods described herein can be used independently or in combination with one another. That is, subjects can be administered one or more of the pharmaceutical compositions, e.g., pharmaceutical compositions comprising a nucleic acid molecule or protein of the invention or a modulator thereof, subjected to one or more of the therapeutic methods described herein, or both, in temporally overlapping or non-overlapping regimens. When therapies overlap temporally, the therapies may generally occur in any order and can be simultaneous (e.g., administered simultaneously together in a composite composition or simultaneously but as separate compositions) or interspersed. By way of example, a subject afflicted with a disorder described herein can be simultaneously or sequentially administered both a cytotoxic agent which selectively kills aberrant cells and an antibody (e.g., an antibody of the invention) which can, in one embodiment, be conjugated or linked with a therapeutic agent, a cytotoxic agent, an imaging agent, or the like.

Effective Doses

Toxicity and therapeutic efficacy of an inhibitor of MLK expression or activity can be determined by standard pharmaceutical procedures, using either cells in culture or experimental animals to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Inhibitors that exhibit large therapeutic indices are preferred. While inhibitors that exhibit toxic side effects may be used, care can be taken to design a delivery system that targets such compounds to the site of affected tissue to minimize potential damage to non-target cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the new methods, the therapeutically effective dose can be estimated initially from cell culture assays. A dose can also be calculated in animal models to achieve a circulating plasma concentration range that includes the IC50 (that is, the concentration of the test compound which achieves a half-maximal inhibition of symptoms) as determined in cell culture. Such information can be used to more accurately determine useful doses in humans.

EXAMPLES

The invention is further illustrated by the following examples. The examples are provided for illustrative purposes only. They are not to be construed as limiting the scope or content of the invention in any way.

Example 1

Experimental Procedures

Mice

Mlk3$^{-/-}$ mice (Brancho et al., 2005, Mol. Cell. Biol., 25:3670-3681) were back-crossed ten generations to the C57B1/6J strain (Jackson Laboratories, Bar Harbor, Me.) and were housed in a facility accredited by the American association for Laboratory Animal Care. The animal studies were approved by the Institutional Animal Care and Use Committee of the University of Massachusetts. Male mice were fed a high fat diet ad libitum (Diet F3282, Bio-Serv, Frenchtown, N.J.) or a standard diet for 16 weeks, and their body mass was recorded weekly. Blood samples were collected from the tail vein after an overnight fast after 6, 12, and 16 weeks on the diet. Blood glucose concentrations were measured with a DEX® glucometer (Bayer, Tarrytown, N.Y.), and plasma insulin was measured by ELISA kit for rat insulin (Crystal Chem, Downers Grove, Ill.). Tissues were removed and rapidly frozen in liquid nitrogen for biochemical analysis. Histology was performed using tissue fixed in 10% formalin, dehydrated, and embedded in paraffin. Sections were stained with hematoxylin and eosin.

Cell Culture

Wild-type, Mkk4$^{-/-}$, Mkk7$^{-/-}$, and Mkk4$^{-/-}$ Mkk7$^{-/-}$ MEF (Tournier et al., 2001, Genes Dev., 15:1419-1426) and wild-type and Mlk3$^{-/-}$ MEF have been previously described (Brancho et al., 2005, Mol. Cell. Biol., 25:3670-3681). Wild-type and PkcÇ$^{-/-}$ MEF have also been described (Leitges et al., 2001, Mol. Cell, 8:771-780). MEF and HEK293 cells (American Type Culture Collection) were cultured in Dulbecco's modified Eagle's medium (DMEM) supplemented with 10% fetal bovine serum (Invitrogen, Carlsbad, Calif.). HEK293 cells were transfected with Lipofectamine™ transfection reagent (Invitrogen, Carlsbad, Calif.). Sodium salts of fatty acids (Sigma-Aldrich, St. Louis, Mo.) were dissolved in PBS and mixed with free fatty acid (FFA)-free BSA (Roche). Stearic acid (Sigma-Aldrich, St. Louis, Mo.) was dissolved in ethanol and added to serum-free DMEM supplemented with 2% FFA-free BSA. After 1 hour incubation in serum-free DMEM, cells were treated with 0.5 mM fatty acid/0.5% BSA for 1-16 hours at 37° C.

Plasmids

Plasmid expression vectors for wild-type and kinase-negative PKCε were used in some experiments (Cai et al., 1997, Mol. Cell. Biol. 17:732-741). The plasmid expression vector for Flag-tagged JNK1 was described previously (Derijard et al., 1994, Cell, 76:1025-1037).

Biochemical Assays

Protein extracts were prepared using lysis buffer [20 mM Tris™ buffer (pH 7.4), 1% Triton™ X-100 detergent, 10% glycerol, 137 mM NaCl, 2 mM EDTA, 25 mM β-glycerophosphate, 1 mM sodium orthovanadate, 1 mM phenylmethylsulfonyl fluoride, and 10 μg/mL of aprotinin and leupeptin]. Extracts (50 μg of protein) were examined by immunoblot analysis with antibodies obtained from Cell Signaling (MLK3, phosphoThr277, Ser281-MLK3, ERK, phospho-ERK, p38, phospho-p38, AKT, phosphoSer473-AKT, PKCα, PKCδ, phospho-T-loop-PKC, and phospho-JNK), Transduction Labs (PKCε), PharMingen (JNK), Sigma (α-Tubulin), and Upstate Biotechnology (IRS1, phospho-Ser307-IRS1 and phospho-MKK7). JNK activity was measured in an in vitro kinase assay using [γ-$^{32}$P]ATP and cJun as substrates (Whitmarsh and Davis, 2001, Methods Enzymol., 332:319-336).

Example 2

JNK is Activated by Saturated FFA

FFA-stimulated JNK activation was examined in mouse embryonic fibroblasts (MEF). Treatment with palmitate caused JNK activation in a time- and dose-dependent manner that was detected by an in vitro kinase assay using [γ-$^{32}$P]ATP and cJun as substrates (FIGS. 1A-1B). The concentration of FFA that was sufficient to activate JNK in these cells is within the physiological range for blood FFA concentrations in wild-type mice (Kim et al., 2004, J. Clin. Invest., 114:823-827).

The capacity of different FFA to activate JNK in MEF was investigated. Incubation with saturated FFA, including palmitate and stearate, resulted in JNK activation, whereas addition of mono- and poly-unsaturated FFA (oleate and linoleate) had no effect (FIG. 1C). This example demonstrates that exposure of MEF to saturated FFA, but not unsaturated FFA, causes JNK activation.

Example 3

FFA-Stimulated JNK Activation is Mediated by MKK4 and MKK7

Figure 2B:
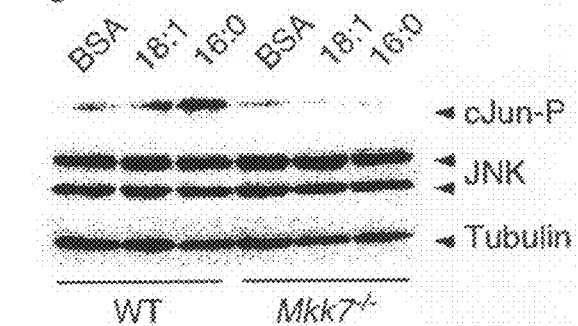
Figure 2C:
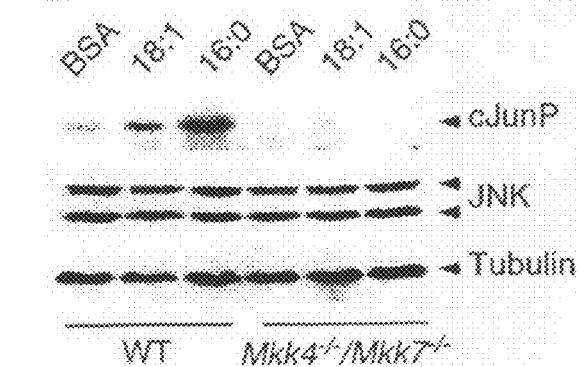

The effect of MKK4 and MKK7-deficiency on FFA-stimulated JNK activation was tested. Compound mutant Mkk4$^{-/-}$ Mkk7$^{-/-}$ MEF failed to exhibit JNK activation in response to treatment with palmitate (FIG. 2C). Similarly, Mkk4$^{-/-}$ MEF and Mkk7$^{-/-}$ MEF both failed to respond to palmitate with increased JNK activation (FIGS. 2A-2B). These data indicate that both MKK4 and MKK7 are required for FFA-stimulated JNK activity in MEF.

Example 4

MLK3 is Required for FFA-Stimulated JNK Activation

Figure 3A:
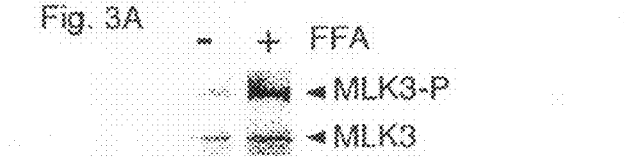
FIG. 3A is a set of two immunoblots depicting phosphorylation of the MLK3 T-loop (Thr277 and Ser281)(MLK3-P) and expression of MLK3 in wild-type MEF treated for 16 hours with 0.5 mM palmitic acid (+ FFA).

To test whether MLK3 is a component of a FFA-induced signaling pathway, the effect of FFA on MLK3 regulation was examined. Immunoblot analysis using an antibody to the MLK3 T-loop phosphorylation sites Thr-277 and Ser-281 demonstrated that treatment with saturated FFA caused increased T-loop phosphorylation of MLK3 (FIG. 3A). This observation indicates that MLK3 is activated by FFA and that MLK3 is a component of a FFA-stimulated signaling pathway.

Figure 3B:
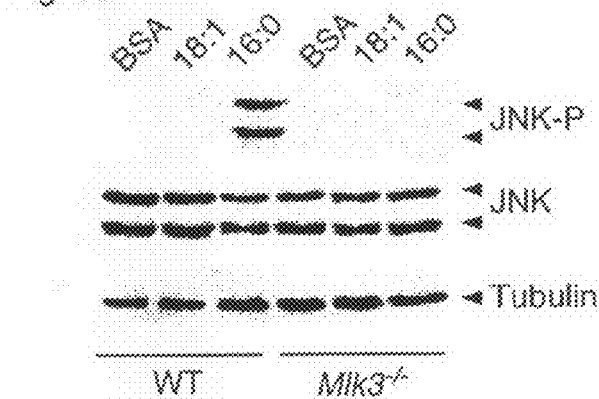
FIGS. 3B-3D are sets of three immunoblots depicting phosphorylation and expression of the indicated proteins in WT and Mlk3$^{-/-}$ MEF treated with 0.5 mM oleic acid (18:1) or 0.5 mM palmitic acid (16:0) for 16 hours. In each figure, expression of α-tubulin is shown as a control.

To test whether MLK3 may be required for FFA-stimulated JNK activation, MEF were prepared from wild-type and Mlk3$^{-/-}$ mice. Treatment of wild-type MEF with saturated FFA (palmitate), but not unsaturated FFA (oleate), caused increased JNK activation (FIG. 3B). In contrast, Mlk3$^{-/-}$ MEF were unresponsive to saturated FFA (FIG. 3B). This analysis demonstrated that MLK3 is necessary for FFA-stimulated JNK activation in MEF.

Figure 3C:
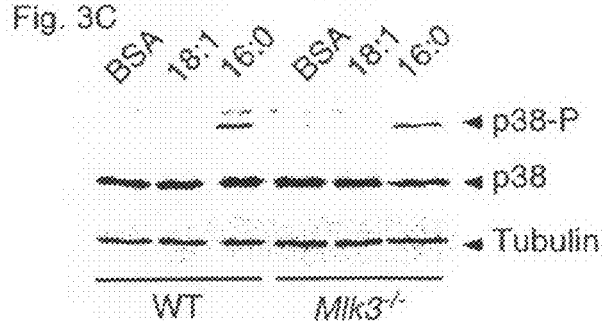
Figure 3D:
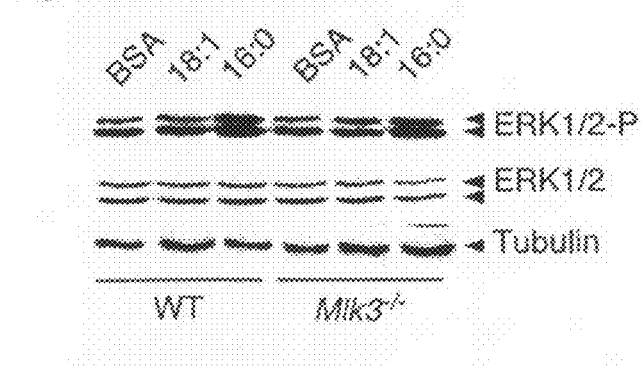

It is possible that MLK3 may mediate the effects of FFA on the p38 MAPK and ERK1/2 signaling pathways. Indeed, p38 MAPK and ERK1/2 were activated by treatment with saturated FFA, although the response of these MAPK pathways was modest compared with the robust effect of FFA to activate JNK (FIGS. 3B-3D). Comparative studies indicated that MLK3-deficiency selectively blocked the effect of FFA on JNK activation. These studies demonstrated that MLK3 is required for FFA-stimulated JNK activation and that it plays either no role or a redundant role in FFA-stimulated activation of other MAPK pathways.

Example 5

MLK3-Deficient Cells are Protected Against FFA-Induced Insulin Resistance

The effect of FFA on insulin signaling in MEF was examined. Control studies demonstrated that treatment with FFA caused JNK activation (FIG. 4A) and markedly decreased insulin-stimulated AKT activation (FIG. 4B). In contrast, MLK3-deficient cells did not exhibit FFA-stimulated JNK activation (FIG. 4A), and FFA did not inhibit insulin-stimulated AKT activation (FIG. 4B). Together, these data indicate that MLK3 is essential for FFA-stimulated JNK activation and insulin resistance.

Example 6

Role of MLK3 in Obesity-Induced JNK Activation

Studies using cultured cells indicated that MLK3 is essential for FFA-stimulated JNK activation (FIGS. 2-4). These observations suggested that MLK3 may be important for JNK regulation by FFA in vivo. To test this hypothesis, the effect of MLK3-deficiency was examined in an animal model that is associated with increased concentrations of blood FFA. Feeding mice a high fat diet causes increased blood FFA and JNK activation (Hirosumi et al., 2002, Nature, 420:333-336). The high fat diet also caused MLK3 activation that was detected by increased MLK3 T-loop phosphorylation in both epididymal white adipose tissue and interscapular brown adipose tissue (FIGS. 5A-5B).

To test whether MLK3 contributes to JNK activation in vivo, adipose tissue was examined from mice fed either a control diet (chow) or a high fat diet. JNK was activated in both the white fat (FIG. 5C) and the brown fat (FIG. 5D) of mice fed a high fat diet. Studies of Mlk3$^{-/-}$ mice demonstrated that MLK3 was required for obesity-induced JNK activation in brown fat (FIG. 5D), but not in white fat (FIG. 5C). The non-essential role of MLK3 in white fat may reflect the expression of other members of the MLK group in this tissue. These data indicate that MLK3 is essential for obesity-induced JNK activation in brown fat and that MLK3 may play only a redundant role in white fat. Histological analysis of adipose tissue demonstrated that feeding a high fat diet caused hypertrophy of both white and brown adipose tissue (FIG. 5E, 5F). No differences between white fat from wild-type and Mlk3$^{-/-}$ mice were detected. However, MLK3-deficiency did cause markedly reduced lipid accumulation in the brown fat of mice fed a high fat diet.

Example 7

MLK3 is Required for Inhibitory Phosphorylation of IRS1

Figure 6A:
FIG. 6A shows two sets of two immunoblots depicting phosphorylation of IRS1 on Ser-307 (S307-P) and IRS1 expression in white epididymal adipose tissue (WAT) and brown interscapular adipose tissue (BAT) of WT and Mlk3$^{-/-}$ mice maintained for 16 weeks on a standard diet (−) or on a high fat diet (+, HFD).

The adapter protein IRS1, an important mediator of signaling by the insulin receptor, is phosphorylated on tyrosine and serves to recruit multiple insulin-regulated signaling modules, including PI-3 kinase (White, 2006, Can. J. Physiol. Pharmacol., 84:725-737). JNK can suppress IRS1 function by phosphorylating the inhibitory site Ser-307 (Aguirre et al., 2000, J. Biol. Chem., 275:9047-9054; Aguirre et al., 2002, J. Biol. Chem., 277:1531-1537; Lee et al., 2003, J. Biol. Chem., 278:2896-2902). This observation suggests that IRS1 phosphorylation may be an important target of JNK signaling in mice fed a high fat diet (Hirosumi et al., 2002, Nature, 420: 333-336). Indeed, immunoblot analysis demonstrated that feeding a high fat diet to wild-type mice caused increased phosphorylation of IRS1 on the JNK phosphorylation site Ser-307 in both white and brown adipose tissue (FIG. 6A). Studies of Mlk3$^{-/-}$ mice demonstrated that MLK3-deficiency slightly reduced IRS1 phosphorylation on Ser-307 in white adipose tissue and markedly suppressed IRS1 Ser-307 phosphorylation in brown adipose tissue (FIG. 6A). These defects in IRS1 Ser-307 phosphorylation indicate that MLK3-deficiency reduces obesity-induced JNK activation (FIGS. 5C, 5D).

Figure 6B:
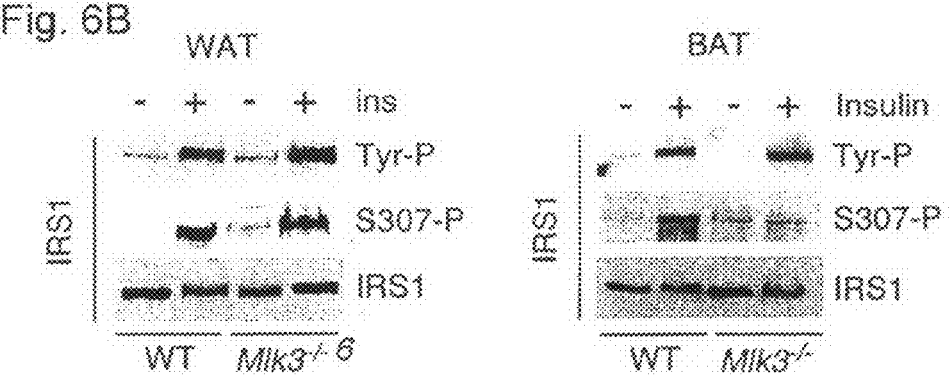
FIG. 6B shows two sets of three immunoblots depicting tyrosine phosphorylated IRS1 (Tyr-P), IRS1 phosphorylated on Ser-307 (S307-P), and IRS1 expression in white epididymal adipose tissue (WAT) and brown interscapular adipose tissue (BAT) of WT and Mlk3$^{-/-}$ mice fasted overnight and then treated for 30 minutes with insulin (1.5 units/Kg).
Figure 9A:
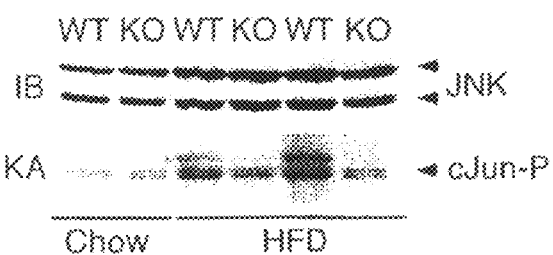
FIG. 9A is a set of two gels depicting JNK expression and in vitro kinase activity (KA) on cJun (cJun-P) in the liver of wild-type (WT) and Mlk3$^{-/-}$ (KO) mice maintained for 16 weeks on a standard diet (Chow) or on a high fat diet (HFD).
Figure 9B:
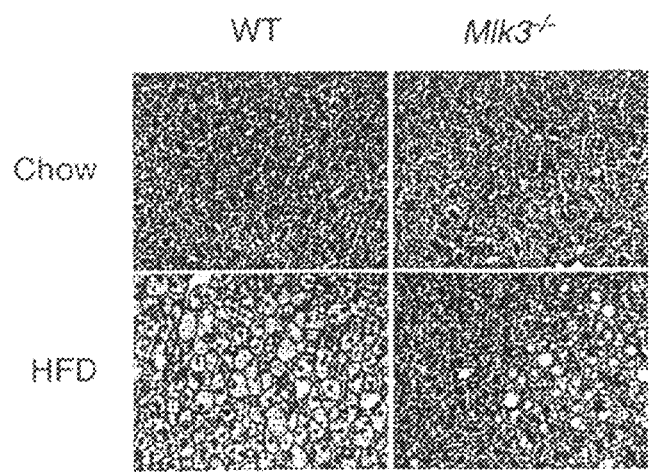
FIG. 9B is a set of four photomicrographs depicting histological sections of liver stained with hematoxylin and eosin from wild-type (WT, left column) and Mlk3$^{-/-}$ (right column) mice fed a standard diet (Chow, top row) or high fat diet (HFD, bottom row) for 16 weeks.

To test whether these changes in inhibitory IRS1 phosphorylation are functionally relevant, the effect of insulin to cause tyrosine phosphorylation of IRS1 was examined. Studies of white adipose tissue demonstrated a similar increase in phosphorylation of IRS1 on Tyr and Ser-307 in wild-type and Mlk3$^{-/-}$ mice (FIG. 6B). In contrast, studies of brown adipose tissue demonstrated that MLK3-deficiency caused decreased Ser-307 phosphorylation and markedly increased Tyr phosphorylation of IRS1 in brown adipose tissue (FIG. 6B). These data provide biochemical evidence of increased insulin sensitivity of brown fat in MLK3-deficient mice. Together, these data indicate that MLK3 is required for JNK-induced insulin resistance in brown adipose tissue.

The observation that insulin signaling is altered in Mlk3$^{-/-}$ mice indicated that MLK3-deficiency, like JNK-deficiency, can protect against diet-induced obesity and insulin resistance. It was found that feeding a high fat diet caused similar changes in body mass, glucose tolerance, insulin tolerance, and fasting blood insulin and glucose concentrations in wild-type and Mlk3$^{-/-}$ mice (FIGS. 8A-8C). The lack of systemic protection against diet-induced obesity and insulin resistance caused by MLK3-deficiency is most likely the result of the finding that MLK3 is required for obesity-induced JNK activation in brown adipose tissue (FIGS. 5-6) and liver (FIGS. 9A-9B) of Mlk3$^{-/-}$ mice, but MLK3 is not essential in other tissues, including white adipose tissue (FIGS. 5-6) and muscle. The function of MLK3 is probably redundant in white fat and other tissues because of the expression of other members of the MLK group.

Example 8

PKC is Required for MLK3—Dependent JNK Activation Caused by FFA

The effect of FFA to activate PKC in MEF was examined by immunoblot analysis using a PKC phosphospecific antibody. This analysis demonstrated that saturated FFA, but not unsaturated FFA, caused PKC activation in both wild-type and Mlk3$^{-/-}$ MEF (FIG. 7A). These data indicate that FFA can activate PKC independently of MLK3. To test whether PKC might act as an upstream component of a FFA-stimulated pathway that activates JNK, the effect of constitutively activated PKC and kinase-negative PKC on JNK activity was compared. These data demonstrated that PKC can activate JNK (FIG. 7B). PKC can therefore function as a mediator of FFA signaling to MLK3.

To test the requirement of PKC for FFA-stimulated MLK3 and JNK activation, the effect of PKC down-regulation was examined. In initial studies, siRNA was used to down-regulate the PKC isoforms expressed in MEF (PKCα, PKCδ, PKCε, and PKCζ). Down-regulation of individual PKC isoforms caused no change in FFA-induced MLK3 or JNK activation. This observation suggested that PKC isoforms may serve redundant functions in this pathway. Efficient simultaneous down-regulation of multiple PKC isoforms using siRNA was not obtained. An alternative approach was therefore used to obtain MEF lacking multiple PKC isoforms. Treatment with the phorbol ester TPA (Phorbol-12-Myristate-13-Acetate) caused down-regulation of diacylglycerol-responsive PKC isoforms (α, δ, and ε), but did not affect FFA-induced MLK3 or JNK activation. This observation suggested an important role for PKCζ, although Pkcζ$^{-/-}$ MEF exhibited no defect of FFA-induced MLK3 and JNK activation (FIG. 7C). The effect of pan-PKC deficiency was therefore examined by treating Pkcζ$^{-/-}$ MEF with TPA (FIG. 7C). This approach demonstrated that PKC was essential for FFA-induced activation of both MLK3 and JNK (FIG. 7C). These data indicate that multiple PKC isoforms (α, δ, ε, and ζ) in MEF serve redundant functions as upstream components of a FFA-stimulated signaling pathway that regulates MLK3-dependent activation of JNK (FIG. 7D).

Example 8

MLK Inhibitors Reduce Development of Insulin Resistance

The effects of the MLK inhibitor CEP-1347 on development of insulin resistance in mice is determined. Male mice are fed a high fat diet ad libitum (Diet F3282, Bio-Serv, Frenchtown, N.J.) or a standard diet for 16 weeks, with each group administered CEP-1347 subcutaneously (s.c.) at a dose of 0.5 or 2.5 mg/kg or vehicle control, twice per day. Body mass is recorded weekly, and blood samples are collected from the tail vain after an overnight fast after 6, 12, and 16 weeks on the diet. Blood glucose concentrations are measured with a DEX® glucometer (Bayer, Tarrytown, N.Y.), and plasma insulin is measured by ELISA kit for rat insulin (Crystal Chem, Downers Grove, Ill.). Glucose tolerance tests are performed by i.p. administration of glucose (1.8 g/kg) and measurement of blood glucose at t=15, 30, 60, 90, and 120 minutes in 16-week-old mice. Insulin tolerance tests are done similarly except with the injection of human insulin (1 unit per kg; Lilly Research Laboratories, Indianapolis). Untreated animals fed the high fat diet display hyperinsulinemia, hyperglycemia, decreased insulin sensitivity, and impaired glucose disposal. CEP-1347 decreases these symptoms as compared to control treatment in the animals fed the high-fat diet. This example demonstrates that MLK inhibitors can reduce development of insulin resistance.

Example 9

MLK Inhibitors Alleviate Insulin Resistance

The effects of the MLK inhibitor CEP-1347 to alleviate established insulin resistance in mice is determined. Ten-week old ob/ob mice (Jackson Laboratory, Bar Harbor, Me.) are obese and display hyperinsulinemia, hyperglycemia, decreased insulin sensitivity, and impaired glucose disposal. Such mice are administered CEP-1347 subcutaneously (s.c.) at a dose of 0.5 or 2.5 mg/kg or vehicle control, twice per day for two weeks. Blood glucose concentrations are measured with a DEX® glucometer (Bayer, Tarrytown, N.Y.), and plasma insulin is measured by ELISA kit for rat insulin (Crystal Chem, Downers Grove, Ill.). Following day 14 of the treatment, glucose tolerance tests are performed by i.p. administration of glucose (1.8 g/kg) and measurement of blood glucose at t=15, 30, 60, 90, and 120 minutes. Insulin tolerance tests are performed similarly except with the injection of human insulin (1 unit per kg; Lilly Research Laboratories, Indianapolis). CEP-1347 decreases hyperinsulinemia and hyperglycemia and at least partially restores insulin and glucose tolerance as compared to vehicle control. This example demonstrates that MLK inhibitors can alleviate characteristics of insulin resistance.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating type 2 diabetes in a subject, the method comprising:
   identifying a subject having or at risk for type 2 diabetes; and
   administering to the subject a therapeutically effective amount of a composition that specifically inhibits the expression or activity of a mixed lineage kinase (MLK), thereby treating type 2 diabetes in the subject.

2. The method of claim 1, wherein the subject is a human.

3. The method of claim 1, wherein the composition is a specific inhibitor of MLK activity.

4. The method of claim 3, wherein the composition is CEP-1347, CEP-11004, or K252a.

5. The method of claim 3, wherein the composition is an antibody or antigen binding fragment thereof.

6. The method of claim 5, wherein the antibody is an intrabody.

7. The method of claim 1, wherein the composition is a specific inhibitor of MLK expression.

8. The method of claim 7, wherein the composition is an inhibitory nucleic acid.

9. The method of claim 8, wherein the inhibitory nucleic acid is an antisense nucleic acid or a mediator of RNA inhibition (RNAi).

10. The method of claim 1, wherein the MLK is MLK1, MLK2, MLK3, or MLK4.

11. The method of claim 1, wherein the MLK is MLK3.

* * * * *

SEQUENCE LISTING

<160> NUMBER OF SEQ ID NOS: 8

<210> SEQ ID NO 1
<211> LENGTH: 3315

<212> TYPE: DNA
<213> ORGANISM: Human

<400> SEQUENCE: 1

| | | | | | |
|---|---|---|---|---|---|
| atggagccct | ccagagcgct | tctcggctgc | ctagcgagcg | ccgccgctgc | cgccccgccg | 60 |
| ggggaggatg | gagcagggc | cggggccgag | gaggaggagg | aggaggagga | ggaggcggcg | 120 |
| gcggcggtgg | gccccgggga | gctgggctgc | gacgcgccgc | tgccctactg | gacggccgtg | 180 |
| ttcgagtacg | aggcggcggg | cgaggacgag | ctgaccctgc | ggctgggcga | cgtggtggag | 240 |
| gtgctgtcca | aggactcgca | ggtgtccggc | gacgagggct | ggtggaccgg | gcagctgaac | 300 |
| cagcgggtgg | gcatcttccc | cagcaactac | gtgaccccgc | gcagcgcctt | ctccagccgc | 360 |
| tgccagcccg | gcggcgagga | ccccagttgc | tacccgccca | ttcagttgtt | agaaattgat | 420 |
| tttgcggagc | tcaccttgga | agagattatt | ggcatcgggg | gctttgggaa | ggtctatcgt | 480 |
| gctttctgga | tagggatga | ggttgctgtg | aaagcagctc | gccacgaccc | tgatgaggac | 540 |
| atcagccaga | ccatagagaa | tgttcgccaa | gaggccaagc | tcttcgccat | gctgaagcac | 600 |
| cccaacatca | ttgccctaag | aggggtatgt | ctgaaggagc | ccaacctctg | cttggtcatg | 660 |
| gagtttgctc | gtggaggacc | tttgaataga | gtgttatctg | ggaaaaggat | tcccccagac | 720 |
| atcctggtga | attgggctgt | gcagattgcc | agagggatga | actacttaca | tgatgaggca | 780 |
| attgttccca | tcatccaccg | cgaccttaag | tccagcaaca | tattgatcct | ccagaaggtg | 840 |
| gagaatggag | acctgagcaa | caagattctg | aagatcactg | attttggcct | ggctcgggaa | 900 |
| tggcaccgaa | ccaccaagat | gagtgcggca | gggacgtatg | cttggatggc | acccgaagtc | 960 |
| atccgggcct | ccatgttttc | caaaggcagt | gatgtgtgga | gctatggggt | gctactttgg | 1020 |
| gagttgctga | ctggtgaggt | gccctttcga | ggcattgatg | gcttagcagt | cgcttatgga | 1080 |
| gtggccatga | acaaactcgc | ccttcctatt | ccttctacgt | gcccagaacc | ttttgccaaa | 1140 |
| ctcatggaag | actgctggaa | tcctgatccc | cactcacgac | catctttcac | gaatatcctg | 1200 |
| gaccagctaa | ccaccataga | ggagtctggt | ttctttgaaa | tgcccaagga | ctccttccac | 1260 |
| tgcctgcagg | acaactggaa | acacgagatt | caggagacgt | ttgaccaact | cagggccaaa | 1320 |
| gaaaaggaac | ttcgcacctg | ggaggaggag | ctgacgcggg | ctgcactgca | gcagaagaac | 1380 |
| caggaggaac | tgctgcggcg | tcgggagcag | gagctggccg | agcgggagat | tgacatcctg | 1440 |
| gaacgggagc | tcaacatcat | catccaccag | ctgtgccagg | agaagcccg | ggtgaagaaa | 1500 |
| cgcaagggca | agttcaggaa | gagccggctg | aagctcaagg | atggcaaccg | catcagcctc | 1560 |
| ccttctgatt | ccagcacaa | gttcacggtg | caggcctccc | ctaccatgga | taaaaggaag | 1620 |
| agtcttatca | cagccgctc | cagtcctcct | gcaagcccca | ccatcattcc | tcgccttcga | 1680 |
| gccatccagt | tgacaccagg | tgaaagcagc | aaaacctggg | gcaggagctc | agtcgtccca | 1740 |
| aaggaggaag | ggaggagga | ggagaagagg | gccccaaaga | gaagggacg | gacgtggggg | 1800 |
| ccagggacgc | ttggtcagaa | ggagcttgcc | tcgggagatg | aaggatcccc | tcagagacgt | 1860 |
| gagaaagcta | atggtttaag | taccccatca | gaatctccac | atttccactt | gggcctcaag | 1920 |
| tccctggtag | atggatataa | gcagtggtcg | tccagtgccc | ccaacctggt | gaagggccca | 1980 |
| aggagtagcc | cggccctgcc | agggttcacc | agccttatgg | agatggagga | tgaggacagt | 2040 |
| gaaggcccag | ggagtggaga | gagtcgccta | cagcattcac | ccagccagtc | ctacctctgt | 2100 |
| atcccattcc | ctcgtggaga | ggatggcgat | ggccccctcca | gtgatggaat | ccatgaggag | 2160 |
| cccacccag | tcaactcggc | cacgagtacc | cctcagctga | cgccaaccaa | cagcctcaag | 2220 |

```
cggggcggtg cccaccaccg ccgctgcgag gtggctctgc tcggctgtgg ggctgttctg    2280
gcagccacag gcctagggtt tgacttgctg gaagctggca agtgccagct gcttcccctg    2340
gaggagcctg agccaccagc ccgggaggag aagaaaagac gggagggtct ttttcagagg    2400
tccagccgtc ctcgtcggag caccagcccc ccatcccgaa agcttttcaa gaaggaggag    2460
cccatgctgt tgctaggaga cccctctgcc tccctgacgc tgctctccct ctcctccatc    2520
tccgagtgca actccacacg ctccctgctg cgctccgaca gcgatgaaat tgtcgtgtat    2580
gagatgccag tcagcccagt cgaggcccct cccctgagtc catgtaccca caacccctg    2640
gtcaatgtcc gagtagagcg cttcaaacga gatcctaacc aatctctgac tcccacccat    2700
gtcaccctca ccacccctc gcagcccagc agtcaccggc ggactccttc tgatggggcc    2760
cttaagccag agactctcct agccagcagg agccctcca gcaatgggtt gagcccagt    2820
cctggagcag gaatgttgaa acccccagt cccagccgag acccaggtga attccccgt    2880
ctccctgacc ccaatgtggt cttccccca accccaaggc gctggaacac tcagcaggac    2940
tctaccttgg agagaccca gactctggag tttctgcctc ggccgcgtcc ttctgccaac    3000
cggcaacggc tggacccttg gtggtttgtg tcccccagcc atgcccgcag cacctcccca    3060
gccaacagct ccagcacaga gacgcccagc aacctggact cctgctttgc tagcagtagc    3120
agcactgtag aggagcggcc tggacttcca gccctgctcc cgttccaggc agggccgctg    3180
cccccgactg agcggacgct cctggacctg gatgcagagg ggcagagtca ggacagcacc    3240
gtgccgctgt gcagagcgga actgaacaca cacaggcctg cccccttatga gatccagcag    3300
gagttctggt cttag                                                   3315

<210> SEQ ID NO 2
<211> LENGTH: 1104
<212> TYPE: PRT
<213> ORGANISM: Human

<400> SEQUENCE: 2

Met Glu Pro Ser Arg Ala Leu Leu Gly Cys Leu Ala Ser Ala Ala Ala
 1               5                  10                  15

Ala Ala Pro Pro Gly Glu Asp Gly Ala Gly Ala Gly Ala Glu Glu Glu
                20                  25                  30

Glu Glu Glu Glu Glu Glu Ala Ala Ala Val Gly Pro Gly Glu Leu
            35                  40                  45

Gly Cys Asp Ala Pro Leu Pro Tyr Trp Thr Ala Val Phe Glu Tyr Glu
        50                  55                  60

Ala Ala Gly Glu Asp Glu Leu Thr Leu Arg Leu Gly Asp Val Val Glu
65                  70                  75                  80

Val Leu Ser Lys Asp Ser Gln Val Ser Gly Asp Glu Gly Trp Trp Thr
                85                  90                  95

Gly Gln Leu Asn Gln Arg Val Gly Ile Phe Pro Ser Asn Tyr Val Thr
            100                 105                 110

Pro Arg Ser Ala Phe Ser Ser Arg Cys Gln Pro Gly Gly Glu Asp Pro
        115                 120                 125

Ser Cys Tyr Pro Pro Ile Gln Leu Leu Glu Ile Asp Phe Ala Glu Leu
    130                 135                 140

Thr Leu Glu Glu Ile Ile Gly Ile Gly Gly Phe Gly Lys Val Tyr Arg
145                 150                 155                 160

Ala Phe Trp Ile Gly Asp Glu Val Ala Val Lys Ala Ala Arg His Asp
                165                 170                 175
```

-continued

```
Pro Asp Glu Asp Ile Ser Gln Thr Ile Glu Asn Val Arg Gln Glu Ala
            180                 185                 190

Lys Leu Phe Ala Met Leu Lys His Pro Asn Ile Ile Ala Leu Arg Gly
        195                 200                 205

Val Cys Leu Lys Glu Pro Asn Leu Cys Leu Val Met Glu Phe Ala Arg
    210                 215                 220

Gly Gly Pro Leu Asn Arg Val Leu Ser Gly Lys Arg Ile Pro Pro Asp
225                 230                 235                 240

Ile Leu Val Asn Trp Ala Val Gln Ile Ala Arg Gly Met Asn Tyr Leu
                245                 250                 255

His Asp Glu Ala Ile Val Pro Ile Ile His Arg Asp Leu Lys Ser Ser
            260                 265                 270

Asn Ile Leu Ile Leu Gln Lys Val Glu Asn Gly Asp Leu Ser Asn Lys
        275                 280                 285

Ile Leu Lys Ile Thr Asp Phe Gly Leu Ala Arg Glu Trp His Arg Thr
    290                 295                 300

Thr Lys Met Ser Ala Ala Gly Thr Tyr Ala Trp Met Ala Pro Glu Val
305                 310                 315                 320

Ile Arg Ala Ser Met Phe Ser Lys Gly Ser Asp Val Trp Ser Tyr Gly
                325                 330                 335

Val Leu Leu Trp Glu Leu Leu Thr Gly Glu Val Pro Phe Arg Gly Ile
            340                 345                 350

Asp Gly Leu Ala Val Ala Tyr Gly Val Ala Met Asn Lys Leu Ala Leu
        355                 360                 365

Pro Ile Pro Ser Thr Cys Pro Glu Pro Phe Ala Lys Leu Met Glu Asp
    370                 375                 380

Cys Trp Asn Pro Asp Pro His Ser Arg Pro Ser Phe Thr Asn Ile Leu
385                 390                 395                 400

Asp Gln Leu Thr Thr Ile Glu Glu Ser Gly Phe Phe Glu Met Pro Lys
                405                 410                 415

Asp Ser Phe His Cys Leu Gln Asp Asn Trp Lys His Glu Ile Gln Glu
            420                 425                 430

Thr Phe Asp Gln Leu Arg Ala Lys Glu Lys Glu Leu Arg Thr Trp Glu
        435                 440                 445

Glu Glu Leu Thr Arg Ala Ala Leu Gln Gln Lys Asn Gln Glu Glu Leu
    450                 455                 460

Leu Arg Arg Arg Glu Gln Glu Leu Ala Glu Arg Glu Ile Asp Ile Leu
465                 470                 475                 480

Glu Arg Glu Leu Asn Ile Ile Ile His Gln Leu Cys Gln Glu Lys Pro
                485                 490                 495

Arg Val Lys Lys Arg Lys Gly Lys Phe Arg Lys Ser Arg Leu Lys Leu
            500                 505                 510

Lys Asp Gly Asn Arg Ile Ser Leu Pro Ser Asp Phe Gln His Lys Phe
        515                 520                 525

Thr Val Gln Ala Ser Pro Thr Met Asp Lys Arg Lys Ser Leu Ile Asn
    530                 535                 540

Ser Arg Ser Ser Pro Pro Ala Ser Pro Thr Ile Ile Pro Arg Leu Arg
545                 550                 555                 560

Ala Ile Gln Leu Thr Pro Gly Glu Ser Ser Lys Thr Trp Gly Arg Ser
                565                 570                 575

Ser Val Val Pro Lys Glu Glu Gly Glu Glu Glu Lys Arg Ala Pro
            580                 585                 590

Lys Lys Lys Gly Arg Thr Trp Gly Pro Gly Thr Leu Gly Gln Lys Glu
```

```
            595                 600                 605
Leu Ala Ser Gly Asp Glu Gly Ser Pro Gln Arg Arg Glu Lys Ala Asn
            610                 615                 620
Gly Leu Ser Thr Pro Ser Glu Ser Pro His Phe His Leu Gly Leu Lys
625                 630                 635                 640
Ser Leu Val Asp Gly Tyr Lys Gln Trp Ser Ser Ala Pro Asn Leu
                    645                 650                 655
Val Lys Gly Pro Arg Ser Ser Pro Ala Leu Pro Gly Phe Thr Ser Leu
                    660                 665                 670
Met Glu Met Glu Asp Glu Asp Ser Glu Gly Pro Gly Ser Gly Glu Ser
            675                 680                 685
Arg Leu Gln His Ser Pro Ser Gln Ser Tyr Leu Cys Ile Pro Phe Pro
            690                 695                 700
Arg Gly Glu Asp Gly Asp Gly Pro Ser Ser Asp Gly Ile His Glu Glu
705                 710                 715                 720
Pro Thr Pro Val Asn Ser Ala Thr Ser Thr Pro Gln Leu Thr Pro Thr
                    725                 730                 735
Asn Ser Leu Lys Arg Gly Gly Ala His His Arg Arg Cys Glu Val Ala
            740                 745                 750
Leu Leu Gly Cys Gly Ala Val Leu Ala Ala Thr Gly Leu Gly Phe Asp
            755                 760                 765
Leu Leu Glu Ala Gly Lys Cys Gln Leu Leu Pro Leu Glu Glu Pro Glu
770                 775                 780
Pro Pro Ala Arg Glu Glu Lys Lys Arg Glu Gly Leu Phe Gln Arg
785                 790                 795                 800
Ser Ser Arg Pro Arg Arg Ser Thr Ser Pro Pro Ser Arg Lys Leu Phe
            805                 810                 815
Lys Lys Glu Glu Pro Met Leu Leu Leu Gly Asp Pro Ser Ala Ser Leu
            820                 825                 830
Thr Leu Leu Ser Leu Ser Ser Ile Ser Glu Cys Asn Ser Thr Arg Ser
            835                 840                 845
Leu Leu Arg Ser Asp Ser Asp Glu Ile Val Val Tyr Glu Met Pro Val
850                 855                 860
Ser Pro Val Glu Ala Pro Pro Leu Ser Pro Cys Thr His Asn Pro Leu
865                 870                 875                 880
Val Asn Val Arg Val Glu Arg Phe Lys Arg Asp Pro Asn Gln Ser Leu
                    885                 890                 895
Thr Pro Thr His Val Thr Leu Thr Thr Pro Ser Gln Pro Ser Ser His
                    900                 905                 910
Arg Arg Thr Pro Ser Asp Gly Ala Leu Lys Pro Glu Thr Leu Leu Ala
            915                 920                 925
Ser Arg Ser Pro Ser Ser Asn Gly Leu Ser Pro Ser Pro Gly Ala Gly
            930                 935                 940
Met Leu Lys Thr Pro Ser Pro Ser Arg Asp Pro Gly Glu Phe Pro Arg
945                 950                 955                 960
Leu Pro Asp Pro Asn Val Val Phe Pro Pro Thr Pro Arg Arg Trp Asn
                    965                 970                 975
Thr Gln Gln Asp Ser Thr Leu Glu Arg Pro Lys Thr Leu Glu Phe Leu
            980                 985                 990
Pro Arg Pro Arg Pro Ser Ala Asn Arg Gln Arg Leu Asp Pro Trp Trp
            995                 1000                1005
Phe Val Ser Pro Ser His Ala Arg Ser Thr Ser Pro Ala Asn Ser Ser
            1010                1015                1020
```

| Ser | Thr | Glu | Thr | Pro | Ser | Asn | Leu | Asp | Ser | Cys | Phe | Ala | Ser | Ser | Ser |
|---|---|---|---|---|---|---|---|---|---|---|---|---|---|---|---|
| 1025 | | | | 1030 | | | | 1035 | | | | 1040 | | | |

| Ser | Thr | Val | Glu | Glu | Arg | Pro | Gly | Leu | Pro | Ala | Leu | Leu | Pro | Phe | Gln |
|---|---|---|---|---|---|---|---|---|---|---|---|---|---|---|---|
| | | | 1045 | | | | 1050 | | | | 1055 | | | | |

| Ala | Gly | Pro | Leu | Pro | Pro | Thr | Glu | Arg | Thr | Leu | Leu | Asp | Leu | Asp | Ala |
|---|---|---|---|---|---|---|---|---|---|---|---|---|---|---|---|
| | | 1060 | | | | 1065 | | | | 1070 | | | | | |

| Glu | Gly | Gln | Ser | Gln | Asp | Ser | Thr | Val | Pro | Leu | Cys | Arg | Ala | Glu | Leu |
|---|---|---|---|---|---|---|---|---|---|---|---|---|---|---|---|
| | 1075 | | | | 1080 | | | | 1085 | | | | | | |

| Asn | Thr | His | Arg | Pro | Ala | Pro | Tyr | Glu | Ile | Gln | Gln | Glu | Phe | Trp | Ser |
|---|---|---|---|---|---|---|---|---|---|---|---|---|---|---|---|
| 1090 | | | | 1095 | | | | 1100 | | | | | | | |

<210> SEQ ID NO 3
<211> LENGTH: 2865
<212> TYPE: DNA
<213> ORGANISM: Human

<400> SEQUENCE: 3

```
atggaggagg aggaggggc ggtggccaag agtggggca cgaccccgc ggggcccgtc      60
tggaccgcgg tgttcgacta cgaggcggcg ggcgacgagg agctgaccct gcggaggggc     120
gatcgcgtcc aggtgctttc ccaagactgt gcggtgtccg cgacgaggg ctggtggacc     180
ggcagctcc ccagcggccg cgtgggcgtc ttccccagca actacgtggc ccccggcgcc     240
cccgctgcac ccgcgggcct ccagctgccc aggagatcc ccttccacga gctgcagcta     300
gaggagatca tcggtgtggg gggctttggc aaggtctatc gggccctgtg gcgtggcgag     360
gaggtggcag tcaaggccgc ccggctggac cctgagaagg accggcagt gacagcggag     420
caggtgtgcc aggaagcccg gctctttgga gccctgcagc accccaacat aattgccctt     480
agggcgcct gcctcaaccc ccacacctc tgcctagtga tggagtatgc ccggggtggt     540
gcactgagca gggtgctggc aggtcgccgg gtgccacctc acgtgctggt caactgggct     600
gtgcaggtgg cccggggcat gaactaccta cacaatgatg cccctgtgcc catcatccac     660
cgggacctca gtccatcaa catcctgatc ctggaggcca tcgagaacca caacctcgca     720
gacacggtgc tcaagatcac ggacttcggc ctcgcccgcg agtggcacaa gaccaccaag     780
atgagcgctg cggggaccta cgcctggatg gcgccggagg ttatccgtct ctccctcttc     840
tccaaaagca gtgatgtctg gagcttcggg gtgctgctgt gggagctgct gacggggag     900
gtcccctacc gtgagatcga cgccttggcc gtggcgtatg gcgtggctat gaataagctg     960
acgctgccca ttccctccac gtgccccgag ccctttgccc gctcctgga ggaatgctgg    1020
gacccagacc ccacgggcg gccagatttc ggtagcatct tgaagcggct tgaagtcatc    1080
gaacagtcag ccctgttcca gatgccactg gagtccttcc actcgctgca ggaagactgg    1140
aagctggaga ttcagcacat gtttgatgac cttcggacca aggagaagga gcttcggagc    1200
cgtgaggagg agctgctgcg ggcggcacag gagcagcgct tccaggagga gcagctgcgg    1260
cggcgggagc aggagctggc agaacgtgag atggacatcg tggaacggga gctgcacctg    1320
ctcatgtgcc agctgagcca ggagaagccc cgggtccgca agcgcaaggg caacttcaag    1380
cgcagccgcc tgctcaagct gcgggaaggc ggcagccaca tcagcctgcc ctctggctt    1440
gagcataaga tcacagtcca ggcctctcca actctggata gcggaaagg atccgatggg    1500
gccagccccc tgcaagccc agcatcatc cccggctga gggccattcg cctgactccc    1560
gtggactgtg gtggcagcag cagtggcagc agcagtggag gaagtgggac atggagccgc    1620
ggtgggcccc caagaagga agaactggtc gggggcaaga agaagggacg aacgtgggg    1680
```

-continued

```
cccagctcca ccctgcagaa ggagcgggtg ggaggagagg agaggctgaa ggggctgggg      1740
gaaggaagca aacagtggtc atcaagtgcc cccaacctgg gcaagtcccc caaacacaca      1800
cccatcgccc ctggcttcgc cagcctcaat gagatggagg agttcgcgga ggcagaggat      1860
ggaggcagca gcgtgccccc ttcccccta c tcgaccccgt cctacctctc agtgccactg      1920
cctgccgagc cctccccggg ggcgcgggcg ccgtgggagc cgacgccgtc cgcgcccccc      1980
gctcggtggg gacacggcgc ccggcggcgc tgcgacctgg cgctgctagg ctgcgccacg      2040
ctgctggggg ctgtgggcct gggcgccgac gtggccgagg cgcgcgcggc cgacggtgag      2100
gagcagcggc gctggctcga cggcctcttc tttccccgcg ccggccgctt ccgcggggc      2160
ctcagcccac ccgcgcgtcc ccacggccgc cgcgaagacg tgggccccgg cctgggcctg      2220
gcgcctcgg ccaccctcgt gtcgctgtcg tccgtgtccg actgcaactc cacgcgttca      2280
ctgctgcgct ctgacagtga cgaggccgca ccggccgcgc cctccccacc accctccccg      2340
cccgcgccca cacccacgcc ctcgcccagc accaaccccc tggtggacct ggagctggag      2400
agcttcaaga aggaccccg ccagtcgctc acgcccaccc acgtcacggc tgcatgcgct      2460
gtgagccgcg ggcaccggcg gacgccatcg gatgggcgc tggggcagcg ggggccgccc      2520
gagcccgcgg ccatggccc tggccctcgt gaccttctgg acttccccg cctgcccgac      2580
ccccaggccc tgttcccagc ccgcgccgg cccctgagt tcccaggccg ccccaccacc      2640
ctgacctttg ccccgagacc tcggccggct gccagtcgcc cccgcttgga cccctggaaa      2700
ctggtctcct tcggcggac actcaccatc tcgcctccca gcaggccaga cactccggag      2760
agccctgggc ccccagcgt gcagcccaca ctgctggaca tggacatgga ggggcagaac      2820
caagacagca cagtgcccct gtgcggggcc cacggctccc actaa                     2865
```

<210> SEQ ID NO 4
<211> LENGTH: 954
<212> TYPE: PRT
<213> ORGANISM: Human

<400> SEQUENCE: 4

```
Met Glu Glu Glu Gly Ala Val Ala Lys Glu Trp Gly Thr Thr Pro
  1               5                  10                  15

Ala Gly Pro Val Trp Thr Ala Val Phe Asp Tyr Glu Ala Ala Gly Asp
                 20                  25                  30

Glu Glu Leu Thr Leu Arg Arg Gly Asp Arg Val Gln Val Leu Ser Gln
             35                  40                  45

Asp Cys Ala Val Ser Gly Asp Glu Gly Trp Trp Thr Gly Gln Leu Pro
         50                  55                  60

Ser Gly Arg Val Gly Val Phe Pro Ser Asn Tyr Val Ala Pro Gly Ala
     65                  70                  75                  80

Pro Ala Pro Ala Gly Leu Gln Leu Pro Gln Glu Ile Pro Phe His
                 85                  90                  95

Glu Leu Gln Leu Glu Glu Ile Ile Gly Val Gly Phe Gly Lys Val
                100                 105                 110

Tyr Arg Ala Leu Trp Arg Gly Glu Glu Val Ala Val Lys Ala Ala Arg
            115                 120                 125

Leu Asp Pro Glu Lys Asp Pro Ala Val Thr Ala Glu Gln Val Cys Gln
        130                 135                 140

Glu Ala Arg Leu Phe Gly Ala Leu Gln His Pro Asn Ile Ile Ala Leu
    145                 150                 155                 160
```

-continued

```
Arg Gly Ala Cys Leu Asn Pro Pro His Leu Cys Leu Val Met Glu Tyr
            165                 170                 175
Ala Arg Gly Gly Ala Leu Ser Arg Val Leu Ala Gly Arg Arg Val Pro
        180                 185                 190
Pro His Val Leu Val Asn Trp Ala Val Gln Val Ala Arg Gly Met Asn
    195                 200                 205
Tyr Leu His Asn Asp Ala Pro Val Pro Ile Ile His Arg Asp Leu Lys
210                 215                 220
Ser Ile Asn Ile Leu Ile Leu Glu Ala Ile Glu Asn His Asn Leu Ala
225                 230                 235                 240
Asp Thr Val Leu Lys Ile Thr Asp Phe Gly Leu Ala Arg Glu Trp His
                245                 250                 255
Lys Thr Thr Lys Met Ser Ala Ala Gly Thr Tyr Ala Trp Met Ala Pro
            260                 265                 270
Glu Val Ile Arg Leu Ser Leu Phe Ser Lys Ser Ser Asp Val Trp Ser
        275                 280                 285
Phe Gly Val Leu Leu Trp Glu Leu Leu Thr Gly Glu Val Pro Tyr Arg
    290                 295                 300
Glu Ile Asp Ala Leu Ala Val Ala Tyr Gly Val Ala Met Asn Lys Leu
305                 310                 315                 320
Thr Leu Pro Ile Pro Ser Thr Cys Pro Glu Pro Phe Ala Arg Leu Leu
                325                 330                 335
Glu Glu Cys Trp Asp Pro Asp Pro His Gly Arg Pro Asp Phe Gly Ser
            340                 345                 350
Ile Leu Lys Arg Leu Glu Val Ile Glu Gln Ser Ala Leu Phe Gln Met
        355                 360                 365
Pro Leu Glu Ser Phe His Ser Leu Gln Glu Asp Trp Lys Leu Glu Ile
    370                 375                 380
Gln His Met Phe Asp Asp Leu Arg Thr Lys Glu Lys Glu Leu Arg Ser
385                 390                 395                 400
Arg Glu Glu Glu Leu Leu Arg Ala Ala Gln Glu Gln Arg Phe Gln Glu
                405                 410                 415
Glu Gln Leu Arg Arg Arg Glu Gln Glu Leu Ala Glu Arg Glu Met Asp
            420                 425                 430
Ile Val Glu Arg Glu Leu His Leu Leu Met Cys Gln Leu Ser Gln Glu
        435                 440                 445
Lys Pro Arg Val Arg Lys Arg Lys Gly Asn Phe Lys Arg Ser Arg Leu
    450                 455                 460
Leu Lys Leu Arg Glu Gly Gly Ser His Ile Ser Leu Pro Ser Gly Phe
465                 470                 475                 480
Glu His Lys Ile Thr Val Gln Ala Ser Pro Thr Leu Asp Lys Arg Lys
                485                 490                 495
Gly Ser Asp Gly Ala Ser Pro Pro Ala Ser Pro Ser Ile Ile Pro Arg
            500                 505                 510
Leu Arg Ala Ile Arg Leu Thr Pro Val Asp Cys Gly Gly Ser Ser Ser
        515                 520                 525
Gly Ser Ser Ser Gly Gly Ser Gly Thr Trp Ser Arg Gly Gly Pro Pro
    530                 535                 540
Lys Lys Glu Glu Leu Val Gly Gly Lys Lys Lys Gly Arg Thr Trp Gly
545                 550                 555                 560
Pro Ser Ser Thr Leu Gln Lys Glu Arg Val Gly Gly Glu Glu Arg Leu
                565                 570                 575
Lys Gly Leu Gly Glu Gly Ser Lys Gln Trp Ser Ser Ser Ala Pro Asn
```

```
            580                 585                 590
Leu Gly Lys Ser Pro Lys His Thr Pro Ile Ala Pro Gly Phe Ala Ser
            595                 600                 605
Leu Asn Glu Met Glu Glu Phe Ala Glu Ala Glu Asp Gly Gly Ser Ser
        610                 615                 620
Val Pro Pro Ser Pro Tyr Ser Thr Pro Ser Tyr Leu Ser Val Pro Leu
625                 630                 635                 640
Pro Ala Glu Pro Ser Pro Gly Ala Arg Ala Pro Trp Glu Pro Thr Pro
                645                 650                 655
Ser Ala Pro Pro Ala Arg Trp Gly His Gly Ala Arg Arg Cys Asp
            660                 665                 670
Leu Ala Leu Leu Gly Cys Ala Thr Leu Leu Gly Ala Val Gly Leu Gly
            675                 680                 685
Ala Asp Val Ala Glu Ala Arg Ala Asp Gly Glu Glu Gln Arg Arg
        690                 695                 700
Trp Leu Asp Gly Leu Phe Phe Pro Arg Ala Gly Arg Phe Pro Arg Gly
705                 710                 715                 720
Leu Ser Pro Pro Ala Arg Pro His Gly Arg Arg Glu Asp Val Gly Pro
                725                 730                 735
Gly Leu Gly Leu Ala Pro Ser Ala Thr Leu Val Ser Leu Ser Ser Val
            740                 745                 750
Ser Asp Cys Asn Ser Thr Arg Ser Leu Leu Arg Ser Asp Ser Asp Glu
            755                 760                 765
Ala Ala Pro Ala Ala Pro Ser Pro Pro Ser Pro Pro Ala Pro Thr
        770                 775                 780
Pro Thr Pro Ser Pro Ser Thr Asn Pro Leu Val Asp Leu Glu Leu Glu
785                 790                 795                 800
Ser Phe Lys Lys Asp Pro Arg Gln Ser Leu Thr Pro Thr His Val Thr
                805                 810                 815
Ala Ala Cys Ala Val Ser Arg Gly His Arg Arg Thr Pro Ser Asp Gly
            820                 825                 830
Ala Leu Gly Gln Arg Gly Pro Pro Glu Pro Ala Gly His Gly Pro Gly
            835                 840                 845
Pro Arg Asp Leu Leu Asp Phe Pro Arg Leu Pro Asp Pro Gln Ala Leu
        850                 855                 860
Phe Pro Ala Arg Arg Pro Pro Glu Phe Pro Gly Arg Pro Thr Thr
865                 870                 875                 880
Leu Thr Phe Ala Pro Arg Pro Arg Ala Ala Ser Arg Pro Arg Leu
                885                 890                 895
Asp Pro Trp Lys Leu Val Ser Phe Gly Arg Thr Leu Thr Ile Ser Pro
            900                 905                 910
Pro Ser Arg Pro Asp Thr Pro Glu Ser Pro Gly Pro Pro Ser Val Gln
            915                 920                 925
Pro Thr Leu Leu Asp Met Asp Met Glu Gly Gln Asn Gln Asp Ser Thr
        930                 935                 940
Val Pro Leu Cys Gly Ala His Gly Ser His
945                 950

<210> SEQ ID NO 5
<211> LENGTH: 2544
<212> TYPE: DNA
<213> ORGANISM: Human

<400> SEQUENCE: 5
```

-continued

| | |
|---|---|
| atggagccct tgaagagcct cttcctcaag agccctctag ggtcatggaa tggcagtggc | 60 |
| agcggggtg gtgggggcgg tggaggaggc cggcctgagg ggtctccaaa ggcagcgggt | 120 |
| tatgccaacc cggtgtggac agccctgttc gactacgagc ccagtgggca ggatgagctg | 180 |
| gccctgagga agggtgaccg tgtggaggtg ctgtcccggg acgcagccat ctcaggagac | 240 |
| gagggctggt gggcgggcca ggtgggtggc caggtgggca tcttcccgtc caactatgtg | 300 |
| tctcggggtg gcggcccgcc ccctgcgag gtggccagct tccaggagct gcggctggag | 360 |
| gaggtgatcg gcattggagg cttggcaag gtgtacaggg gcagctggcg aggtgagctg | 420 |
| gtggctgtga aggcagctcg ccaggacccc gatgaggaca tcagtgtgac agccgagagc | 480 |
| gttcgccagg aggcccggct cttcgccatg ctggcacacc ccaacatcat tgccctcaag | 540 |
| gctgtgtgcc tggaggagcc caacctgtgc ctggtgatgg agtatgcagc cggtgggccc | 600 |
| ctcagccgag ctctggccgg gcggcgcgtg cctccccatg tgctggtcaa ctgggctgtg | 660 |
| cagattgccc gtgggatgca ctacctgcac tgcgaggccc tggtgcccgt catccaccgt | 720 |
| gatctcaagt ccaacaacat tttgctgctg cagcccattg agagtgacga catggagcac | 780 |
| aagaccctga gatcaccga ctttggcctg gcccgagagt ggcacaaaac cacacaaatg | 840 |
| agtgccgcgg gcacctacgc ctggatggct cctgagttta caaggcctc caccttctct | 900 |
| aagggcagtg acgtctggag ttttgggtg ctgctgtggg aactgctgac cggggaggtg | 960 |
| ccataccgtg gcattgactg ccttgctgtg gcctatggcg tagctgttaa caagctcaca | 1020 |
| ctgcccatcc catccacctg ccccgagccc ttcgcacagc ttatggccga ctgctgggcg | 1080 |
| caggaccccc accgcaggcc cgacttcgcc tccatcctgc agcagttgga ggcgctggag | 1140 |
| gcacaggtcc tacgggaaat gccgcgggac tccttccatt ccatgcagga aggctggaag | 1200 |
| cgcgagatcc agggtctctt cgacgagctg cgagccaagg aaaaggaact actgagccgc | 1260 |
| gaggaggagc tgacgcgagc ggcgcgcgag cagcggtcac aggcggagca gctgcggcgg | 1320 |
| cgcgagcacc tgctggccca gtgggagcta gaggtgttcg agcgcgagct gacgctgctg | 1380 |
| ctgcagcagg tggaccgcga cgaccgcac gtgcgccgcc gccgcgggac attcaagcgc | 1440 |
| agcaagctcc gggcgcgcga cggcggcgag cgtatcagca tgccactcga cttcaagcac | 1500 |
| cgcatcaccg tgcaggcctc acccggcctt gaccggagga gaaacgtctt cgaggtcggg | 1560 |
| cctgggatt cgcccacctt tccccggttc cgagccatcc agttggagcc tgcagagcca | 1620 |
| ggccaggcat ggggccgcca gtccccccga cgtctggagg actcaagcaa tggagagcgg | 1680 |
| cgagcatgct gggcttgggg tcccagttcc cccaagcctg gggaagccca gaatggggagg | 1740 |
| agaaggtccc gcatggacga agccacatgg tacctggatt cagatgactc atcccccta | 1800 |
| ggatctcctt ccacacccccc agcactcaat ggtaaccccc gcggcctag cctggagccc | 1860 |
| gaggagccca agaggcctgt ccccgcagag cgcggtagca gctctgggac gcccaagctg | 1920 |
| atccagcggg cgctgctgcg cggcaccgcc ctgctcgcct cgctgggcct tggccgcgac | 1980 |
| ctgcagccgc cggagggccc aggacgcgag cgcgggagt ccccgacaac accccccacg | 2040 |
| ccaacgcccg cgccctgccc gaccgagccg ccccctccc cgctcatctg cttctcgctc | 2100 |
| aagacgcccg actccccgcc cactcctgca ccctgttgc tggacctggg tatccctgtg | 2160 |
| ggccagcggt cagccaagag ccccgacgt gaggaggagc ccgcggagg cactgtctca | 2220 |
| ccccaccgg ggacatcacg ctctgctcct ggcaccccag gcaccccacg ttcaccaccc | 2280 |
| ctgggcctca tcagccgacc tcggccctcg ccccttcgca gccgcattga tccctggagc | 2340 |
| tttgtgtcag ctgggccacg gccttctccc ctgccatcac cacagcctgc accccgccga | 2400 |

```
gcaccctgga ccttgttccc ggactcagac cccttctggg actccccacc tgccaacccc    2460
ttccaggggg gccccagga ctgcagggca cagaccaaag acatgggtgc ccaggccccg    2520
tgggtgccgg aagcggggcc ttga                                          2544
```

<210> SEQ ID NO 6
<211> LENGTH: 847
<212> TYPE: PRT
<213> ORGANISM: Human

<400> SEQUENCE: 6

```
Met Glu Pro Leu Lys Ser Leu Phe Leu Lys Ser Pro Leu Gly Ser Trp
  1               5                  10                  15

Asn Gly Ser Gly Ser Gly Gly Gly Gly Gly Gly Gly Gly Arg Pro
             20                  25                  30

Glu Gly Ser Pro Lys Ala Ala Gly Tyr Ala Asn Pro Val Trp Thr Ala
         35                  40                  45

Leu Phe Asp Tyr Glu Pro Ser Gly Gln Asp Glu Leu Ala Leu Arg Lys
     50                  55                  60

Gly Asp Arg Val Glu Val Leu Ser Arg Asp Ala Ala Ile Ser Gly Asp
 65                  70                  75                  80

Glu Gly Trp Trp Ala Gly Gln Val Gly Gly Gln Val Gly Ile Phe Pro
                 85                  90                  95

Ser Asn Tyr Val Ser Arg Gly Gly Gly Pro Pro Pro Cys Glu Val Ala
                100                 105                 110

Ser Phe Gln Glu Leu Arg Leu Glu Glu Val Ile Gly Ile Gly Gly Phe
            115                 120                 125

Gly Lys Val Tyr Arg Gly Ser Trp Arg Gly Glu Leu Val Ala Val Lys
        130                 135                 140

Ala Ala Arg Gln Asp Pro Asp Glu Asp Ile Ser Val Thr Ala Glu Ser
145                 150                 155                 160

Val Arg Gln Glu Ala Arg Leu Phe Ala Met Leu Ala His Pro Asn Ile
                165                 170                 175

Ile Ala Leu Lys Ala Val Cys Leu Glu Glu Pro Asn Leu Cys Leu Val
            180                 185                 190

Met Glu Tyr Ala Ala Gly Gly Pro Leu Ser Arg Ala Leu Ala Gly Arg
        195                 200                 205

Arg Val Pro Pro His Val Leu Val Asn Trp Ala Val Gln Ile Ala Arg
    210                 215                 220

Gly Met His Tyr Leu His Cys Glu Ala Leu Val Pro Val Ile His Arg
225                 230                 235                 240

Asp Leu Lys Ser Asn Asn Ile Leu Leu Leu Gln Pro Ile Glu Ser Asp
                245                 250                 255

Asp Met Glu His Lys Thr Leu Lys Ile Thr Asp Phe Gly Leu Ala Arg
            260                 265                 270

Glu Trp His Lys Thr Thr Gln Met Ser Ala Ala Gly Thr Tyr Ala Trp
        275                 280                 285

Met Ala Pro Glu Val Ile Lys Ala Ser Thr Phe Ser Lys Gly Ser Asp
    290                 295                 300

Val Trp Ser Phe Gly Val Leu Leu Trp Glu Leu Thr Gly Glu Val
305                 310                 315                 320

Pro Tyr Arg Gly Ile Asp Cys Leu Ala Val Ala Tyr Gly Val Ala Val
                325                 330                 335

Asn Lys Leu Thr Leu Pro Ile Pro Ser Thr Cys Pro Glu Pro Phe Ala
```

```
                340                 345                 350
Gln Leu Met Ala Asp Cys Trp Ala Gln Asp Pro His Arg Arg Pro Asp
            355                 360                 365
Phe Ala Ser Ile Leu Gln Gln Leu Glu Ala Leu Glu Ala Gln Val Leu
            370                 375                 380
Arg Glu Met Pro Arg Asp Ser Phe His Ser Met Gln Glu Gly Trp Lys
385                 390                 395                 400
Arg Glu Ile Gln Gly Leu Phe Asp Glu Leu Arg Ala Lys Glu Lys Glu
                405                 410                 415
Leu Leu Ser Arg Glu Glu Glu Leu Thr Arg Ala Ala Arg Glu Gln Arg
            420                 425                 430
Ser Gln Ala Glu Gln Leu Arg Arg Glu His Leu Leu Ala Gln Trp
            435                 440                 445
Glu Leu Glu Val Phe Glu Arg Glu Leu Thr Leu Leu Gln Gln Val
            450                 455                 460
Asp Arg Glu Arg Pro His Val Arg Arg Arg Gly Thr Phe Lys Arg
465                 470                 475                 480
Ser Lys Leu Arg Ala Arg Asp Gly Gly Glu Arg Ile Ser Met Pro Leu
                485                 490                 495
Asp Phe Lys His Arg Ile Thr Val Gln Ala Ser Pro Gly Leu Asp Arg
            500                 505                 510
Arg Arg Asn Val Phe Glu Val Gly Pro Gly Asp Ser Pro Thr Phe Pro
            515                 520                 525
Arg Phe Arg Ala Ile Gln Leu Glu Pro Ala Glu Pro Gly Gln Ala Trp
            530                 535                 540
Gly Arg Gln Ser Pro Arg Arg Leu Glu Asp Ser Ser Asn Gly Glu Arg
545                 550                 555                 560
Arg Ala Cys Trp Ala Trp Gly Pro Ser Ser Pro Lys Pro Gly Glu Ala
                565                 570                 575
Gln Asn Gly Arg Arg Arg Ser Arg Met Asp Glu Ala Thr Trp Tyr Leu
            580                 585                 590
Asp Ser Asp Asp Ser Ser Pro Leu Gly Ser Pro Ser Thr Pro Pro Ala
            595                 600                 605
Leu Asn Gly Asn Pro Pro Arg Pro Ser Leu Glu Pro Glu Glu Pro Lys
            610                 615                 620
Arg Pro Val Pro Ala Glu Arg Gly Ser Ser Ser Gly Thr Pro Lys Leu
625                 630                 635                 640
Ile Gln Arg Ala Leu Leu Arg Gly Thr Ala Leu Leu Ala Ser Leu Gly
                645                 650                 655
Leu Gly Arg Asp Leu Gln Pro Pro Gly Gly Pro Gly Arg Glu Arg Gly
            660                 665                 670
Glu Ser Pro Thr Thr Pro Pro Thr Pro Thr Pro Ala Pro Cys Pro Thr
            675                 680                 685
Glu Pro Pro Pro Ser Pro Leu Ile Cys Phe Ser Leu Lys Thr Pro Asp
            690                 695                 700
Ser Pro Pro Thr Pro Ala Pro Leu Leu Leu Asp Leu Gly Ile Pro Val
705                 710                 715                 720
Gly Gln Arg Ser Ala Lys Ser Pro Arg Arg Glu Glu Pro Arg Gly
                725                 730                 735
Gly Thr Val Ser Pro Pro Gly Thr Ser Arg Ser Ala Pro Gly Thr
            740                 745                 750
Pro Gly Thr Pro Arg Ser Pro Pro Leu Gly Leu Ile Ser Arg Pro Arg
            755                 760                 765
```

```
Pro Ser Pro Leu Arg Ser Arg Ile Asp Pro Trp Ser Phe Val Ser Ala
    770                 775                 780
Gly Pro Arg Pro Ser Pro Leu Pro Ser Pro Gln Pro Ala Pro Arg Arg
785                 790                 795                 800
Ala Pro Trp Thr Leu Phe Pro Asp Ser Asp Pro Phe Trp Asp Ser Pro
                805                 810                 815
Pro Ala Asn Pro Phe Gln Gly Gly Pro Gln Asp Cys Arg Ala Gln Thr
            820                 825                 830
Lys Asp Met Gly Ala Gln Ala Pro Trp Val Pro Glu Ala Gly Pro
        835                 840                 845

<210> SEQ ID NO 7
<211> LENGTH: 3111
<212> TYPE: DNA
<213> ORGANISM: Human

<400> SEQUENCE: 7
atggctttgc ggggcgccgc gggagcgacc gacacccccgg tgtcctcggc cggggagcc       60 cccggcggct cagcgtcctc gtcgtccacc tcctcgggcg ctcggcctc ggcgggcgcg      120 gggctgtggg ccgcgctcta tgactacgag gctcgcggcg aggacgagct gagcctgcgg      180
cgcggccagc tggtggaggt gttgtcgcag acgccgccg tgtcgggcga cgagggctgg      240
tgggcaggcc aggtgcagcg cgcctcggc atcttccccg ccaactacgt ggctccctgc      300
cgcccggccg ccagccccgc cgccgcgccc tcgcggccca gctccccggt acacgtcgcc      360
ttcgagcggt tggagctgaa ggagctcatc ggcgctgggg gcttcgggca ggtgtaccgc      420
gccacctggc agggccagga ggtggccgtg aaggcggcgc gccaggaccc ggagcaggac      480 gcggcggcg ctgccgagag cgtgcggcgc gaggctcggc tcttcgccat gctgcggcac      540
cccaacatca tcgagctgcg cggcgtgtgc ctgcagcagc cgcacctctg cctggtgctg      600
gagttcgccc gcggcggagc gctcaaccga gcgctggccg ctgccaacgc cgccccggac      660
ccgcgcgcgc ccggccccg ccgcgcgcgc cgcatccctc cgcacgtgct ggtcaactgg      720
gccgtgcaga tagcgcgggg catgctctac ctgcatgagg aggccttcgt gcccatcctg      780
caccgggacc tcaagtccag caacattttg ctacttgaag atagaaaca tgatgacatc      840 tgcaataaaa cttttgaagat tacagatttt gggttggcga gggaatggca caggaccacc      900
aaaatgagca cagcaggcac ctatgcctgg atggcccccg aagtgatcaa gtcttccttg      960
ttttctaagg gaagcgacat ctggagctgt ggagtgctgc tgtgggaact gctcaccgga     1020 gaagtccccct atcggggcat tgatggcctc gccgtggctt atgggtgagc agtcaataaa     1080
ctcactttgc ccattccatc cacctgcccct gagccgtttg ccaagctcat gaaagaatgc     1140
tggcaacaag accctcatat tcgtccatcg tttgccttaa ttctcgaaca gttgactgct     1200 attgagggg cagtgatgac tgagatgcct caagaatctt ttcattccat gcaagatgac     1260
tggaaactag aaattcaaca atgtttgat gagttgaaga caaggaaaaa ggagctgcga     1320
tcccgggaag aggagctgac tcgggcggct ctgcagcaga gtctcagga ggagctgcta     1380 aagcggcgtg agcagcagct ggcagagcgc gagatcgacg tgctgagcg gaacttaac     1440 attctgatat tccagctaaa ccaggagaag cccaaggtaa agaagaggaa gggcaagttt     1500
aagagaagtc gtttaaagct caaagatgga catcgaatca gtttaccttc agatttccag     1560
cacaagataa ccgtgcaggc ctctcccaac ttgacaaac ggcggagcct gaacagcagc     1620
agttccagtc ccccgagcag ccccacaatg atgccccgac tccgagccat acagttgact     1680
```

```
tcagatgaaa gcaataaaac ttggggaagg aacacagtct ttcgacaaga agaatttgag   1740
gatgtaaaaa ggaattttaa gaaaaaaggt tgtacctggg gaccaaattc cattcaaatg   1800
aaagatagaa cagattgcaa agaaaggata agacctctct ccgatggcaa cagtccttgg   1860
tcaactatct aataaaaaaa tcagaaaacc atgcccttgg cttcattgtt tgtggaccag   1920
ccagggtcct gtgaagagcc aaaactttcc cctgatggat tagaacacag aaaaccaaaa   1980
caaataaaat tgcctagtca ggcctacatt gatctacctc ttgggaaaga tgctcagaga   2040
gagaatcctg cagaagctgg aagctgggag gaggcagcct ctgcgaatgc tgccacagtc   2100
accattgaga tggctcctac gaatagtctg agtagatccc cccagagaaa gaaaacggag   2160
tcagctctgt atgggtgcac cgtccttctg gcatcggtgg ctctgggact ggacctcaga   2220
gagcttcata aagcacaggc tgctgaagaa ccgttgccca aggaagagaa gaagaaacga   2280
gagggaatct tccagcgggc ttccaagtcc cgcagaagcg ccagtcctcc cacaagcctg   2340
tcatccacct gtggggaggc cagcagccca ccctccctgc cactgtcaag tgccctgggc   2400
atcctctcca caccttcttt ctccacaaag tgcctgctgc agatggacag tgaagatcca   2460
ctggtggaca gtgcacctgt cacttgtgac tctgagatgc tcactccgga ttttttgtccc   2520
actgccccag gaagtggtcg tgagccagcc ctcatgccaa gcttgacac tgattgtagt    2580
gtatcaagaa acttgccgtc ttccttccta cagcggacat gtgggaatgt acctactgt    2640
gcttcttcaa acatagacc atcacatcac agacggacca tgtctgatgg aaatccgacc   2700
ccaactggtg caactattat ctcagccact ggagcctctg cactgccact ctgcccctca   2760
cctgctcctc acagtcatct gccaagggag gtctcaccca agaagcacag cactgtccac   2820
atcgtgcctc agcgtcgccc tgcctccctg agaagccgct cagatctgcc tcaggcttac   2880
ccacagacag cagtgtctca gctggcacag actgcctgtg tagtgggtcg cccaggacca   2940
catcccaccc aattcctcgc tgccaaggag agaactaaat cccatgtgcc ttcattactg   3000
gatgttgacg tggaaggtca gagcagggac tacactgtgc cactgggtag aatgaggagc   3060
aaaaccagcc ggccatctat atatgaactg gagaaagaat tcctgtctta a           3111
```

<210> SEQ ID NO 8
<211> LENGTH: 1036
<212> TYPE: PRT
<213> ORGANISM: Human

<400> SEQUENCE: 8

Met Ala Leu Arg Gly Ala Ala Gly Ala Thr Asp Thr Pro Val Ser Ser
 1               5                  10                  15

Ala Gly Gly Ala Pro Gly Gly Ser Ala Ser Ser Ser Thr Ser Ser
            20                  25                  30

Gly Gly Ser Ala Ser Ala Gly Ala Gly Leu Trp Ala Ala Leu Tyr Asp
        35                  40                  45

Tyr Glu Ala Arg Gly Glu Asp Glu Leu Ser Leu Arg Arg Gly Gln Leu
    50                  55                  60

Val Glu Val Leu Ser Gln Asp Ala Ala Val Ser Gly Asp Glu Gly Trp
65                  70                  75                  80

Trp Ala Gly Gln Val Gln Arg Arg Leu Gly Ile Phe Pro Ala Asn Tyr
                85                  90                  95

Val Ala Pro Cys Arg Pro Ala Ala Ser Pro Ala Pro Pro Ser Arg
                100                 105                 110

Pro Ser Ser Pro Val His Val Ala Phe Glu Arg Leu Glu Leu Lys Glu

```
            115                 120                 125
Leu Ile Gly Ala Gly Gly Phe Gly Gln Val Tyr Arg Ala Thr Trp Gln
            130                 135                 140
Gly Gln Glu Val Ala Val Lys Ala Ala Arg Gln Asp Pro Glu Gln Asp
145                 150                 155                 160
Ala Ala Ala Ala Glu Ser Val Arg Arg Glu Ala Arg Leu Phe Ala
                165                 170                 175
Met Leu Arg His Pro Asn Ile Ile Glu Leu Arg Gly Val Cys Leu Gln
                180                 185                 190
Gln Pro His Leu Cys Leu Val Leu Glu Phe Ala Arg Gly Gly Ala Leu
            195                 200                 205
Asn Arg Ala Leu Ala Ala Ala Asn Ala Ala Pro Asp Pro Arg Ala Pro
210                 215                 220
Gly Pro Arg Arg Ala Arg Arg Ile Pro Pro His Val Leu Val Asn Trp
225                 230                 235                 240
Ala Val Gln Ile Ala Arg Gly Met Leu Tyr Leu His Glu Glu Ala Phe
                245                 250                 255
Val Pro Ile Leu His Arg Asp Leu Lys Ser Ser Asn Ile Leu Leu Leu
            260                 265                 270
Glu Glu Ile Glu His Asp Asp Ile Cys Asn Lys Thr Leu Lys Ile Thr
            275                 280                 285
Asp Phe Gly Leu Ala Arg Glu Trp His Arg Thr Thr Lys Met Ser Thr
290                 295                 300
Ala Gly Thr Tyr Ala Trp Met Ala Pro Glu Val Ile Lys Ser Ser Leu
305                 310                 315                 320
Phe Ser Lys Gly Ser Asp Ile Trp Ser Cys Gly Val Leu Leu Trp Glu
                325                 330                 335
Leu Leu Thr Gly Glu Val Pro Tyr Arg Gly Ile Asp Gly Leu Ala Val
            340                 345                 350
Ala Tyr Gly Val Ala Val Asn Lys Leu Thr Leu Pro Ile Pro Ser Thr
            355                 360                 365
Cys Pro Glu Pro Phe Ala Lys Leu Met Lys Glu Cys Trp Gln Gln Asp
370                 375                 380
Pro His Ile Arg Pro Ser Phe Ala Leu Ile Leu Glu Gln Leu Thr Ala
385                 390                 395                 400
Ile Glu Gly Ala Val Met Thr Glu Met Pro Gln Glu Ser Phe His Ser
                405                 410                 415
Met Gln Asp Asp Trp Lys Leu Glu Ile Gln Gln Met Phe Asp Glu Leu
            420                 425                 430
Arg Thr Lys Glu Lys Glu Leu Arg Ser Arg Glu Glu Glu Leu Thr Arg
            435                 440                 445
Ala Ala Leu Gln Gln Lys Ser Gln Glu Glu Leu Leu Lys Arg Arg Glu
            450                 455                 460
Gln Gln Leu Ala Glu Arg Glu Ile Asp Val Leu Glu Arg Glu Leu Asn
465                 470                 475                 480
Ile Leu Ile Phe Gln Leu Asn Gln Glu Lys Pro Lys Val Lys Lys Arg
                485                 490                 495
Lys Gly Lys Phe Lys Arg Ser Arg Leu Lys Leu Lys Asp Gly His Arg
            500                 505                 510
Ile Ser Leu Pro Ser Asp Phe Gln His Lys Ile Thr Val Gln Ala Ser
            515                 520                 525
Pro Asn Leu Asp Lys Arg Arg Ser Leu Asn Ser Ser Ser Ser Ser Pro
            530                 535                 540
```

```
Pro Ser Ser Pro Thr Met Met Pro Arg Leu Arg Ala Ile Gln Leu Thr
545                 550                 555                 560

Ser Asp Glu Ser Asn Lys Thr Trp Gly Arg Asn Thr Val Phe Arg Gln
                565                 570                 575

Glu Glu Phe Glu Asp Val Lys Arg Asn Phe Lys Lys Gly Cys Thr
            580                 585                 590

Trp Gly Pro Asn Ser Ile Gln Met Lys Asp Arg Thr Asp Cys Lys Glu
            595                 600                 605

Arg Ile Arg Pro Leu Ser Asp Gly Asn Ser Pro Trp Ser Thr Ile Leu
        610                 615                 620

Ile Lys Asn Gln Lys Thr Met Pro Leu Ala Ser Leu Phe Val Asp Gln
625                 630                 635                 640

Pro Gly Ser Cys Glu Glu Pro Lys Leu Ser Pro Asp Gly Leu Glu His
                645                 650                 655

Arg Lys Pro Lys Gln Ile Lys Leu Pro Ser Gln Ala Tyr Ile Asp Leu
            660                 665                 670

Pro Leu Gly Lys Asp Ala Gln Arg Glu Asn Pro Ala Glu Ala Gly Ser
            675                 680                 685

Trp Glu Glu Ala Ala Ser Ala Asn Ala Ala Thr Val Thr Ile Glu Met
690                 695                 700

Ala Pro Thr Asn Ser Leu Ser Arg Ser Pro Gln Arg Lys Lys Thr Glu
705                 710                 715                 720

Ser Ala Leu Tyr Gly Cys Thr Val Leu Leu Ala Ser Val Ala Leu Gly
                725                 730                 735

Leu Asp Leu Arg Glu Leu His Lys Ala Gln Ala Ala Glu Glu Pro Leu
            740                 745                 750

Pro Lys Glu Glu Lys Lys Arg Glu Gly Ile Phe Gln Arg Ala Ser
            755                 760                 765

Lys Ser Arg Arg Ser Ala Ser Pro Pro Thr Ser Leu Ser Ser Thr Cys
770                 775                 780

Gly Glu Ala Ser Ser Pro Pro Ser Leu Pro Leu Ser Ser Ala Leu Gly
785                 790                 795                 800

Ile Leu Ser Thr Pro Ser Phe Ser Thr Lys Cys Leu Leu Gln Met Asp
                805                 810                 815

Ser Glu Asp Pro Leu Val Asp Ser Ala Pro Val Thr Cys Asp Ser Glu
            820                 825                 830

Met Leu Thr Pro Asp Phe Cys Pro Thr Ala Pro Gly Ser Gly Arg Glu
            835                 840                 845

Pro Ala Leu Met Pro Arg Leu Asp Thr Asp Cys Ser Val Ser Arg Asn
850                 855                 860

Leu Pro Ser Ser Phe Leu Gln Arg Thr Cys Gly Asn Val Pro Tyr Cys
865                 870                 875                 880

Ala Ser Ser Lys His Arg Pro Ser His His Arg Arg Thr Met Ser Asp
                885                 890                 895

Gly Asn Pro Thr Pro Thr Gly Ala Thr Ile Ile Ser Ala Thr Gly Ala
            900                 905                 910

Ser Ala Leu Pro Leu Cys Pro Ser Pro Ala Pro His Ser His Leu Pro
            915                 920                 925

Arg Glu Val Ser Pro Lys Lys His Ser Thr Val His Ile Val Pro Gln
            930                 935                 940

Arg Arg Pro Ala Ser Leu Arg Ser Arg Ser Asp Leu Pro Gln Ala Tyr
945                 950                 955                 960
```

-continued

```
Pro Gln Thr Ala Val Ser Gln Leu Ala Gln Thr Ala Cys Val Val Gly
                965                 970                 975

Arg Pro Gly Pro His Pro Thr Gln Phe Leu Ala Ala Lys Glu Arg Thr
            980                 985                 990

Lys Ser His Val Pro Ser Leu Leu Asp Val Asp Val Glu Gly Gln Ser
        995                 1000                1005

Arg Asp Tyr Thr Val Pro Leu Gly Arg Met Arg Ser Lys Thr Ser Arg
    1010                1015                1020

Pro Ser Ile Tyr Glu Leu Glu Lys Glu Phe Leu Ser
1025                1030                1035
```